United States Patent [19]
Yang et al.

[11] Patent Number: 6,030,775
[45] Date of Patent: Feb. 29, 2000

[54] METHODS AND REAGENTS FOR TYPING HLA CLASS I GENES

[76] Inventors: Soo Young Yang, 444 E. 75th St.; Nezih Cereb, 1233 York Ave. #131, both of New York, N.Y. 10021

[21] Appl. No.: 08/577,081

[22] Filed: Dec. 22, 1995

[51] Int. Cl.[7] .................................................. C12Q 1/68
[52] U.S. Cl. ........................ 435/6; 436/501; 536/23.1; 536/24.1; 536/24.3; 536/24.31; 536/24.32; 536/24.33
[58] Field of Search ................... 435/5, 6, 810; 436/501; 536/23.1, 24.1, 24.3–24.33; 935/77, 78

[56] References Cited

U.S. PATENT DOCUMENTS

| | | | |
|---|---|---|---|
| 4,582,788 | 4/1986 | Erlich | 435/6 |
| 5,424,184 | 6/1995 | Santamaria et al. | 435/6 |

OTHER PUBLICATIONS

1988 Stratagene Catalog (published by Stratagene, 11011 North Torrey Pines Rd., La Jolla, California 92037), 1988.

Gao et al. "Characterization of HLA–A Polymorphism by Locus–Specific Polymerase Chain Reaction Amplification and Oligonucleotide Hybridization" *Human Immunology* 41: 267–279 (1994).

Joseph et al., "Classification of Mutations at the HLA–A Locus by Use of the Polymerase Chain Reaction", *Environmental and Molecular Mutagenesis* 22: 152–156 (1993).

Lawlor et al., "Ancient HLA genes from 7,500 year–old archaelogical remains", *nature* 349: 785788 (1991).

Malissen et al., "Exon/Intron Organization and Complete Nucleotide Sequence of an HLA Gene", *Proc. Nat'l Acad. Sci. USA* 79: 893–897 (1982).

Geraghty et al., "The HLA Class I Gene Family Includes at Least Six Genes and Twelve Pseudogene and Gene Fragments" *J. Immunology* 149: 1934–1946 (1992).

Blasczyk et al., "Complete subtyping of the HLA–A Locus by sequence–specific amplification followed by direct sequencing or single–strand conformation polymorphism analysis", *Tissue Antigens* 46: 86–95 (1995).

Cereb, N., et al., Tissue Antigens 1995, 45: 1–11.

Summers, C.W., et al., European Journal of Immunogenetics 1993, 20: 201–240.

*Primary Examiner*—Ardin H. Marschel
*Attorney, Agent, or Firm*—Oppedahl & Larson LLP

[57] ABSTRACT

Consensus sequences of introns 1, 2 and 3 from the majority of HLA-A, -B and -C allotypes are identified and used to develop primers located within introns 1 and 3 of the HLA-A, HLA-B and HLA-C genes. These primers are suitable for locus-specific amplification of the entirety of exons 2 and 3, i.e., the portion of these of genes most suitable for use in typing of HLA-A, HLA-B and HLA-C. These primers are also suitable for use as sequencing primers to determine the HLA alleles in sequence-based HLA typing. Thus, the primers can be used for testing a sample to determine the HLA-A, -B or -C type of the sample by treating the tissue sample to obtain nucleic acid polymers suitable for amplification; combining the nucleic acid polymers with a first primer which is complementary to a portion of intron 1 or intron 3 of the HLA gene, and a second primer which is complementary to some other portion of the HLA gene under conditions suitable for amplification to obtain an amplified product; and evaluating the amplified product to determine the allelic type of the HLA-A, HLA-B or HLA-C genes. Preferably, at least one of the amplification primers has a sequence which provides locus-specific amplification.

27 Claims, 45 Drawing Sheets

EXON-INTRON ORGANIZATION OF HLA CLASS I GENES

EXON-INTRON ORGANIZATION OF HLA CLASS I GENES

FIG. 2

HLAA

GTGAGTGCGGGGTCGKGAGGGAAACSGCCTCTGYGGGAGAAGCAASGGGCCCKCCYGCGGGGRCGCARGACCSGGGDAGCCGCGCCKGGASGAGAGGGTCGGKYRGRTCTCA
————10, 11————

GCCWCTSCTCGYCCCCAG

HLAB

GTGAGTGCGGGRTCGGSAGGGAAATGCCCTCTGYVGGGAGGAGMGAGGGACCGCAGGCGGCGCGACCYGRGAGCCGCGCCGGGAGAGAGGGTCKGGCGGGTYTCAG
————23————                                    ————24————
                                               ————25————

CYCCTCCTBRCCCCCAG

HLAC

GTGAGTGCGCRGGTTRGGAGGGAADCGGCCTCTGSGGAGAGAGGARCGAGGKGCCCKCCCCGGCGAGGGCGCAGGACCCGGGGAGCCGCGCAGGGAGGWGGGTCGGCGGGTCTCA
————31————          ————30, 32————                                                ————33————

GCCMCTCCTCKYCCCCAG

Fig. 3
CONSENSUS SEQUENCES OF INTRON 2 WITH AMPLIFICATION PRIMER LOCATIONS

HLA-A
GTGAGTGACCCCCRGCCSGGGGCGCAGTCASGACCYCTCATCCCCACGGACGGGCCRGGTSCRCCCAC

AGTCTCCGGGTCCGAGATCCRCCCCGAAGCCGCGGGACYCCGAGACCCTTGHCCCGGAGAGCCCAGGCGCCTTWACCCGGTTTC

ATTTTCAGTTTAGGCCAAAAATYCCCCCRGTTGGTCGGGGCBGGRCRGGGCTYGGGGACYGGGCTGACCKYGGGGTCSGGGCCAG

HLA-B
GTGAGTGACCCCGGCCYGGGGCGSAGTCACGACTCCCCATCCCCACGKACGGBCCGGGTCGCCCGAGTCTCCGGTCCGAGATCCRMCYCCCTGA

GGCYGSGGGAMCCGCCCAKACCCTCGACCGGMGAGAGCCSCAGGCGCGTTTACCCGGTTTCATTTTCAGTTGAGGCCAAAAATCCCCGCGGGTTGGKCRGGGCG

GGGCGGGGCGGGGGCTCGGGGGACKGKGKGCTGWCCGCGGGGBSKGGKCCAG

HLA-C
GTGAGTGACCCCCRGCCCGGGGCGCAGTCACGGATCCCCCACGGACGGCCCGGGTCGCCCCRAGTCTCSSGTCTGAGATCCACCCCAAGGTGGAT

CTGCGGAACCCGCCAGACCCTCGACCGGAGAGAGCCCYAGTCRCCTTTACCCGGTTTCATTTTCRGTTTAGGCAAAAATCCCCGCSGKTTGGTCGGRCKGG

GGCGGGGCTCGSGGGACKGKGKGYTGASCRCGGGGGGGGCCAG

Fig. 4
CONSENSUS SEQUENCES OF INTRON 3 WITH AMPLIFICATION PRIMER LOCATIONS

HLA-A SEQ ID No.: 3

```
GTACCAGGGCCACRGRGCGCCCTMCCTGATCGCCTRTAGRTCTCCCGGCTGGCCTCCCACAAGGAGGGAGACAWTTGGGAGACCAACACTAGAATATC
       >-----12------<                                            >------13-------<
RCCCTCCCTCTGGTCCTGAGGGAGAGAAMTCCTCCTGGGTTTCCAGATCCTGTACCAGAGAGTGACTCTGAGGTTCCGCCCTGCTCTSTGACWCAATT
   >------14--------<
AAGGGATAAAATCTCTGAMGGARTGACGGDAAGACGATCCCTGAATACTGATGASTGGTTCCCTTTGACACACACMGGCAGSAGCCTTGGGMCCGTG
ACTTTTCCTCTCAGGCCTTGTTCCCTYYTCAGGGAMTAGAATTTTCTCACGGAMTAGAATTTTCCACGGAATAGGAGATTATCCCAGTGCCTGGTCGTCCAGCTGGTTCTGTGCTC
CCAGAAGTCGCTGTTCCCTYYTCAGGGAMTAGAATTTTCTCACGGAMTAGAATTTTCCACGGAATAGGAGATTATCCCAGTGCCTGGTCGTCCAGCTGGTTCTGTGCTC
YCTTCCCCATCCCRGTGTSCTGTCCATTCTCAAGATRGSCACATGYRTGCTGGWGGAGTGTCCCATKACAGATRCMMAATGCCTGMATKWTCTGACTC
TTCCYGWCAG
```

HLA-B SEQ ID No.: 6

```
GTACCAGGGGCAGTGGGGAGCCTBCCCCATCTCCTATAGGTCGSCGGGGATGGSCTCCMACGAGAAGARGAGGAAAATGGGATCAGCGCTAGAATGTC
     >------29-------<          >-->------26/27------<
GCCCTCCCTTGAATGGAGAATGGCATGAGTTTTCCCTGAGTTTCCTCTGAGGGCCCCCCCTCTCTCTAGGACAATTARGGRATGACGTCTCTGAGGAA
  >-------28--------<
ATGGAGGGGAAGWCAGYCCCTAGRATASTGATCAGGGGTCCYCTTTGACCCTGCAGCAGCCTTGGGACNCCRTGACCTTTCYTCTCAGRCCTTGTTCTC
TGCCTCACACTCAGTGTGTTGGGGCTCTGATTCCAGYACTTCTGAGTCACTTTACCTCCACTCAGATCRGGAGCAGAAGTCYCTGTTCCCCGCTCAGA
GACTCGAACTTTCCAATGAAGATAGGAGATTATCCCAGTGCCTGGTCTGTGCYCCCTMCCACMCCAGGTGTCCTGYCCA
TTCTCAGKCTGGTCACATGGGGTGGTCCTAGGGTGTSCCATGARAGATGCMAAGCGCCTGWAWTTTTCTGACTCTTCCCATCAG
```

HLA-C SEQ ID No.: 9

```
GTACCAGGGGCAGTGGGGAGCCTTCCCCATCTCCTAGATCTCCCGGSATGCCCTCCCACGAGGAGGGAGGAAAATGGGATCAGCGCTRGAATATC
     >------29-------<                              >-----34-----<
GCCCTCCCCTTGAATGGAGAATGGSATGAGTTTTCCYGAGTTTCYTCTGARGGCCCCCSTCGTCTGCTCTCTAGGACAATTAAGGATGAAGTCYYTGAGGAAA
  >------35-------<
TGGAGGGGAAGACAGTCCCTRGAATACTGATCAGGGGTCYCCCTTTGACCACTGCRGCAGCTGTGGTCAGGCTGCTGACCTTTCTCTCAGG
                                                      >------36-------<
CCTTGTTCTCTGCCTCAYRYTCAYRYTCAATGTGTYTRAAGGTTTGATTCCAGCTTTTCTGAGTYCTKCRGCCTCCACTCAGGTCAGGACCAGAAGTCGCTGTTC
                       >------37-------<
CTCCCTCAGAGACTAGAACTTTCCAAWGAATAGGAGATTATCCCAGGTSCCTGTCCAGGTCAGGGTTCTGTGCCGCGGCTGGCGTCTGGGTTCTGTGCCSCCTTCCCYACCCCAGG
  >-------38--------<
TGTCCTGTCCRTTCTCAGGATRGTCACATGGSCRCTGYTGGAGTGTCSCAAGAGAGAWRCAAAGTGTCTGAATTTTCTGACTCTTCCCGTCAG
```

Fig. 5A (part 1)
Part I of HLA INTRON 1 Sequence

```
                 3    6    9    12   15   18   21   24   27   30   33   36   39   42   45   48   51   54   57   60   63   66
                 |----|----|----|----|----|----|----|----|----|----|----|----|----|----|----|----|----|----|----|----|----|----|
A2Genbank        GTGAGTGCGGGGTCGGGGGAGGGAAAACGGGCCCTCTGTGGGGAGAAGCAACGGG.CCGCCTGGCGGGGCG
A2.msk           GTGAGTGCGGGGTCGGGGGAGGGAAAACGGGCCCTCTGTGGGGAGAAGCAACGGGCCCGCCTGGCGGGGCG
A1     (2)      ---------------------------------C------------G----------T-----------
A3     (1)      ----------------------------------------------G----------T-----------
A30    (1)      ---------------------------------C------------G----------T-----------
A11    (1)      ----------------------------------------------G----------T-----------
A24    (4)      ---------------------------------C------------G----------------------
A25    (2)      ---------------------------------C------------G----------------------
A66 TEM         ----------------------------------------------------------------------
A26 MGAR        ---------------T...-------------C------------G------C---------------
A28    (1)      ---------------T...-------------------------------G------C---------------
A32    (1)      ---------------T...-------------C-------------G------C---------------
A29    (1)      -.A-------------T...-------------C------------G------C---------------
A31    (1)      ---------------T...-------------C------------G------C---------------A---
A33    (2)      ---------------T...-------------C------------G------C---------------

B7     (2)      --------------------------T----------G---G--A---A---
B8     (4)      -.A-----------C-----------T----------G---G--A---A---
B13    (1)      --------------C-----------T----------G---G--A---A---
B18    (2)      --------------C-----------T----CC----G---G--A---A---
B27    (1)      --------------------------T----CC----G---G--A---A---
B35    (1)      --------------------------T----------G---G--A---A---
B37    (1)      --------------C-----------T----------G---G--A---A---
B38    (1)      --------------------------T----------G---G--A---A---
B42    (2)      --------------C-----------T----------G-AG-G--A---A---
B44    (1)      --------------C-----------T----CC----G---G--A---A---
B45    (3)      --------------------------T----------G---G--A---A---
B46    (1)      --------------------------T----------G---G--A---A---
B50    (1)      --------------------------T----------G---G--A---A---
B51    (3)      --------------C-----------T----------G---G--A---A---
B52    (2)      --------------C-----------T----------G---G--A---A---
B54    (1)      --------------------------T----------G---G--A---A---
B57    (1)      --------------------------T----A-----G---G--A---A---
B58Genbank      --------------------------T----------G-G-G--A-A---A---
B60    (1)      --------------------------T----------G---G--A---A---
B61    (1)      --------------------------T----------G---G--A---A---
B62    (1)      --------------------------T----CC----G---G--A---A---
B64    (1)      --------------------------T----------G---G--A---A---
B65    (1)      --------------------------T----CC----G---G--A---A---
```

Fig. 5A (part 2)
Part I of HLA INTRON 1 Sequence

```
             3       6   9    12    18    24    30    36    42    48    54    60    66
             |-------|---|----|-----|-----|-----|-----|-----|-----|-----|-----|-----|
A2Genbank    GTGAGTGCGGGGTCGGGGTGGGGAGGAAACGGCCTCTGTGGGAGAGCAACGGG..CCGCCTGGCGGGGCG
A2.msk       GTGAGTGCGGGGTCGGGGTGGGGAGGAAACGGCCTCTGTGGGAGAGCAACGGGccCCGCCTGGCGGGGCG Cw5   (1)    ----------------T----------------------C---A---G--G---------C-----A--
Cw8   (4)    --------A-------T----------------------C---A---G--G---------C-----A--
Cw2   (2)    --------A-------T----------------------C---A---G--G---------C-----A--
Cw3   (2)    ----------------T-------T--------------C---A---G--G---------C-----A--
Cw7   (1)    ----------------T-------G--------------C---A---G--G------T--C-----A--
Cw6   (1)    ----------------T----------------------C---A---G--G---------C-----A--
Cw1   (2)    ----------------T----------------------C---A-G-A-G-G-T------C-----A--
Cw12  (2)    ----------------T----------------------C---A---G--G---------C-----A--
Cw16  (1)    ----------------T----------------------C---A---G--G---------C-----A--
Cw17  (1)    ----------------T----------------------C---A---G--G---------C-----A--
Cw4   (1)    ----------------T----------------------G---A---G--G---------C-----A--
Cw14  (1)    ----------------TA---------------------C---A---G--G---------C-----A--

E     (3)    ----------------------CA--T--------ACC-----T--AG-G------G---C--------
F     (2*)   ----------------------A---A--------------CC-T--TG-G------------C--T--
G     (1*)   --------A-------T-C------C---------------C-G---GG-G------C----C------
H     (1)    ----------------A----------T-----------CC-T--G--AA-T--A---------C----
J     (2)    ----------------A----------T-----------C---G---T-G----------------T--
K     (1)    ------A---------C----------G-----------C---G---T-G----.GCA-T---------
L Genbank    ----------------TA----------------------------GT---T---------
```

* Consensus of several clones.

Fig. 5A (part 3)
Part II of HLA INTRON 1 Sequence

Fig. 5A (part 4)
Part II of HLA INTRON 1 Sequence

```
              72        78        84        90        96       102       108       114       120       129
              |---------|---------|---------|---------|---------|---------|---------|---------|---------|
(A2Genbank)   CAGGACCCGGAAGCCGCGCCGGAGGAGGGTCGGGCGGGTCTCAGCCACTCCTCGTCCCCAG
A2.msk        CAGGACCCGGAAGCCGCGCCGGAGGAGGGTCGGGCGGGTCTCAGCCACTCCTCGTCCCCAG Cw5   (1)     -------------G-----------A-----------------------C-----------C---
Cw8   (4)     -------------G-----------A-----------------------C-----------C---
Cw2   (2)     -------------G-----------A-----------------------C-----------TC--
Cw3   (2)     -------------G-----------A-----------------------C-----------C---
Cw7   (1)     -------------G-----------A--------T--------------C-----------C---
Cw6   (1)     -------------G-----------A--------T--------------C-----------C---
Cw1   (2)     -------------G-----------A-----------------------C-----------C---
Cw12  (2)     -------------G-----------A-----------------------C-----------C---
Cw16  (1)     -------------G-----------A-----------------------C-----------C---
Cw17  (1)     -------------G-----------A-----------------------C-----------C---
Cw4   (1)     -------------G-----------A-----------------------------------C---
Cw14  (1)     -------------G-----------A-----------------------C-----------C---

E  (3)        A-----T----G---------------------C-----------C-A------------C---
F  (2)        -----T-A---G----------------------------T--------------------C---
G  (1)        -----T-----C----------------------------------A---------TC----CT--
H  (1)        --------A--G-----------A------------------------------TC-----C---
J  (2)        -----------G-----------A--------AT-----------------------C---C---
K  (1)        -----------G-A---------AA--------------------------------T---C---
L  Genbank    -.---------G-----------------------------------------T-----C-T---
```

\* Consensus of several clones.

Fig. 5B (part 1)
Part I of HLA Intron 2

Fig. 5B (part 2)
Part I of HLA Intron 2

Fig. 5B (part 3)
Part II of HLA Intron 2

```
              84        90        96       102       108       114       120       126       132
              |----|----|----|----|----|----|----|----|----|----|----|----|----|----|----|----|
A2.msk&gb(3)  GTCTCCGGGTCCGAGATCCGCCCC..GAAGCC..GCGGGACCCC..GAGA
A1       (1)  ------------------------A---------------------------
A3       (2)  ------------------------A---------------------------
A30      (2)  ------------------------A---------------------------
A11      (1)  ------------------------A---------------------------
A24      (5)  ------------------------A---------------------------
A25      (2)  ----------------------------------------------------
A66 TEM       ----------------------------------------------------
A26 MGAR      ----------------------------------------------------
A28      (1)  ------------------------A---------------------------
A32      (1)  ----------------------------------------------------
A29      (2)  ------------------------A---------------------------
A31      (2)  ------------------------A---------------------------
A33      (2)  ------------------------A---------------------------
                                      @ Gorilla @
Rok-F6   (2a) ------------------------A---------------------------
B7       (1)  -------------------------T-CCT-G--------------------
B8       (4)  ---------------------------CCT-G--------------------GCCC----
B13      (1)  -------------------------T-CCT-G--------------------GCCC----
B18      (1)  ---------------------------CCT-G--------------------GCCC----
B27      (1)  -------------------------T-C---G--------------------GCCC----
B35      (4)  ---------------------------CCT-G--------------------GCCC----
B37      (1)  -------------------------T-CCT-G--------------------GCCC----
B38      (1)  -------------------------T-CCT-G--------------------GCCC----
B42      (1)  -------------------------T-CCT-G--------------------GCCC----
B44      (1)  ---------------------------CCT-G--------------------GCCC----
B45      (3)  ---------------------------C---G--------------------GCCC----
B46      (1)  ---------------------------CCT-G-------------G------GCCC-A--
B50      (1)  ---------------------------CCT-G--------------------GCCC----
B51      (1)  -------------------------T-CCT-G--------------------GCCC----
B52      (1)  -------------------------T-CCT-G--------------------GCCC----
B54      (1)  -------------------------T-CCT-G--------------------GCCC----
B57      (1)  -------------------------T-CCT-G--------------------GCCC----
B58 Genbank   -------------------------A-CCT-G--------------------GCCC----
B60      (1)  ------------------------A--CCT-G--------------------GCCC----
B61      (1)  ---------------------------CCT-G-------------T---A--GCCC----
B15(62)  (3)  ---------------------------CCT-G--------------------GCCC----
B64      (1)  -------------------------T-CCT-G--------------------GCCC----
B65 Genbank   -------------------------T-CCT-G--------------------GCCC----
```

Fig. 5B (part 4)
Part II of HLA Intron 2

Fig. 5C (part 1)
Part II of HLA Intron 2

Fig. 5C (part 2)
Part II of HLA Intron 2

```
                 135     141     147     153     159     165     171     177     183     189     195     201
                 |-------|-------|-------|-------|-------|-------|-------|-------|-------|-------|-------|--|
A2.msk&gb(3)     CCCTTGCCCCGGGAGAGAGGCCCAGGCGCCTTTACCCCGGTTTCATTTCAGTTTAGGCCAAAATCCCCC Puti-1, 3, 4     --T-C-A--G-A-------C-----------------------------------G-------------G--
Lena 6/24        ----C-A--G-C-------C-----G---------------------------------G---------G--

Rok consensus                               @ Gorilla @
Cw1 (3)          ----C-A--G-C-------C---G-------------------------------G-------------G--
Cw2 (2)          ----C-A--G-A-------T-A-----------------------------------------------G--
Cw3 (3)          ----C-A--G-A-------T-A-----------------------------------------------G--
Cw4 (1)          ----C-A--G-A-------T-A-----------------------------------------------G--
Cw5 (2)          ----C-A--G-G-------T-A-----------------------------------------------G--
Cw6 (2)          ----C-A--G-A-------T-A-----------------------------------------------G--
Cw7 (1)          ----C-A--G-A-------T-A-----------------------------------------------G--
Cw8 (1)          ----C-A--G-A-------T-A-----------------------------------------------G--
Cw12 (1)         ----C-A--G-A-------T-A-----------------------------G-----------------G--
Cw14 (1)         ----C-A--G-A-------T-A-----------------------------------------------G--
Cw16 (1)         ----C-G--G-A-------T-A-----------------------------------------------G--
Cw17 (1)         ----C-A--G-A-------T-------------------------------------------------G--

@ Chimpanzee @
Tank (CG)        ----C-A--G-A-------C---T-A-------------------------------------G-----G--
E (3)            ----A-A--G---------T---T-------------------.T----------------G-A-----A--
F (1)            ----CCA------------T-------GA-G--.-----------------------------G-----G--
G (2)            ----CTA--T---------AC----------..........-----------------------..---G--
H CONSENSUS      -----A---T----------------------T---C---------------------------.--T-G--
J CONSENSUS      T---C-A------------C----------T-----C----------------G--------------G--
K CONSENSUS      T---C-A------------------------A------------------------------------G--
LHLA92 Genbank   ----C-A--A----AGAAA-TC--GCG-C--TA--C-G--T-A----------------------.---G--
```

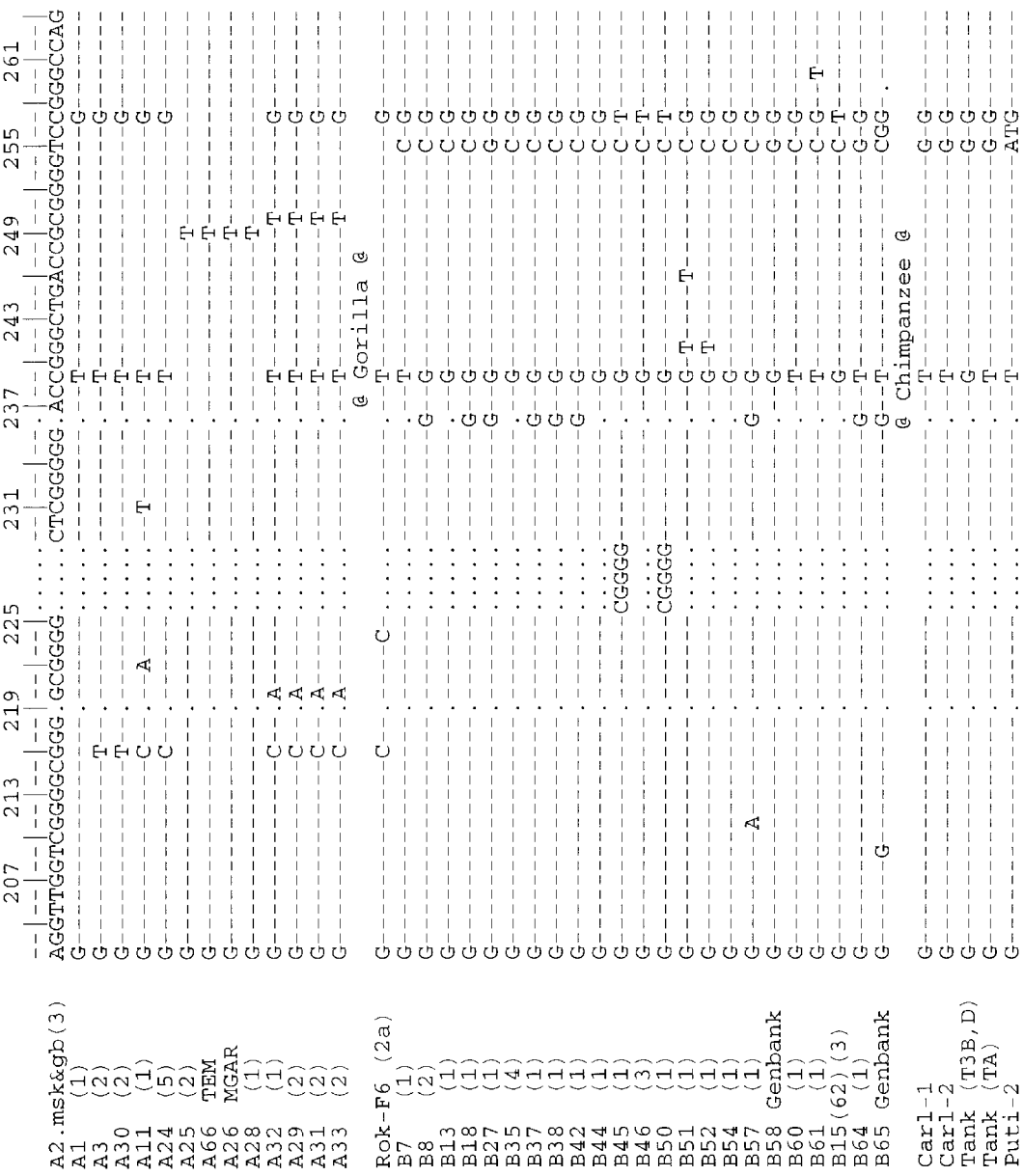
Fig. 5C (part 3)
Part II of HLA Intron 2

Fig. 5C (part 4)
Part II of HLA Intron 2

```
                  207       213       219       225       231       237       243       249       255       261
                  |---------|---------|---------|---------|----:----:|---------|---------|---------|---------|---
A2.msk&gb(3)      AGGTTGGTCGGGGCGGG.GCGGGG..........CTCGGGGG.ACCGGGCTGACCGCGGGGTCCGGGCCAG Puti-1,3,4        G--------------------------------------C---------T-------------TG-G-------
Lena 6/24         G----------------------------------------------T---------G-G----------T---

Rok consensus     G------------------------------                  @ Gorilla @
Cw1 (3)           C----A-T-G-----------------------                 -G-----------A----G-G-------
Cw2 (2)           G------T-G-----------------------                 -G-----------A----G-G-------
Cw3 (3)           G------.-G-----------------------                 -G----------------G-G-------
Cw4 (1)           G----A-T-G-----------------------                 -.-----------A----G-G-------
Cw5 (2)           G------T-G-----------------------                 -G-----------A----G-G-------
Cw6 (2)           G------T-G-----------------------                 -G-----------A----G-G-------
Cw7 (1)           G------T-G-----------------------                 -T----------------G-G-------
Cw8 (1)           G-T----T-G-----------------------                 -G-----------A----G-G-------
Cw12 (1)          G-T----A-T-G---------------------                 -G----------------G-G-------
Cw14 (1)          G------T-G-----------------------      -C-        -G-T-T--------A----G-G-------
Cw16 (1)          G------T-G-----------------------                 -G-----------A----G-G-------
Cw17 (1)          G------T-G-----------------------                 -G----------------G-G-------

@ Chimpanzee @
Tank (CG)         G--G---T-G-----------------------                 -G------------A---G-G-------
E (3)             --G-C-A--G-----------------------   -T-T-.G-G--A-----.G--------
F (1)             G--G--A--G-----------------------   -A-CT-.G-G-----T---TAA--.G------T-
G (2)             .-G--C---AG---A------------------   -T----.G-G-----T-----A---GTG-------
H CONSENSUS       G------A--------------------------  -T----.G-G---------------G----------
J CONSENSUS       ----C-A----C-GC-A----------------   -T----.G-G-----T--AA-T----------
K CONSENSUS       G-----------G---------------------  -T----.G-G---A-----------G-G-------
LHLA92 Genbank    G----------A----------------------  -T-T.T-G------G-------G-GA-----T
```

FIG. 5D (part 1)
Part I of HLA Intron 3

FIG. 5D (part 2)
Part I of HLA Intron 3

FIG. 5D (part 3)
Part II of HLA Intron 3

```
                        96       102      108      114      120      126
                        |--------|--------|--------|--------|--------|----
A2msk & Genbank         AGAATATCGC.CCTCCCTCTGGTCCTGAGGGAGAGGAAT
A1       (1)            ----------.-A----.--------.--------.--------.----
A3       (1)            ----------.-A----.--------.--------.--------.---C
A11      (1)            ----------.-A----.--------.--------.--------.----
A24      (2)            ----------.------.--------.--------.--------.----
A25      (1)            ----------.------.--------.--------.--------.----
A26      (1)            ----------.------.--------.--------.--------.----
A66      (1)            ----------.------.--------.--------.--------.----
A28      (1)            ----------.------.--------.--------.--------.----
A29      (1)            ----------.-A----.--------.--------.--------.----
A30      (1)            ----------.-A----.--------.--------.--------.----
A31      (2)            ----------.-A----.--------.--------.--------.----
A32      (1)            ----------.------.--------.--------.--------.----
A33      (2)            ----------.-A----.--------.--------.--------.----
B7       (2)            -------G--.------.--------.--------.-AT-----.----
B8       (1)            -------G--.------.--------.--------.-AT-----.----
B13      (1)            -------G--.------.--------.--------.-AT-----.----
B64      (1)            -------G--.------.--------.--------.-AT-----.----
B15(62)(1)              -------G--.------.--------.--------.-AT-----.----
B18      (1)            -------G--.------.--------.--------.-AT-----.----
B27 Genbank             -------G--.------.--------.--------.-AT-----.----
B35      (1)            -------G--.------.--------.--------.-AT-----.----
B37      (1)            -------G--.------.--------.--------.-AT-----.----
B38      (1)            -------G--.------.--------.--------.-AT-----.----
B42      (1)            -------G--.------.--------.--------.-AT-----.----
B44      (1)            -------G--.------.--------.--------.-AT-----.----
B45      (2)            -------G--.------.--------.--------.-AT-----.----
B46      (1)            -------G--.------.--------.--------.-AT-----.----
B50      (1)            -------G--.------.--------.--------.-AT-----.----
B51      (1)            -------G--.------.--------.--------.-AT-----.----
B52      (1)            -------G--.------.--------.--------.-AT-----.----
B54      (1)            -------G--.------.--------.--------.-AT-----.----
B57      (1)            -------G--.------.--------.--------.-AT-----.----
B58 Genbank             -------G--.------.--------.--------.-AT-----.----
B60      (1)            -------G--.------.--------.--------.-AT-----.----
B61      (1)            -------G--.------.--------.--------.-AT-----.----
B65      (1)            -------G--.------.--------.--------.-AT-----.----
```

FIG. 5D (part 4)
Part II of HLA Intron 3

```
                              96        102       108       114       120       126
                              |----|----|----|----|----|----|----|----|----|----|----|----|----|----|----|--|
A2msk & Genbank               AGAATATCGC.CCTCCCTCTGGTCCTGAGGGAGGAGGAAT
Cw1         (1)               ----------.-------------------------AT-
Cw2         (1)               ----------.-------------------------AT-
Cw2 Genbank                   ----------.------------GA-----------AT-
Cw3         (1)               ----------.-------------------------AT-
Cw4         (1)               ----------.-------------------------AT-
Cw5         (1)               -----G----.-------------------------AT-
Cw6         (2)               ----------.-------------------------AT-
Cw7         (2)               -----G----.-------------------------AT-
Cw8         (1)               -----G----.-------------------------AT-
Cw12        (2)               ----------.-------------------------AT-
Cw14        (1)               ----------.-------------------------AT-
Cw16        (1)               ----------.-------------------------AT-
Cw17        (1)               ----------.-------------------------AT- E Genbank                     ----C-A-T-----------TG-A---AG---A-G---CTG-
F           (1)               --G-------------------------TAG---A-----
G           (1)               ----------------------------------------
H           (1)               --T---------------------T---------A-----
J.consen.Genbank              --------------CT-----C------------------
K.HLA70 Genbank               --G---T.----T---------------------------
L           (1)               -----------------A------------AT-G---A--
```

FIG. 5E (part 1)
Part II of HLA Intron 3

FIG. 5E (part 2)
Part II of HLA Intron 3

```
                         132       138       144       150       156       162       168       174       180    186
                         |----|----|----|----|----|----|----|----|----|----|----|----|----|----|----|----|----|----|--|
A2msk & Genbank          CCTCCTGGGTTT.CCAGATCCTGTACCAGAGAGTGACTCT...GAGGTTCCGCCCCTGCTCTC
Cw1      (1)             .GGGA--A----T--T-G.--T.............-------GC---C--T-----------
Cw2      (1)             .GGGA--A----T--T-G.--T.............-------GC---C--T-----------
Cw2 Genbank              .GGGA--A----T--T-G.--T.............-------GC---C--T-----------
Cw3      (1)             .GGGA--A----T--T-G.--T.............-------GC---C--T-----------
Cw4      (1)             .GGGA--A----T--T-G.--T.............-------GC---C--T-----------
Cw5      (1)             .GGGA--A----T--T-G.--T.............-------GC---C--T-----------
Cw6      (2)             .GGGA--A----T--T-G.--T.............-------GC---C--T-----------
Cw7      (2)             .GG-A--A----T--T-G.--T.............-------GC---C--T-----------
Cw8      (1)             .GGGA--A----T--T-G.--T------T------.-A-GC---C--T-----------
Cw12     (2)             .GGGA--A----T--T-G.--T.............-------GC---C--T-----------
Cw14     (1)             .GGGA--A----T--T-G.--T.............-------GC---C--T-----------
Cw16     (1)             .GGGA--A----T--C-G.--T.............-------GC---C--T-----------
Cw17     (1)             .GGGA--A----T--T-G.--T.............-------GC---CGT-----------

E   Genbank              --AC-TGA---ACAGG------A-----C----------CTTA-A-GG--AGA-CT-----

F        (1)             --T------C---T-G------G----------T-G------AG----------------

G        (1)             ........---------------.........-T............---GC---T----------

H        (1)             -------C-------------G--------................-----G--------------

J.consen. Genbank        ..................................T---T..............-GC--A------T K.HLA70Genbank           .......................-A-----------G--T------

L        (1)             ..........................-A....-AGC--A------
```

FIG. 5E (part 3)
Part II of HLA Intron 3

```
                           192        198      204       210       216       222       228       234
                            |----|----|----|----|----|----|----|----|----|----|----|----|----|----|
A2msk& Genbank           ...TGACACAATTAAGGGATAAAATCTCTGAAGGAATGACGGG.AAGACGATCCCT
A1       (1)             ..................................................................
A3       (1)             ..................................................................
A11      (1)             .....................................G............................
A24      (2)             .....................................G............................
A25      (1)             .....................................G............................
A26      (1)             ................................C...................................
A66      (1)             ....................................G-A.............................
A28      (1)             ....................................G...............................
A29      (1)             ..........................T.........................................
A30      (1)             ......................................................T..............
A31      (2)             .....................................................................
A32      (1)             .....................................G..............................
A33      (2)             .....................................................................

B7   (2)                 ...AG.----A--G-CG--------G-A----GA----G------AG---
B8   (1)                 ...AG.-------G-CG--------G-A----GA----G------AG---
B13  (1)                 ...AGG-------G-CG--------G-A----GA----G------AG---
B64  (1)                 ...AGG-------G-CG--------G-A----TA----G------AG---
B15(62)(1)               ...AGG----G--G-CG--------G-A----GA----G------AG---
B18  (1)                 ...AGG-------G-CG--------G-A----CG----G------AG---
B27 Genbank              ...AGG-------G-CG--------G-A----GA----G------AG---
B35  (1)                 ...AGG-------G-CG--------G-A----GA----G------AG---
B37  (1)                 ...AGG-------G-CG--------G-A----GA----G------AG---
B38  (1)                 ...AGG-------G-CG--------G-A----GA----G------AG---
B42  (1)                 ...AG.-------G-CG--------G-A----GA----G------AG---
B44  (1)                 ...AGG-------G-CG--------G-A----GA----G------AG---
B45  (1)                 ...AGG-------G-CG--------G-A----GA----G------AG---
B46  (2)                 ...AGG-------G-CG--------G-A----GA----G------AG---
B50  (1)                 ...AGG-------G-CG--------G-A----GA----G------AG---
B51  (1)                 ...AGG-------G-CG--------G-A----GA----G---T--AG---
B52  (1)                 ...AGG-------G-CG--------G-A----GA----G------AG---
B54  (1)                 ...AGG-------G-CG--------G-A----GA----G------AG---
B57  (1)                 ...AGG-------G-CG--------G-A----GA----G------AG---
B58 Genbank              ...AGG----A--G-CG--------G-A----GA----G------AG---
B60  (1)                 ...AGG-------G-CG--------G-A----GA----G------AG---
B61  (1)                 ...AGG-------G-CG--------G-A----GA----G------AGC--
B65  (1)                 ...AGG-------G-CG--------G-A----GA----G------AG---
```

FIG. 5E (part 4)
Part II of HLA Intron 3

```
                        192       198       204       210       216       222       228       234
                        -|---|---|---|---|---|---|---|---|---|---|---|---|---|---|-
                     ..TGACACAATTAAGGGATAAAAATCTCTGAAGGAATGACGGG.AAGACGATCCCT
A2msk& Genbank
Cw1    (1)           ..-AGG-----------------G--A---CT--G-----GA-----G------AG---
Cw2    (1)           ..-AGG-----------------G--A---CT--G-----GA-----G------AG---
Cw2    Genbank       ..-AGG-----------------G--A---CT--G-----GA-----G------AG---
Cw3    (1)           ..-AGG-----------------G--A---CT--G-----GA-----G------AG---
Cw4    (1)           ..-AGG-----------------G--A---CT--G-----GA-----G------AG---
Cw5    (1)           ..-AGG-----------------G--A---CT--G-----GA-----G------AG---
Cw6    (2)           ..-AGG-----------------G--A---CT--G-----GA-----G------AG---
Cw7    (2)           ..-AGG-----------------G--A---CT--G-----GA-----G------AG---
Cw8    (1)           ..-AGG-----------------G--A---CT--G-----GA-----G------AG---
Cw12   (2)           ..-AGG-----------------G--A---CT--G-----GA-----G------AG---
Cw14   (1)           ..-AGG-----------------G--A---CT--G-----GA-----G------AG---
Cw16   (1)           ..-AGG-----------------G--A---C---G-----GA-----G------AG---
Cw17   (1)           ..-AGG-----------------G--A---CT--G-----GA-----G------AG---

E   Genbank          ..A-GGG----------A--CT-G-----GCTG-AG---T-CATCCTTCA---.....

F   (1)              ..-TGG-----------G-----GGAG----.........---AG---

G   (1)              ..--GG-----------G-----G-------G---GA-----G-----A---

H   (1)              .................----G-----G---GA-----A-----A---

J.consen. Genbank    CC---GG----------G-----G-------G---GA-----G-----A---

K.HLA70Genbank       ..---------T-----------G-A-----A-----A-...A-----A---

L   (1)              ..--GG-----------G--C--------.......---A---------AG---
```

FIG. 5F (part 1)
Part III of HLA Intron 3

```
                    243       249       255       261       267       273       279       285       291       297
                    -|---|---|---|---|---|---|---|---|---|---|---|---|---|---|---|---|---|---|
        A2msk&      CGAATACTGATGAGTGGTTCCCTTTGAC.AC...ACACAGGCAGCAGCCTTGGGC..CC.G.TGACT
        Genbank
A1      (1)         ------------------------------------------------------------------
A3      (1)         ------------------------------------------------------------------
A11     (1)         ------------------------------------------------------------------
A24     (2)         -----------C------------------------------------------------------
A25     (1)         ------------------------------------------------------------------
A26     (1)         ---------------------------------------G--------------------------
A66     (1)         ----------------------------------A-------------------------------
A28     (1)         ------------------------------------------------------------------
A29     (1)         ------------------------------------------------------------------
A30     (1)         ------------------------------------------------------------------
A31     (2)         ------------------------------------------------------------------
A32     (1)         ------------------------------------------------------------------
A33     (2)         ------------------------------------------------------------------
B7      (2)         A-----------C---G---C-------------C-------T-----------------A.A----
B8      (1)         A-----------C---G---C-------------C-------T-----------------A.A----
B13     (1)         A-----------C---G---C-------------C-------T-----------------A.A----
B64     (1)         A-----------C---G---C-------------C-------T-----------------A.A.-A-
B15(62) (1)         A-G---G-----C---G---C-------------C-------T-----------------A.A----
B18     (1)         A-----------C---G---C-------------C-------T-----------------A.A.-A-
B27 Genbank A       A-----------C---G---C-------------C-------T-----------------A.A----
B35     (1)         A-----------C---G---C-------------C-------T-----------------A.A----
B37     (1)         A-----------C---G---C-------------C-------T-----------------A.A----
B38     (1)         A-----------C---G---C-------------C-------T-----------------A.A----
B42     (1)         A-----------C---G---C-------------C-------T-----------------A.A.-A-
B44     (1)         A-----------C---G---C-------------C-------T-----------------A.A----
B45     (2)         A-----------C---G---C-------------C-------T-----------------A.A----
B46     (1)         A-----------C---G---C-------------C-------T-----------------A.A----
B50     (1)         A-----------C---G---C-------------C-------T-----------------A.A----
B51     (1)         A-----------C---G---C-------------C-------T-----------------A.A----
B52     (1)         A-----------C---G---C-------------C-------T-----------------A.A----
B54     (1)         A-----------C---G---C-------T-----C-------T-----------------A.A----
B57     (1)         A-----------C---G---C-------------C-------T-----------------A.A----
B58 Genbank A       A-----------C---G---C-------------C-------T-----------------A.A----
B60     (1)         A-----------C---G---C-------------C-------T-----------------A.A----
B61     (1)         A-----------C---G---C-------------C-------T-----------------A.A----
B65     (1)         A-----------C---G---C-------------C-------T-----------------A.A.-A-
```

FIG. 5F (part 2)
Part III of HLA Intron 3

```
                         243       249       255       261       267       273       279       285       291       297
                         |----|----|----|----|----|----|----|----|----|----|----|----|----|----|----|----|----|----|----|
A2msk&          CGAATACTGATGAGTGGTTCCCTTTGAC.AC....AC ACAGGCAGCAGCCTTGGGC..CC.G.TGACT
   Genbank
Cw1     (1)     G--------C--G-----------C-----TTTG--CACT-------TG---T-AGG-T-C-------C
Cw2     (1)     G--------C--G-----------C-----TTTG--CACT-------TG---T-AGG-T-C-------C
Cw2 Genbank(1)  G--------C--G-----------C-----TTTG--CACT-------TG---T-AGG-T-C-------C
Cw3     (1)     A--------C--G-----------C-----TTTG--CACT-------TG---T-AGG-T-C-------C
Cw4     (1)     G--------C--G-----------C-----TTTG--CACT-------TG---T-AGG-T-C-------C
Cw5     (1)     G--------C--G-----------CT----TTTG--CACT-------TG---T-AGG-T-C-------C
Cw6     (2)     A--------C--G-----------C-----TTTG--CACT-------TG---T-AGG-T-C-------C
Cw7     (2)     G--------C--G-----------C-----TTTG--CACT-------TG---T-AGG-T-C-------C
Cw8     (1)     G--------C--G-----------C-----TTTG--CACT-------TG---T-AGG-T-C-------C
Cw12    (2)     G--------C--G-----------C-----TTTG--CACT-------TG---T-AGG-T-C-------C
Cw14    (1)     A--------C--G-----------C-----TTTG--CACT-------TG---T-AGG-T-C-------C
Cw16    (1)     G--------C--G-----------C-----TTTG--CACT--G----TG---T-AGG-T-C-------C
Cw17    (1)     G--------C--G-----------C-----TTTG--CACT-------TG---T-AGG-T-C-------C
E Genbank       .....----CA----T------.T----.C--GTATT--G-AT-AC---G..GA...........
F       (1)     ........----C---------GCC.TCC.-------------------C---------.........
G       (1)     G---CC-C-G-----------C------------T---------.T---.-A---A---.........
H       (1)     G-----------------------C--------------------------C----.........
J.consen.       G-----------G-----------C------------------------A--.-A----A--.........
   Genbank
K.HLA70 Genbank G-----------G-----------------------------------------------C--.T---
L       (1)     G---CC.----------------------------------T-A-A-----A------.A.G-..
```

FIG. 5F (part 3)
Part III of HLA Intron 3

```
                  303         309         315         321         327         333         339         345         351         357
                  --|----|----|----|----|----|----|----|----|----|----|----|----|----|----|----|----|----|----|
A2msk& Genbank    TTTCCTCTCAGGCCTTGTTCTCTGCTTCACACTCAATGTGTGTGGGGGTCTGAGTCCAGCACT
A1       (1)      ---------------------------------------------------------------
A3       (1)      ---------------------------------------------------------------
A11      (1)      ---------------------------------------------------------------
A24      (2)      ---------------------------------------------------------------
A25      (1)      ---------------------------------------------------------------
A26      (1)      ---------------------------------------------------------------
A66      (1)      ---------------------------------------------------------------
A28      (1)      ---------------------------------------------------------------
A29      (1)      ---------------------------------------------------------------
A30      (1)      ---------------------------------------------------------------
A31      (2)      ---------------------------------------------------------------
A32      (1)      ---------------------------------------------------------------
A33      (2)      ---------------------------------------------------------------
B7       (2)      -------------------------C---------G----T------C-----T--------
B8       (1)      -------------------------C---------G----T------C-----T--------
B13      (1)      -------------------------C---------G----T------C-----T--------
B64      (1)      ----T--------------------C---------G----T------C-----T--------
B15(62)  (1)      -------------------------C---------G----T------C-----T--------
B18      (1)      -------------------------C---------G----T------C-----T--------
B27 Genbank       -------------------------C---------G----T------C-----T--------
B35      (1)      -------------------------C---------G----T------C-----T--------
B37      (1)      -------------------------C---------G----T------C-----T--------
B38      (1)      -------------------------C---------G----T------C-----T--------
B42      (1)      -------------------------C---------G----T------C-----T--------
B44      (1)      -------------------------C---------G----T------C-----T--------
B45      (1)      -------------------------C---------G----T------C-----T--------
B46      (2)      -------------------------C---------G----T------C-----T--------
B50      (1)      -------------------------C---------G----T------C-----T--------
B51      (1)      -------------------------C---------G----T------C-----T--------
B52      (1)      -------------------------C---------G----T------C-----T--------
B54      (1)      ----------A--------------C---------G----T------C-----T--------
B57      (1)      -------------------------C---------G----T------C-----T--------
B58 Genbank       -------------------------C---------G----T------C-----T--------
B60      (1)      -------------------------C---------G----T------C-----T--------
B61      (1)      ----T--------------------C---------G----T------C-----T--------
B65      (1)      -------------------------C---------G----T------C-----T-----T--
```

FIG. 5F (part 4)
Part III of HLA Intron 3

| | 303 | 309 | 315 | 321 | 327 | 333 | 339 | 345 | 351 | 357 |
|---|---|---|---|---|---|---|---|---|---|---|
| A2msk& Genbank | TTTCCTCTCTCAGGCCCTTGTTCTTCTGCTTCACACTCAATGTGTGTGGGGTCTGAGTCCAGCACT |
| Cw1 (1) | | | | | --C-- | --G-- | --T-- | --AA-- | --T-- | --TT-- |
| Cw2 Genbank | ..-- | | | | --C-- | --G-- | --T-- | --AA-- | --T-- | --TT-- |
| Cw2 (1) | ..-- | | | | --C-- | --G-- | --T-- | --AA-- | --T-- | --TT-- |
| Cw3 (1) | ..-- | | | | --C-- | --GT-- | --T-- | --AA-- | --T-- | --TT-- |
| Cw4 (1) | ..-- | | | | --C-- | --G-- | --T-- | --AA-- | --T-- | --TT-- |
| Cw5 (1) | ..-- | | | | --C-- | --G-- | --T-- | --AA-- | --T-- | --TT-- |
| Cw6 (2) | ..-- | | | | --C-- | --G-- | --T-- | --AAA-- | --T-- | --TT-- |
| Cw7 (2) | ..-- | | | | --C-- | --G-- | --T-- | --AAA-- | --T-- | --TT-- |
| Cw8 (1) | ..-- | | | | --C-- | | --C-- | --AA-- | --T-- | --TT-- |
| Cw12 (1) | ..-- | | | | --C-- | --G-- | --T-- | --AAA-- | --T-- | --TT-- |
| Cw14 (1) | ..-- | | | | --C-- | --G-- | --T-- | --AA-- | --T-- | --TT-- |
| Cw16 (1) | ..-- | | | | --C-- | --G-- | --T-- | --AA-- | --T-- | --TT-- |
| Cw17 (1) | ..-- | | | | --C-- | --TG-- | --C-- | --AA-- | --T-- | --TT-- |
| E Genbank | ..--T | --GT-- | --GA-- | --A-- | --CC-- | --CA-GA-- | --T-T-- | --A-- | --C-- | --TT-- |
| F (1) | | | --TT-- | | --C-- | | --T-- | | --T-- | ... |
| G (1) | --C-- | | | | | | --C-- | | --C-- | --T-C |
| H (1) | | --C-G-- | | | | | | | | --T-- |
| J.consen. Genbank | | | | --C-- | | --C...-- | --C..-- | --A-- | --C-- | --T-C |
| K.HLA70Genbank | | | | | --T-- | | | | | --T-- |
| L (1) | | | | --C-C-- | --G-- | --CC-T--C-- | --T-- | | --T-- | --T-- |

FIG. 5G (part 1)
Part IV of HLA Intron 3

```
                    363       369 372     378       384       390       396       402       408       414       420
                    --|---------|---|-----|---------|---------|---------|---------|---------|---------|---------|
A2 Genbank          TCTGAGTCCTTCAGCCTCCACTCAGGTCAGGACCAGAAGTCGCTGTT.CCCTCTT...CAGGGA
A2.msk vs.
       genbank
A2msk=cons          TCTGAGTCCTTCAGCCTCCACTCAGGTCAGGACCAGAAGTCGCTGTT.CCCTCTT...CAGGGA
A1    (1)           ------------TC-----------------------------------------TC-------------
A3    (1)           -------------C------------------------------------------TC-------------
A11   (1)           ------------TC-----------------------------------------TC-------------
A24   (2)           -------------C--------------------------------------------C-------------
A25   (1)           -------------C-----------------------------------------TC-------------
A26   (1)           ------------TC-----------------------------------------TC-------------
A66   (1)           -------------C-------------------------------------------------------
A28   (1)           -------------C-------------------------------------------------------
A29   (1)           -------------C-------------------------------------------------------
A30   (1)           -------------C-------------------------------------------------------
A31   (2)           -------------C-------------------------------------------------------
A32   (1)           -------------C-------------------------------------------------------
A33   (2)           -------------C-----------------------------------------TC-------------
B7    (2)           ------AC-TTA----------------A-----G--------C-----------CGC-------A----
B8    (1)           ------AC-TTA----------------A-----G--------C-----------CGC-------A----
B13   (1)           ------AC-TTA----------------A-----G--------C-----------CGC-------A----
B64   (1)           ------AC-TTA----------------A-----G--------T-----------CGC-------A----
B15(62)(1)          ------AC-TTA----------------A-----G--------C-----------CGC-------A----
B18   (1)           ------AC-TTA----------------A-----G--------T-----------CGC-------A----
B27 Genbank         ------AC-TTA----------------A-----G--------C-----------CGC-------A----
B35   (1)           ------AC-TTA----------------A-----G--------C-----------CGC-------A----
B37   (1)           ------AC-TTA----------------A-----G--------T-----------CGC-------A----
B38   (1)           ------AC-TTA----------------A-----G--------C-----------CGC-------A----
B42   (1)           ------AC-TTA----------------A-----G--------C-----------CGC-------A----
B44   (1)           ------AC-TTA--------------A-G-----G--------C-----------CGC-------A----
B45   (1)           ------AC-TTA----------------A-----G--------C-----------CGC-------A----
B46   (2)           ------AC-TTA----------------A-----G--------C-----------CGC-------A----
B50   (1)           ------AC-TTA----------------A-----G--------C-----------CGC-------A----
B51   (1)           ------AC-TTA----------------A-----G--------C-----------CGC-------A----
B52   (1)           ------AC-TTA----------------A-----G--------C-----------CGC-------A----
B54   (1)           ------AC-TTA----------------A-----G--------C-----------CGC-------A----
B57   (1)           ------AC-TTA----------------------G--------C-----------CGC-------A----
B58 Genbank         ------AC-TTA----------------A-----G--------C-----------CGC-------A----
```

FIG. 5G (part 2)
Part IV of HLA Intron 3

```
                        363       369 372      378       384       390       396       402       408       414       420
                        |---------|---|--|-----|---------|---------|---------|---------|---------|---------|---------|
A2 Genbank              TCTGAGTCCTTCAGCCTCCACTCAGGTCAGGACCAGAAGTCGCTGTT.CCCTCTT....CAGGGA
A2.msk vs.
        genbank         ...........................................................
A2msk=cons              TCTGAGTCCTTCAGCCTCCACTCAGGTCAGGACCAGAAGTCGCTGTT.CCCTCTT....CAGGGA
B60       (1)           -------------AC-TTA-------------A--------G------C--------CGC---A--
B61       (1)           -------------AC-TTA-------------A--------G------C--------CGC---A--
B65       (1)           -------------AC-TTA-------------A--------G------T--------CGC---A--

Cw1       (1)           --------------G-----------------------------------------------A--
Cw2       (1)           --------------G-----------------------------------------------A--
Cw2 Genbank             --------------G-----------------------------------------------A--
Cw3       (1)           --------------G-----------------------------------TC-C--------A--
Cw4       (1)           --------------G-----------------------------------TC-C--------A--
Cw5       (1)           --------------G-----------------------------------TC-C--------A--
Cw6       (2)           --------G-----------------------------------------TC-C--------A--
Cw7       (2)           --------------G-----------------------------------TC-C--------A--
Cw8       (1)           --------------G-----------------------------------TC-C--------A--
Cw12      (1)           --------------G-----------------------------------TC-C--------A--
Cw14      (1)           ----T---------G-----------------------------------TC-C--------A--
Cw16      (1)           --------------G-----------------------------------TC-C--------A--
Cw17      (1)           --------------G-----------------------------------TC-C--------A--

E Genbank               ---C----AC----A----------A---C-----------A--C--T..A-CT-CTACC-T--C
F         (1)           ....----C--GC-------T------------------------C--C--------G-----A--
G         (1)           --------C-TG-------------------A--------G-G--C-----CGC---A--
H         (1)           --------C-----------------------T-----------C-----C--C-A------GC--
J.consen.
        Genbank         --------C-TG----------A---------------------------C--C-A------A--
K.HLA70)                ------C---------G-----------------A---------A------C--------------
        Genbank
L         (1)           ----G-C-TG----------------------------------C------C--C-A------A--
```

FIG. 5G (part 3)
Part IV of HLA Intron 3

```
                         426       432       438       444       450       456       462       468
                         |----|----|----|----|----|----|----|----|----|----|----|----|----|----|
A2 Genbank           ....CTAGAA.TTTCCACGGAATAGGAGATTATCCCAGGTGCCTGTGTCCAGGCT
A2.msk vs.               ....................T.................................
 genbank
A2.msk=cons          ....CTAGAATTTCCACGGAATAGGAGATTATCCCAGGTGCCTGTGTCCAGGCT
A1   (1)             .......A----------------------------------------------
A3   (1)             ......................................................
A11  (1)             -----A------------------------------------------------
A24  (2)             -----A------------------------------------------------
A25  (1)             -----A------------------------------------------------
A26  (1)             ......................................................
A28  (1)             ......................................................
A29  (1)             ......................................................
A30  (1)             -----A------------------------------------------------
A31  (2)             ......................................................
A32  (1)             ......................................................
A33  (2)             ......................................................

B7   (2)             ----C-------------------AT----------------------C-----
B8   (1)             ----C-------------------AT----------------------CA----
B13  (1)             ----C-------------------AT----------------------C-----
B64  (1)             ----C-------------------AT----------------------C-----
B15(62)(1)           ----C-------------------AT----------------------C-----
B18  (1)             ----C-------------------AT----------------------C-----
B27 Genbank          ----C-------------------AT----------------------C-----
B35  (1)             ----C-------------------AT----------------------C-----
B37  (1)             ----C-C-----------------AT----------------------C-----
B38  (1)             ----C-------------------AT----------------------C-----
B42  (1)             ----C-------------------AT----------------------C-----
B44  (1)             ----C-------------------AT----------------------CA----
B45  (1)             ----C-------------------AT----------------------C-----
B46  (2)             ----C-------------------AT----------------------C-----
B50  (1)             ----C-------------------AT----------------------C-----
B51  (1)             ----C-C-----------------AT----------------------C-----
B52  (1)             ----C-------------------AT----------------------C-----
B54  (1)             ----C-------------------AT----------------------C-----
B57  (1)             ----C-------------------AT----------------------C-----
B58 Genbank          ----C-------------------AT----------------------C-----
B60  (1)             ----C-------------------AT----------------------C-----
```

FIG. 5G (part 4)
Part IV of HLA Intron 3

```
                           426       432       438      444       450       456       462       468
                           |----|----|----|----|----|----|----|----|----|----|----|----|----|----|
A2 Genbank             ....CTAGAA.TTTCCACGGAATAGGAGATTATCCCAGGTGCCTGTGTCCAGGCT
A2.msk vs.             ....--------T-------------------------------------------
  genbank
A2.msk=cons            ....CTAGAAtTTTCCACGGAATAGGAGATTATCCCAGGTGCCTGTGTCCAGGCT B61    (1)             ....--C----AT-------------------------C-----------------
B65    (1)             ....--C----AT-------------------------C-----------------

Cw1    (1)             ....--C----AT-------------------------------------------
Cw2    (1)             ....--C----AT-------------------------------------------
Cw2 Genbank            ....--C----AT-------------------------------------------
Cw3    (1)             ....--C----AT-------------------------------------------
Cw4    (1)             ....--C----AT-------------------------------------------
Cw5    (1)             ....--C----AT-------------------------------------------
Cw6    (2)             ....--C----AT-------------------------------------------
Cw7    (2)             ....--C----AT-------------------------------------------
Cw8    (1)             ....--C----AT-------------------------------------------
Cw12   (1)             ....--C----AT-------------------------------------------
Cw14   (1)             ....--C----AT-------------------------------------------
Cw16   (1)             ....--C----AT-------------------------------------------
Cw17   (1)             ....--C----AA----------------------------C--------------

E Genbank              TAGCTCATCCCGATT------C-----A----A----GC------T--A-C--AA-
F     (1)              ....--------------C--C-----A-----------------T-----T---C
G     (1)              ....-----------------C-----A-----------------------C----
H     (1)              ....--------------.-----------------------C-------------
J.consen.              ....-----------------C-----------------------------A----
  Genbank
K.HLA70) Genbank       ....
L     (1)              ....--------------C--------A-----------------------A-T--
```

FIG. 5H (part 1)
Part V of HLA Intron 3

```
                  474         483 486       492         498         504         510         516         522         528     534
                  |---|---|---|---|-|-|---|---|---|---|---|---|---|---|---|---|---|---|---|---|---|---|---|---|---|---|---|---|---|---|
A2 Genbank        GGTGTCTGGGTTCTGTGCTCCCTTCCCATCCCAGTGTCCTGTCCATTC.TCAAGATAGCCACA
A2.msk vs.        |---|---|---|---|-|-|---|---|---|---|---|---|---|---|---|---|---|---|---|---|---|---|---|---|---|---|---|---|---|---|
   Genbank
A2.msk=cons.      GGTGTCTGGGTTCTGTGCTCCCTTCCCATCCCAGTGTCCTGTCCATTC.TCAAGATAGCCACA
A1      (1)       ------------------------T---------------G-----------------G----
A3      (1)       ------------------------T---------------G-----------------G-G--
A11     (1)       ------------------------T---------------G-----------------G----
A24     (2)       ------------------------T---------------G-----------------G----
A25     (1)       ------------------------T---------------G----------------------
A26     (1)       ---------------------------------------------------------------
A28     (1)       ---------------------------------------------------------------
A29     (1)       ---------------------------------------------------------------
A30     (1)       ------------------------T---------------G-----------------G----
A31     (2)       ---------------------------------------------------------------
A32     (1)       ---------------------------------------------------------------
A33     (2)       ---------------------------------------------------------------
B7      (2)       ..................................G............................
B8      (1)       ...............................................................
B13     (1)       ...............................................................
B64     (1)       ............T..................................................
B15(62) (1)       ...............................................................
B18     (1)       ...............................................................
B27  Genbank      ............................................C..................
B35     (1)       ..............................C...............................G-C-G-T-
B37     (1)       ..............................C...............................-G-C-G-T-
B38     (1)       ..............................C...............................G-C-G-T-
B42     (1)       ..............................C...............................G-C-G-T-
B44     (1)       ..............................C...............................G-C-G-T-
B45     (2)       ..............................C...............................G-C-G-T-
B46     (1)       ..............................CA..............................G-C-G-T-
B50     (1)       ..............................C...............................G-C-G-T-
B51     (1)       ..............................C...............................G-C-G-T-
B52     (1)       ..............................CA..............................G-C-G-T-
B54     (1)       ..............................C...............................GTC-G-T-
B57     (1)       ..............................C...............................G-C-G-T-
```

FIG. 5H (part 2)
Part V of HLA Intron 3

| | 474 | 480 | 486 | 492 | 498 | 504 | 510 | 516 | 522 | 528 | 534 |
|---|---|---|---|---|---|---|---|---|---|---|---|
| A2 Genbank | GGTGTCTGGGTTCTGTGCTCCCTTCCCCATCCCAGGTGTCCTGTCCATTC.TCAAGATAGCCACA |
| A2.msk vs. Genbank | |
| A2.msk=cons. | GGTGTCTGGGTTCTGTGCTCCCTTCCCCATCCCAGGTGTCCTGTCCATTC.TCAAGATAGCCACA |
| B58 Genbank | ------------------------------.CA------------------.------G-C-G-T--- |
| B60 (1) | ---------------------------------C----------------.------G-C-G-T--- |
| B61 (1) | ---------------------------------C----------------.------G-C-G-T--- |
| B65 (1) | ---------T-----------------------C----------------.------G-C-G-T--- |
| Cw1 (1) | --C------------------------------C----------------.------G----G-T--- |
| Cw2 (1) | --C------------------------------C----------------.------G------T--- |
| Cw2 Genbank | |
| Cw3 (1) | --C------------------------------C----------------.------G----A-T--- |
| Cw4 (1) | --C------------------------------C--------------G-.------G----G-T--- |
| Cw5 (1) | --C------------------------------C----------------.------G----G-T--- |
| Cw6 (2) | --C------------------------------C----------------.------G----G-T--- |
| Cw7 (2) | --C----------------------------CG-C----------------.------G----G-T--- |
| Cw8 (1) | --C------------------------------C----------------.------G----G-T--- |
| Cw12 (1) | --C------------------------------C----------------.------G----G-T--- |
| Cw14 (1) | --C------------------------------C----------------.------G----G-T--- |
| Cw16 (1) | --C------------------------------C----------------.------G----G-T--- |
| Cw17 (1) | --C------------------------------C----------------.------G----G-T--- |
| E Genbank | ----AA----T---C-----TTC---TAC-ATA-T.----C-T-C-.------G----G-T--- |
| F (1) | -------------------------------------C------A--TG--T----G-.-T-G----T-G--- |
| G (1) | -------------------------------------C------A------T-G-----.-T-G----G----- |
| H (1) | --T----------------------------------C----------CA--------.--A----G----T--- |
| J.consen. Genbank | |
| K.HLA70Genbank | -----------C---------------------C----------------.-------G-------G----- |
| L (1) | -------------------------------------------------.-------G----G-T--- |

FIG. 5H (part 3)
Part V of HLA Intron 3

```
                        540       546       552       558       564       570       576       582       588       594
                        |---------|---------|---------|---------|---------|---------|---------|---------|---------|----|
A2 Genbank          T..GTGTGCTGGAGGAGTGTCCCATGACACAGATCGAAAATGCCTGAATGATCTGACTCTTCCTGA..CAG
A2.msk vs.                                 t                  GC
  Genbank
A2.msk=cons.    (1) T..GTGTGCTGGAGGAGTGTCCCATGACACAGATgcAAAATGCCTGAATGATGATCTGACTCTTCCTGA..CAG
A1       (1)           -C-                                                          --T-       -C-T-
A3       (1)           -C-        -T-                                                           -C-T-
A11      (1)           -C-        -T-                                                -T-        -C-T-
A24      (2)           -CA-                                                          -TT-
A25      (1)           -C-        -T-                                                -TT-
A26      (1)                                                                         -T-
A66      (1)                                           -A-CC                         --T-        -T-
A28      (1)
A29      (1)
A30      (1)           -C-                                                           -TT-
A31      (2)                                      -T-       -C-                      -T-         -C-T-
A32      (1)
A33      (2)                                      -T-       -C-                      -T-
B7       (2)           -G-        -G-CCTA-G                 -A-       -GC            -TT-        -CAT-
B8       (1)           -G-        -G-CCTA-G       -G-       -G-       -GC            -TT-        -CAT-
B13      (1)           -G-        -G-CCTA-G                 -G-       -GC            -TT-        -CAT-
B64      (1)           -G-        -G-CCTA-G                 -G-       -GC            -TT-        -CAT-
B15(62)(1)             -G-        -G-CCTA-G                 -G-    -T -GC            -TT-        -CAT-
B18      (1)           -G-        -G-CCTA-G                 -G-       -GC            -TT-        -CAT-
B27 Genbank            -G-        -G-CCTA-G                 -G-       -GC            -TT-        -CAT-
B35      (1)           -G-        -G-CCTA-G       -G-       -G-       -GC            -TT-        -CAT-
B37      (1)           -G-        -G-CCTA-G                 -G-       -GC            -TT-        -CAT-
B38      (1)           -G-        -G-CCTA-G                 -G-       -GC            -TT-        -CAT-
B42      (1)           -G-        -G-CCTA-G                 -G-       -GC            -TT-        -CAT-
B44      (1)           -G-        -G-CCTA-G                 -G-       -GC            -TT-        -CAT-
B45      (2)           -G-        -G-CCTA-G                 -G-       -GC            -TT-        -CAT-
B46      (1)           -G-        -G-CCTA-G                 -G-    -T -GC            -TT-        -CAT-
B50      (1)           -G-        -G-CCTA-G                 -G-       -GC            -TT-        -CAT-
B51      (1)           -G-        -G-CCTA-G                 -G-       -GC            -TT-        -CAT-
B52      (1)           -G-        -G-CCTA-G              -C -G-       -GC            -TT-        -CAT-
B54      (1)           -G-        -G-CCTA-G                 -G-       -GC            -ATT-       -CAT-
B57      (1)           -G-        -G-CCTA-G                 -G-       -GC            -TT-        -CAT-
```

FIG. 5H (part 4)
Part V of HLA Intron 3

|  | 540 | 546 | 552 | 558 | 564 | 570 | 576 | 582 | 588 | 594 |
|---|---|---|---|---|---|---|---|---|---|---|
| A2 Genbank | T..GTGTGCTGCTGGAGGAGTGTCCCATGACAGATGCAAAATGCCTGAATGATCTGACTCTTCCTGA.CAG |
| A2.msk vs. Genbank | ..                     t              GC |
| A2.msk=cons. | T..GTGTGCTGCTGGAGGAGTGTCCCATGACAGATGcAAAATGCCTGAATGATCTGACTCTTCCTGA.CAG |
| B58 Genbank (1) | ..-G---G-CCTA-G------------G---------GC----------TT-----------CAT.--- |
| B60 (1)         | ..-G---G-CCTA-G------------A---------GC----------TT-----------CAT.--- |
| B61 (1)         | ..-G---G-CCTA-G------------A---------GC----------TT-----------CAT.--- |
| B65 (1)         | ..-G---G-CCTA-G------------G---------GC----------TT-----------CAT.--- |
| Cw1 (1)         | ..-G-C---TT-----------G-A-G---AA-----G--T--------TT-----------C-T.--- |
| Cw2 (1)         | ..-G-C---TT-----------G-A-G----A------G--T--------TT-----------C-T.--- |
| Cw2 Genbank     | ..-G-C---TT-----------G-A-G----A------G--T--------TT-----------C-TG.--- |
| Cw3 (1)         | ..-G-C---TT-----------G-A-G----A------G--T--------TT-----------C-T.--- |
| Cw4 (1)         | ..-G-C---TT-----------G-A-G----A------G--T--------TT-----------C-T.--- |
| Cw5 (1)         | ..-G-CA--TT-----------G-A-G----A------G--T--------TT-----------C-T.--- |
| Cw6 (2)         | ..-G-C---TT-----------G-A-G----A------G--T--------TT-----------C-T.--- |
| Cw7 (2)         | ..-G-C---CT-----------A-A-G----A------G--T--------TT-----------C-T.--- |
| Cw8 (1)         | ..-G-CA--TT-----------G-A-G----A------G--T--------TT-----------C-T.--- |
| Cw12 (1)        | ..-G-C---TT-----------G-A-G----A------G--T--------TT-----------C-T.--- |
| Cw14 (1)        | ..-G-C---TT-----------G-A-G----A------G--T--------TT-----------C-T.--- |
| Cw16 (1)        | ..GCC----TT-----------G-A-G----A------G--T--------TT-----------C-T.--- |
| Cw17 (1)        | ..-G-C---CT-----------G-A-G----A------G--T--------TT-----------C-T.--- |
| E Genbank (1)   | ..--G----CT-----------G------G-A----G---G---------TT-----------CCT.--- |
| F (1)           | ..--G----CT--G--T------G--------GGAG-G---G---------TT-----------...TT.--- |
| G (1)           | ..-CCAG--CT-----------G---------G----G---G--T------TT-----------.TT.--- |
| H (1)           | ..--C----------------------------------------------TT-----------C-C.--- |
| J.consen. Genbank | ..-G-C---CT--G--------G-GGA----------G-----------G-TT-----------TT.--- |
| K.HLA70Genbank  | ..--C----CT-----T-----------------------G---------TT-----------T.T-.--- |
| L (1)           | ..--A----CT-----T-----T-GGA----------G-----------G-TT-----------CCT.--- |

Fig. 6 (part 1)
HLA Class I Non Classicals DNA Sequence
Exon 2 (Part I)

|  | 3 | 6 | 9 | 12 | 15 | 18 | 21 | 24 | 27 | 30 | 33 | 36 | 39 | 42 | 45 | 48 | 51 | 54 | 57 | 60 | 63 | 66 | 69 | 72 | 75 | 78 | 81 | 84 | 87 | 90 |
|---|---|---|---|---|---|---|---|---|---|---|---|---|---|---|---|---|---|---|---|---|---|---|---|---|---|---|---|---|---|---|
| CONSENSUS | G.CTCCCACTCCATGAGGTATTTCTACACCTCCGTGTCCCGGCCCGGCCGCGGGGAGCCCCGCTTCATCGCAGTGGGCTACGTGGACGACA |
| E EX23H | -.--------------------T-----------C-------T--------------------------------T------T------- |
| E 1.1-2  | -.-g-----T-----T--A-----C----------T-------T--------------------------T-T-------T---------- |
| E 1.2-2  | -.-g-----------T--A-----C----------T-------T--------------------------T-T-------T---------- |
| E 1E1    | -.--------------T--A-----C----------T-------T--------------------------T-T-------T---------- |
| E EA     | -.--------------T--A-----C----------T-------T--------------------------T-T-------T---------- |
| F        | -.-------T-------------------AG---G-T-----G-------------------------A---CA---------------- |
| G S50740 | -.---------------------------AG-G-G-----------------------------------CA------AG---------- |
| G S69897 | -.---------------------------AG-G-G-----------------------------------CA------------------ |
| G TRP    | -.---------------------------AGTG-G-----------------------------------CA------------------ |
| G 1A     | -.---------------------------AG-G-G-----------------------------------CA------------------ |
| G 21A    | -.---------------------------AG-G-G-----------------------------------CA------------------ |
| G 22A    | -.---------------------------AG-G-G-----------------------------------CA------------------ |
| G 3A     | -.---------------------------AG-G-G-----------------------------------CA------------------ |
| H        | -.-----------------------------A--A-------------------------------T-C--C-------T---------- |
| Geva 5   | -.-----------------------------A--A-------------------------------T-C--C-------T---------- |

|  | 93 | 96 | 99 | 102 | 105 | 108 | 111 | 114 | 117 | 120 | 123 | 126 | 129 | 132 | 135 |
|---|---|---|---|---|---|---|---|---|---|---|---|---|---|---|---|
| CONSENSUS | CGCAGTTCGTGCGGTTCGACAGCGACGCCGCGAGTCCGAGGATGG |
| E EX23H | -C-------------C-----A---------------------- |
| E 1.1-2  | -C-------------C-----A---------------------- |
| E 1.2-2  | -C-------------C-----A---------------------- |
| E 1E1    | -C-------------C-----A---------------------- |
| E EA     | -C-------------C-----A---------------------- |
| F        | ----A---C---------------------------T------- |
| G S50740 | --------------------------------T-G----T---- |
| G S69897 | --------------------------------T-G----T---- |
| G TRP    | --------------------------------T-G----T---- |
| G 1A     | --------------------------------T-G----T---- |
| G 21A    | --------------------------------T-G----T---- |
| G 22A    | --------------------------------T-G----T---- |
| G 3A     | --------------------------------T-G----T---- |
| H        | ----------------------------------------C-A- |
| Geva 5   | ---------------------A-----------------AGA-- |

Fig. 6 (part 2)
HLA Class I Non Classicals DNA Sequence
Exon 2 (Part II)

```
            138      144      150      156      162      168      174      180      186      192      198      204
            |--------|--------|--------|--------|--------|--------|--------|--------|--------|--------|--------|
CONSENSUS   AGCCGCGGGCGCCGTGGATAGAGC.AGGAGGGCCGGAGTATTGGGACCGGGAGACACAGAACTTCAAGG
E EX23H     T---------------------------------T-A-----------------------------G--G-GC--G--
E 1.1-2     T---------------------G-----------T-A-----------------------------G--G-GC--G--
E 1.2-2     T---------------------G-----------T-A-----------------------------G--G-GC--G--
E 1E1       T---------------------G-----------T-A-----------------------------G--G-GC--G--
E EA        T---------------------G-----------T-A-----------------------------G--G-GC--G--
F           ---------A------------G--------A-----C-----------GT--ACC---GG-T--GC--
G S50740    ----------------------G-G-------A-----------------AGA-----G-----AC--
G S69897    ----------------------G-G-G-----------------------AGA-----G-----AC--
G TRP       ----------------------G-------------------A-------AGA-----G-----AC--
G 1A        ----------------------G-G-------------------------AGA-----G-----AC--
G 21A       ----------------------G-G-------------------------AGA-----G-----AC--
G 22A       ----------------------G-G-------------------------AGA-----G-----AC--
G 3A        ----------------------G-G-------------------------AGA-----G-----AC--
H           ----------------------G---------------G-A---------------A-C-------T--G--
Geva 5      ----------------------G-G-c-----------------------------------------
Ja          ---A------G-----------G-G-------------------------TAC-----T-GG-GC--
Jb          -A--------G-----------G-G-------------------------TAC-----T-TG-GC--
Jc          -A--------G-----------G-G-------------------------TAC-----T-GG-GC--
J (HLA-59)  ---A------G-G-------G-G-----------------------TAC-----T-GG-GC--
K (HLA-70)  -------CA-------------T-G-------A-----------------AGC---G---A-.--
L (HLA-92)  ------G---------------G-G--------T----------------A-------G-----GC--
HLA-H1      ----------------------G-------------------------------A-C-----T--G--
HLA-H2      ----------------------G-------------------------------A-C-----T--G--
HLA-H       ----------------------G-------------------------------A-C-----T--G--
HLA-H4      ----------------------G-------------------------------A-C-----T--G--
Alice 23    ----------------------T-------------------------------A-C-----T--G--
```

Fig. 6 (part 3)
HLA Class I Non Classicals DNA Sequence
Exon 2 (Part II)

```
              210       216       222       228       234       240       246       252       258       264       270
              ---|---------|---------|---------|---------|---------|---------|---------|---------|---------|---------|---
              CCCACACACAGACTGACC.GAGAGAACCTGCGGGAACCTGCGGGGCTACTACAACCAGAGCGAGGCCG
E EX23H       A-AC-G------T-TT-.------T--------------CG----------------T------------
E 1.1-2       A-AC-G------T-TT-.------T--------------CG----------------T------------
E 1.2-2       A-AC-G------T-TT-.------T--------------CG----------------T------------
E 1E1         A-AC-G------T-TT-.------T--------------CG----------------T------------
E EA          A-AC-G------T-TT-.------T--------------CG----------------T------------
F             ---A--G-----------.----T-GC--------GC-----T-C--CG--------------------T-
G S50740      ------G-----------.----A--AT-------A--C-----------------------------A
G S69897      ------G-----------.----A--AT-------A--C-----------------------------A
G TRP         ------G-----------.----A--AT-------A--C-----------------------------A
G 1A          ------G-----------.----A--AT-------A--C-----------------------------A
G 21A         ------G-----------.----A--AT-------A--C-----------------------------A
G 22A         ------G-----------.----A--AT-------A--C-----------------------------A
G 3A          ------G-----------.----A--AT-------A--C-----------------------------A
H             ------GG----------A-------------------T-GC--T-C----------------------G-
Geva 5        ------GG----------.----------------------C---T-C----------------------G-
Ja            ------GG----------.----------------------C---T-C----------------------G-
Jb            ------GG----------.----------------------C---T-C----------------------G-
Jc            ------GG----------.----------------------C---T-C----------------------G-
J (HLA-59)    ------GG----------.-------T--------------C---T-C----------------------G
K (HLA-70)    ------G-G---------Aa----T--------CC-TG-C-----C--------C---------------
L (HLA-92)    G-----G--G---T-T--.----T-----------------C---T-C------------T---------
HLA-H1        ------GG----------A-----------G----------T-GC--T-C--------------------G--
HLA-H2        ------AG----------A----------------------T-GC--T-C--------------------G--
HLA-H         ------GG----------A----------------------T-GC--T-C--------------------G--
HLA-H4        ------AG----------A----------------------T-GC--T-C--------------------G--
Alice 23      G----------------------------N------T-NNNNT-C--------------------------
```

Fig. 7 (part 1)
HLA Class I Non Classicals DNA Sequence

Exon 3 (Part I)

| | 273 | 279 | 285 | 291 | 297 | 303 | 309 | 315 | 321 | 327 | 333 | 339 | 345 | 351 | 357 |
|---|---|---|---|---|---|---|---|---|---|---|---|---|---|---|---|
| CONSENSUS | GG | ..T.CTCACACCCTCCAGAGGATGTATGGCTGCGACGTGGGGCCGGACGGGCGCCTCCTCCGCGGGTATAACCAGTACGCCTACGACG |
| E EX23H | -- | ---- | --G-- | ----- | --C-- | ------ | --GC- | --C-- | ----- | ---T- | ----- | -G-A- | ---T- | ----- | ----- |
| F 1.1-2 | -- | ---- | --G-- | ----- | --C-- | ------ | --GC- | --C-- | ----- | ---T- | ----- | -G-A- | ---T- | ----- | ----- |
| 1.2-2 | -- | ---- | --G-- | ----- | --C-- | ------ | --GC- | --C-- | ----- | ---T- | ----- | -G-A- | ---T- | ----- | ----- |
| E 1E1 | -- | ---- | --G-- | ----- | --C-- | ------ | --GC- | --C--A | ----- | ---T- | ----- | -G-A- | ---T- | ----- | ----- |
| E EA | -- | ---- | --G-- | ----- | --C-- | ------ | --GC- | --C--A | ----- | ---T- | ----- | -G-A- | ---T- | ----- | ----- |
| F | -- | ---- | ----- | --G-A | --A-- | ------ | ---A- | --C-- | ----- | ----- | ----- | --C-- | ---C- | --G-- | ----- |
| G S50740 | -- | ---- | ----- | ---T- | -AT-- | ------ | ---C- | T-C-- | -A--- | ----- | ----- | -G-A- | ---T- | ----- | --T-- |
| G S69897 | -- | ---- | ----- | ---T- | -AT-- | ------ | ---C- | T-C-- | -A--- | ----- | ----- | -G-A- | ---T- | ----- | --T-- |
| G TRP | -T | ---- | ---T- | ---T- | -AT-- | ------ | ---C- | --T-- | -A--- | ----- | ----- | -G-A- | ---T- | ----- | --T-- |
| G 1A | -T | ---- | ----- | ---T- | -AT-- | ------ | ---C- | --T-- | -A--- | ----- | ----- | -G-A- | ---T- | ----- | --T-- |
| H | -- | -cgggccaggt | --A-G- | --GT- | ----- | ------ | ----- | ---C- | ----- | ---T- | ----- | -G-A- | --C-- | ----- | ---A |
| Ja | C- | ---- | ----- | --.A- | ---T- | ------ | ----- | ----- | ----- | ----- | ----- | -G-G- | ---T- | ----- | ----- |
| Jb | -- | ---- | --A-- | ---T- | ---T- | ------ | ----- | ----- | ----- | ---T- | ----- | -G-G- | ---T- | ----- | ----- |
| Jc | -- | ---- | --A-- | ---T- | ---T- | ------ | ----- | ----- | ----- | ---T- | ----- | -G-G- | ---T- | ----- | ----- |
| J (HLA-59) | -- | ---- | --.A- | ---T- | -TA-- | --TC-- | ----- | --T-- | -AC-- | ----- | ----- | -G-A- | ---T- | ----- | --T-- |
| K (HLA-70) | -- | ---- | ----- | --A-- | --A-C | ------ | ---C- | --.A- | ----- | ----- | --A-- | -G-A- | ---T- | --A-- | ----- |
| L (HLA-92) | -- | ---- | ----- | ----- | ----- | ------ | ----- | ----- | ----- | ----- | ----- | -G-A- | ---T- | ----- | --T-- |
| A-AR1 | -- | ---- | --A-G | -CGT- | ----- | ------ | ----- | --C-- | ----- | ---T- | ----- | -G-A- | ---C- | ----- | ---A |
| hLA-AR2 | -T | ---- | --A-G | --GT- | ----- | ------ | ----- | --C-- | ----- | ---T- | ----- | -G-A- | ---C- | ----- | ----- |
| HLA-AR3 | -T | ---- | --A-G | --GT- | ----- | ---T-- | ----- | --C-- | ----- | ---T- | ---T- | -G-A- | ---C- | ----- | ---A |
| HLA-AR4 | -T | ---- | --A-G | --GT- | ----- | ------ | ----- | --C-- | ----- | ---T- | ----- | -G-A- | ---C- | ----- | ----- |

Fig. 7 (part 2)
HLA Class I Non Classicals DNA Sequence
Exon 3 (Part I)

```
              363    369    375    381    387    393    399    408
              -|--|--|--|--|--|--|--|--|--|--|--|--|--|--|--|
CONSENSUS     GCAAGGATTACATCGCCCCTGAACGAGGACCTGCGCTCCTGGACCGGCGGCGG
E EX23H       -----------TC--A-----------T-------------------T-
E 1.1-2       -----------TC--A-----------T-------------------T-
E 1.2-2       -----------TC--A-----------T-------------------T-
E 1E1         -----------TC--A-----------T-------------------T-
E EA          -----------TC--A-----T-------------------------T-
F             ---------------T----------------------------------
G S50740      ---------C------------------------------A---------
G S69897      ---------C------------------------------A---------
G TRP         ---------C------------------------------A---------
G 1A          ---------C------------------------------A---------
H             ----------------T---------------------------------
Ja            -------------------------A---G----C---------C-----
Jb            -------------------------A--------C---------C-----
Jc            ----------------------------------C---------C-----
J (HLA-59)    -------------------------A-------------A----C-----
K (HLA-70)    -----------------T----T---------------------------
L (HLA-92)    -----------------T--------------------------------
HLA-AR1       -----------------T--------------------------C----A
HLA-AR2       -----------------T--------------------------------
HLA-AR3       -----------------T--------------------------------
HLA-AR4       -----------------T--------------------------------
```

Fig. 7 (part 3)
HLA Class I Non Classicals DNA Sequence

Exon 3 (Part II)

| | 411 | 417 | 423 | 429 | 435 | 441 | 447 | 453 | 459 | 465 | 471 | 477 |
|---|---|---|---|---|---|---|---|---|---|---|---|---|
| CONSENSUS | ACACGGCGGCT | CAGATCACC | AGCCGCAAG | TGGGAGGCG | GCCCGTGTG | GCGGAGCAG | CTGAGAGCCTACC |
| E EX23H | --- | --- | --- | T--G-- | --AA | ---CAA-T-AT | --TTC-A | --- | --- | C-A | --- | --- |
| E 1.1-2 | --- | --- | --- | T--G-- | --AA | ---CAA-T-AT | ---TC-A | --- | --- | C-A | --- | --- |
| E 1.2-2 | --- | --- | --- | T--G-- | --AA | ---CAA-T-AT | ---TC-A | --- | --- | C-A-G | --- | --- |
| E 1E1 | --- | --- | --- | T--G-- | --AA | ---CAA-T-AT | ---TC-A | --- | --- | C-A | --- | --- |
| E EA | --- | --- | --- | T--G-- | --AA | ---CAA-T-AT | ---TC-A | --- | --- | C-A | --- | --- |
| F | --- | C-T | --- | --- | TTC-AT | --- | -A-AGGAATAT | -A | --G | T-C-GA | --- | --- |
| G S50740 | --- | T--- | --- | T--A | --- | -T--- | --AA | --- | -T--- | -A-AAG | --- | --- |
| G S69897 | --- | T--- | --- | T--A | --- | -T--- | --AA | --- | -T--- | -A-AAG | --- | --- |
| G TRP | --- | T--- | --- | T--A | --- | -T--- | --AA | --- | -T--- | -A-AAG | --- | --- |
| G 1A | --- | T--- | --- | T--A | --- | -T--- | --AA | --- | -T--- | -A-AAG | --- | --- |
| H | --- | T--A | --- | --- | --- | --- | --- | -CA | --- | --- | --- | --- |
| Ja | --- | T--C | -T--- | --- | --- | -AT | --AA | --- | -T--- | -AAG | --- | --- |
| Jb | --- | T--C | -T--- | --- | --- | -AT | --AA | --- | -T--- | -AAG | --- | --- |
| Jc | --- | T--C | -T--- | --- | --- | -AT | --AA | --- | -T--- | -AAG | --- | --- |
| J (HLA-59) | --- | T--C | --- | --A--- | --- | -AT | --AA | --- | -T--- | -AAG | --- | --- |
| K (HLA-70) | --- | T--- | --- | --- | --- | --- | -A-AAGAAT-T-A | --- | --- | -A-C-G | --- | --- |
| L (HLA-92) | --- | T--A | --- | T--- | -A--- | --- | -A--AAATACT-A | --- | --- | -G-C--G | --- | --- |
| HLA-AR1 | --- | T--A | --- | --A--- | --- | --- | --- | -CA | --- | --- | --- | --- |
| HLA-AR2 | --- | T--A | --- | --A--- | --- | --- | --- | -CG | --- | --G | --T | --- |
| HLA-AR3 | --- | T--A | --- | --A--- | --- | --- | --- | -CA | --- | --- | --- | --- |
| HLA-AR4 | --- | T--A | --- | --A--- | --- | --- | --- | -CG | --- | --G | --T | --- |

Fig. 7 (part 4)
HLA Class I Non Classicals DNA Sequence
Exon 3 (Part II)

```
              483      489      495      501      507      513      519      525      531      537      546
              |--|--|--|--|--|--|--|--|--|--|--|--|--|--|--|--|--|--|--|--|--|--|--|
CONSENSUS     TGGAGGGCACGTGCGTGGAGTGGCTCCGCAGATACCTGGAGAACGGGAAGGAGACGCTGCAGCGCGCGG
E EX23H       ----A-A----A--------------A--A----------G--------------------TT-A-CT-
E 1.1-2       ----A-A----A--------------A--A----------G--------------------TT-A-CT-
E 1.2-2       ----A-A----A--------------A--A----------G--------------------TT-A-CT-
E 1E1         ----A-A----A--------------A--A----------G--------------------TT-A-CT-
E EA          ----A-A----A--------------A--A----------G--------------------TT-A-CT-
F             --------GA---C-----T------------T-------T------T-------A------------A-
G S50740      ---------------------------A------------------T---------------------
G S69897      ---------------------------A------------------T---------------------
G TRP         ---------------------------A------------------T---------------------
G 1A          ---------------------------A----------------------------------------
H             --------GA--T--------------------C-----------------------------------
Ja            ----------C--A-------------------C-----------------------------------
Jb            ----------C--A-------------------C-----------------------------------
Jc            ----------C--A-------------------C-----------------------------------
J (HLA-59)    ----------C----------A-----------C----------------T----------T-A-----
K (HLA-70)    -----------------------------------------------------------------A---
L (HLA-92)    ---.----A---A--------------.-----N-----T-----------------A-----------
HLA-AR1       -----------GA--T------------------------------------------------------
HLA-AR2       -----------GA--T------------------------------------------------------
HLA-AR3       -----------GA--T------------------------------------------------------
HLA-AR4       -----------GA--T------------------------------------------------------
```

FIG. 8 (Part 1)
B-LCL Panel

| Dot Number | Name | HLA-A | HLA-B | HLA-C | Dot Number | Name | HLA-A | HLA-B | HLA-C |
|---|---|---|---|---|---|---|---|---|---|
| 1 | SA | A24 | B7 | Cw07 | 54 | EX | A2 | B44 | Cw05 |
| 2 | MZO70782 | A24 | B14 | Cw02, Cw05 | 55 | _0301 | A3 | B14 | Cw08 |
| 3 | KAS116 | A24 | B51 | Cw12 | 56 | KOSE | A2 | B35 | Cw12 |
| 4 | JESTHOM | A2 | B27 | Cw01 | 57 | TEM | A26 | B38 | Cw12 |
| 5 | HOM2 | A3 | B27 | Cw01 | 58 | OMW | A2 | B45 | Cw16 |
| 6 | W_100BIS | A11 | B35 | Cw04 | 59 | SLE005 | A2 | B60 | Cw03 |
| 7 | DEM | A2 | B57 | Cw06 | 60 | CB6B | A1 | B62 | Cw03 |
| 8 | DO208915 | A25 | B18 | Cw12 | 61 | 31227ABO | A2 | B18 | Cw07 |
| 9 | KAS011 | A1 | B37 | Cw06 | 62 | WUV | A2 | B38 | Cw12 |
| 10 | AMA1 | A28 | B53 | Cw04 | 63 | WT47 | A32 | B44 | Cw05 |
| 11 | E4181324 | A1 | B52 | Cw12 | 64 | AMALA | A2 | B62 | Cw03 |
| 12 | WJR076 | A2 | B57 | Cw07 | 65 | HHKB | A3 | B7 | Cw07 |
| 13 | SCHU | A3 | B7 | Cw07 | 66 | TABO89 | A2 | B46 | Cw01 |
| 14 | MGAR | A26 | B8 | Cw07 | 67 | BTB | A2 | B27 | Cw01 |
| 15 | WT24 | A2 | B27 | Cw02 | 68 | BM9 | A2 | B35 | Cw04 |
| 16 | RML | A2 | B51 | Cw15 | 69 | MADURA | A2 | B60 | Cw03 |
| 17 | WTB | A3 | B7 | Cw07 | 70 | LUY | A2 | B51 | Cw14, Cw00 |
| 18 | LOO81705 | A3,A24 | B18 | Cw05 | 71 | OLGA | A31 | B62 | Cw01 |
| 19 | DUCAF | A30 | B18 | Cw05 | 72 | SPACH | A31 | B62 | Cw01 |
| 20 | QBL | A26 | B18 | Cw05 | 73 | KT12 | A24,A31 | B51,B35 | Cw04, Cw00 |
| 21 | RSH | A68,A30 | B42 | Cw17 | 74 | HID | A2 | B60,B61 | Cw03, Cw08 |
| 22 | COX | A1 | B8 | Cw07 | 75 | DKB | A24 | B60 | Cw03 |
| 23 | VAVY | A1 | B8 | Cw07 | 76 | T7526 | A2 | B46 | Cw01 |
| 24 | KT17 | A2,A11 | B35,B62 | Cw04, Cw03 | 77 | T7527 | A2 | B46 | Cw01 |
| 25 | DEU | A31 | B35 | Cw04 | 78 | _MGO75 | A3,A33 | B65 | Cw08 |
| 26 | YAR | A26 | B38 | Cw12 | 79 | LWAGS | A33 | B14 | Cw08 |
| 27 | PF97387 | A29 | B44 | Cw16 | 80 | EHM | A3 | B35 | Cw04 |
| 28 | PE117 | A24 | B60,B61 | Cw08 | 81 | EA | A3 | B7 | Cw07 |

FIG. 8 (Part 2)
B-LCL Panel

| Dot Number | Name | HLA-A | HLA-B | HLA-C | Dot Number | Name | HLA-A | HLA-B | HLA-C |
|---|---|---|---|---|---|---|---|---|---|
| 29 | WT51 | A23 | B65 | Cw08 | 82 | HO104 | A3 | B7 | Cw07 |
| 30 | JHAF | A31 | B51v | Cw15 | 83 | LD2B | A3 | B7 | Cw07 |
| 31 | BOLETH | A2 | B62 | Cw03 | 84 | CALOGERO | A2 | B61 | Cw02 |
| 32 | BSM | A2 | B62 | CW03 | 85 | EJ32B | A30 | B18 | Cw05 |
| 33 | BM14 | A3 | B7 | Cw07 | 86 | LO541265 | A1 | B8 | Cw07 |
| 34 | SAVC | A3 | B7 | Cw07 | 87 | STEINLIN | A1 | B8 | Cw07 |
| 35 | JBUSH | A2 | B38 | Cw12 | 88 | PFO4015 | A1 | B8 | Cw07 |
| 36 | SPOO10 | A2 | B44 | Cw05 | 89 | BOB | A24 | B51 | Cw15 |
| 37 | SWE1G007 | A29 | B61 | Cw02 | 90 | AWELLS | A2 | B44 | Cw05 |
| 38 | BM16 | A2 | B18 | Cw07 | 91 | MLF | A2 | B62 | Cw03 |
| 39 | JVM | A2 | B18 | Cw05 | 92 | BM92 | A25 | B51 | Cw01 |
| 40 | BM15 | A1 | B35 | Cw04 | 93 | BER | A2 | B13 | Cw06 |
| 41 | JO528239 | A1 | B35 | Cw04 | 94 | CF996 | A2,A3 | B14 | Cw08 |
| 42 | TISI | A24 | B35 | Cw05 | 95 | WIN | A1 | B57 | Cw06 |
| 43 | BM21 | A1 | B41 | CW17 | 96 | LBF | A30 | B13 | Cw06 |
| 44 | BRIP | A24 | B51,B15 | Cw00 | 97 | EMJ | A2,A3 | B60 | Cw03 |
| 45 | TUBO | A2,A3 | B51 | Cw07, Cw15 | 98 | MT14B | A31 | B60 | Cw03 |
| 46 | BH | A2 | B13 | Cw06 | 99 | LZL | A2 | B62 | Cw03 |
| 47 | PLH | A3 | B47 | Cw06 | 100 | OLL | A31 | B62 | Cw01 |
| 48 | LBUF | A30 | B13 | Cw06 | 101 | SPL | A31 | B62 | Cw01 |
| 49 | IBW9 | A33 | B65 | Cw08 | 102 | ARBO | A3 | B57 | Cw06 |
| 50 | MOU | A29 | B44 | Cw16 | 103 | KT14 | A24,A26 | B51,B61 | Cw08, Cw14 |
| 51 | PITOUT | A29 | B44 | Cw16 | 105 | FPAF | A1 | B35 | Cw04, Cw00 |
| 52 | DBB | A2 | B57 | Cw06 | 106 | MANIKA | A3 | B50 | Cw06 |
| 53 | HOR | A2 | B44 | Cw14 | 107 | LKT3 | A24 | B54 | Cw01 |

METHODS AND REAGENTS FOR TYPING HLA CLASS I GENES

SPECIFICATION

This application relates to methods and reagents for typing HLA alleles of Class I genes.

The HLA Class I genes are a component of the human major histocompatibility complex (MHC). The Class I genes consist of the three classical genes encoding the major transplantation antigens HLA-A, HLA-B and HLA-C and seven non-classical class I genes, HLA-E, HLA-F, HLA-G, HLA-H, HLA-J, HLA-K and HLA-L.

The classical HLA Class I genes encode polymorphic cell surface proteins expressed on most nucleated cells. The natural function of these proteins is to bind and present diverse sets of peptide fragments from intracellularly processed antigens to the T cell antigen receptors (TCRs). Thus, the peptide-binding capability of the MHC molecule facilitates immune recognition of intracellular pathogens and altered self proteins. Therefore, by increasing the peptide repertoire for TCRs, the polymorphism of MHC molecules plays a critical role in the immune response potential of a host. On the other hand, MHC polymorphism exerts an immunological burden on the host transplanted with allogeneic tissues. As a result, mismatches in HLA class I molecules are one of the main causes of allograft rejection and graft versus host disease, and the level of HLA matching between tissue donor and recipient is a major factor in the success of allogeneic tissue and marrow transplants. It is therefore a matter of considerable medical significance to be able to determine the "type" of the HLA Class I genes of candidate organ donors and recipients.

HLA class I histocompatibility antigens for patient-donor matching are conventionally determined by serological typing. Biochemical and molecular techniques have revealed that HLA class I polymorphism is far greater than previously recognized by conventional methods. To date, over 59 HLA-A, 127 HLA-B, and 36 HLA-C different allelic sequences have been identified. Bodmer et al., "Nomenclature for factors of the HLA system," *Tissue Antigens* 46: 1–18 (1995). This high level of allelic diversity complicates the typing of the HLA class I genes.

Another complicating factor is the large number of homologous genes and alleles. Each of the HLA Class I genes is composed of eight exons and seven introns as shown in FIG. 1, and the sequences of these exons and introns are highly conserved across the HLA Class I genes. Allelic variations mostly occur in exons 2 and 3 which are flanked by noncoding introns 1, 2, and 3. These two exons encode the functional domains of the molecules.

Taken together, these two complications make HLA Class I typing at the nucleic acid level a formidable task. Allelic diversity within any one gene means that a great many probes need to be developed if hybridization-based tests are used in the typing. Further, the general applicability of DNA typing methods to HLA Class I genes depends on the design of primers which provide effective locus-specific amplification of exons 2 and/or 3 of one HLA Class I gene.

One method for performing HLA Class-I typing is disclosed in U.S. Pat. No. 5,424,184 which is incorporated herein by reference. This patent utilizes primers which are located within exons 2 and 3 of the HLA Class-I genes to achieve what is described as group-specific amplification of a portion of the HLA-A, HLA-B and HLA-C genes. This approach is not ideal, however, since the primers hybridize with portions of the coding strand, and thus may mask significant allelic variations. In addition, this method requires a grouping of alleles by means of another method in order to select group-specific primers for amplification.

In assessing the known exon 2 and 3 sequences found in the HLA class I sequence database (Arnett & Parham, *Tissue Antigens* 46: 217–257 (1995)), there is only one possible HLA-A locus-specific primer site located in exon 2. (Oh et al., *Tissue Antigens* 41: 135–142 (1993)) Using a primer for this site, HLA-A locus-specific amplification produced a PCR product of 671bp, containing a portion of exon 2, intron 2, and exon 3. This amplified DNA fragment does not contain the first variable region of HLA-A the molecule. In addition, the primers are not entirely specific and lead to amplification of some HLA-H alleles. Thus, locus-specific amplification using this primer does not provide a highly effective method for typing HLA-A genes.

Similar evaluations of the known exon sequences (Arnett and Parham, supra) showed that there are no suitable primer sites for the HLA-B genes. For HLA-C alleles, two separate sets of primers are needed to amplify both exon 2 and 3. (Levine and Yang, *Tissue Antigens* 44: 174–183 (1994). Universal primers designed for exons 2 and 3 also amplified the non-classical genes. Exon 4 contains locus-specific sequences but it is separated by ≈590bp from exon 3, making exon 4 an impractical PCR primer site.

Thus, there remains a real need for locus-specific primers for the HLA class I genes to provide amplified materials for use in class I typing by PCR-DNA methods (e.g. Sequencing-, SSO-, and SSP-based). It is an object of the present invention to provide methods and reagents effective to provide locus-specific amplification of the HLA Class I genes.

It is a further object of the present invention to provide locus-specific primers amplification primers which hybridize with the introns flanking exons 2 and 3 of the major transplantation antigens.

It is still a further object of the present invention to use these primers to achieve locus-specific amplification which is an essential step in developing a DNA-based HLA class I typing methodology.

SUMMARY OF THE INVENTION

We have determined the sequences of introns 1, 2 and 3 from the majority of HLA-A, -B and -C allotypes and from alleles of HLA-E, -F, -G, -H, -J, -K, and -L. From these intron sequences, we have now developed primers located within introns 1 and 3 of the HLA-A, HLA-B and HLA-C genes. These primers are suitable for locus-specific amplification of the entirety of exons 2 and 3, i.e., the portion of these of genes most suitable for use in typing of HLA-A, HLA-B and HLA-C. These primers are also suitable for use as sequencing primers to determine the HLA alleles in sequence-based HLA typing. Thus, in accordance with the invention, there is provided a method for testing a sample to determine the HLA-A, -B or -C type of the sample comprising the steps of (a) treating the tissue sample to obtain nucleic acid polymers suitable for amplification;

(b) combining the nucleic acid polymers with a first primer which is complementary to a portion of intron 1 of the HLA gene, and a second primer which is complementary to a portion of intron 3 of the HLA gene under conditions suitable for amplification to obtain an amplified product; and (c) evaluating the amplified product to determine the allelic type of the HLA-A, HLA-B or HLA-C genes.

This evaluation step can make use of any of the known methods for nucleic acid-based typing of HLA genes, including direct sequencing, sequence-specific oligotyping (SSO) or sequence-specific primer amplification (SSP) of the amplified products. Preferably, at least one of the amplification primers has a sequence which provides locus-specific amplification.

In addition, we have identified primers which provide locus-specific amplification for HLA-E, HLA-F, HLA-G. HLA-H, HLA-J, HLA-K and HLA-L. Thus, there is also provided a method for testing a tissue sample to determine the HLA-E, HLA-F, HLA-G, HLA-H, HLA-J, HLA-K and/or HLA-L type of the sample comprising the steps of (a) treating the tissue sample to obtain nucleic acid polymers suitable for amplification;

(b) combining the nucleic acid polymers with a first primer which is complementary to a portion of exon 2 of the human major histocompatibility complex, and a second primer which is complementary to a portion of exon 3 of the human major histocompatibility complex under conditions suitable for to obtain an amplified product; and (c) evaluating the amplified product to determine the allelic type of the HLA-E, HLA-F, HLA-G, HLA-H, HLA-J, HLA-K and HLA-L genes. This evaluation step can make use of sequence-specific oligotyping, PCR-SSOP-based typing or can involve direct sequencing the amplified products.

BRIEF DESCRIPTION OF THE DRAWINGS

FIG. 2 shows a consensus sequence for intron 1 of the classical HLA Class I genes with suggested primer locations;

FIG. 3 shows a consensus sequence for intron 2 of the classical HLA Class I genes with suggested primer locations;

FIG. 4 shows a consensus sequence for intron 3 of the classical HLA Class I genes with suggested primer locations;

FIGS. 5A–5H shows individual aligned sequences determined for each intron;

FIG. 6 shows the sequences of exon 2 of the non-classical HLA Class I genes;

FIG. 7 shows the sequences of exon 3 of the non- classical HLA Class I genes; and FIG. 8 shows the name and allelic type of 107 cell lines tested using the amplification primers of the invention.

DETAILED DESCRIPTION OF THE INVENTION

Figure 1:
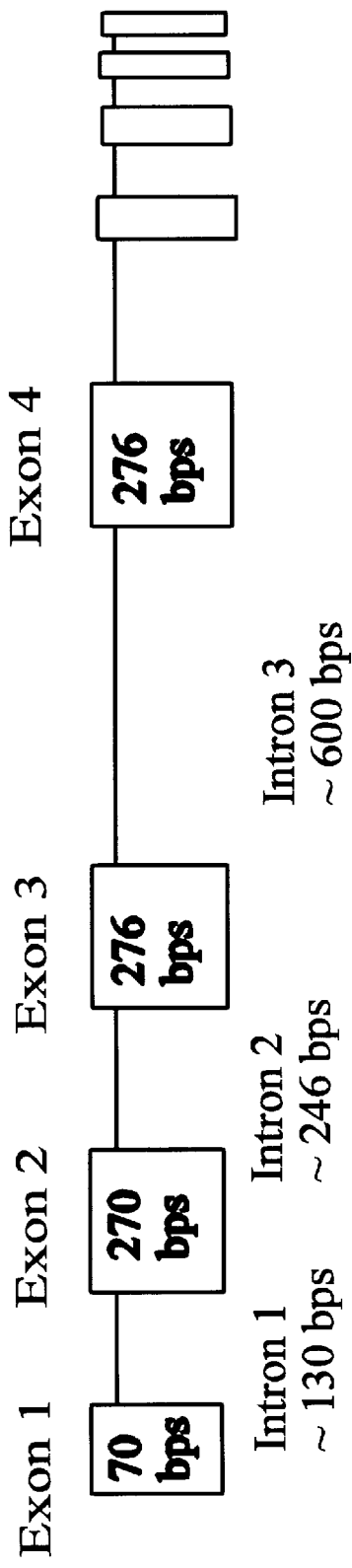
FIG. 1 shows the organization of the eight exons and seven introns of an HLA Class I gene.

The present invention relates to methods for typing tissue samples to determine the HLA Class I type of the sample. Thus, a first embodiment of the invention is a method for testing a tissue sample to determine the HLA-A, HLA-B or HLA-C type of the sample comprising the steps of (a) treating the tissue sample to obtain nucleic acid polymers suitable for amplification;

(b) combining the nucleic acid polymers with a first primer which hybridizes with a portion of intron 1 or intron 3 of the HLA-gene being tested, and a second primer which hybridizes with a different portion of the HLA-gene being tested under conditions suitable for nucleic acid amplification to obtain an amplified product; and (c) evaluating the amplified product to determine the allelic type of the HLA-A, HLA-B or HLA-C genes. Preferably, at least the first amplification primer is one which specifically hybridizes to only one type of HLA Class I gene, so that locus specific amplification is achieved.

Figure 5A:
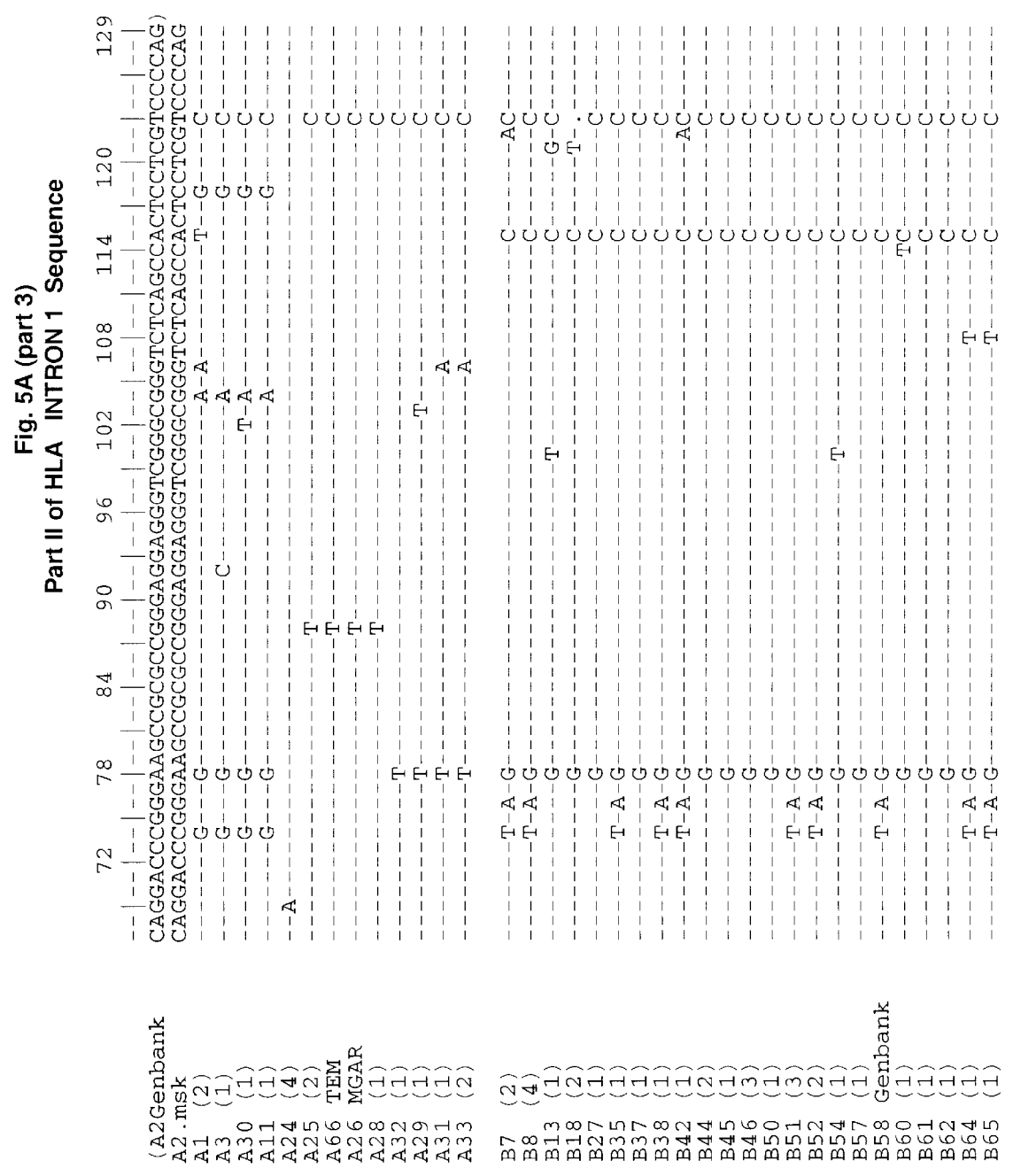
Figure 5B:
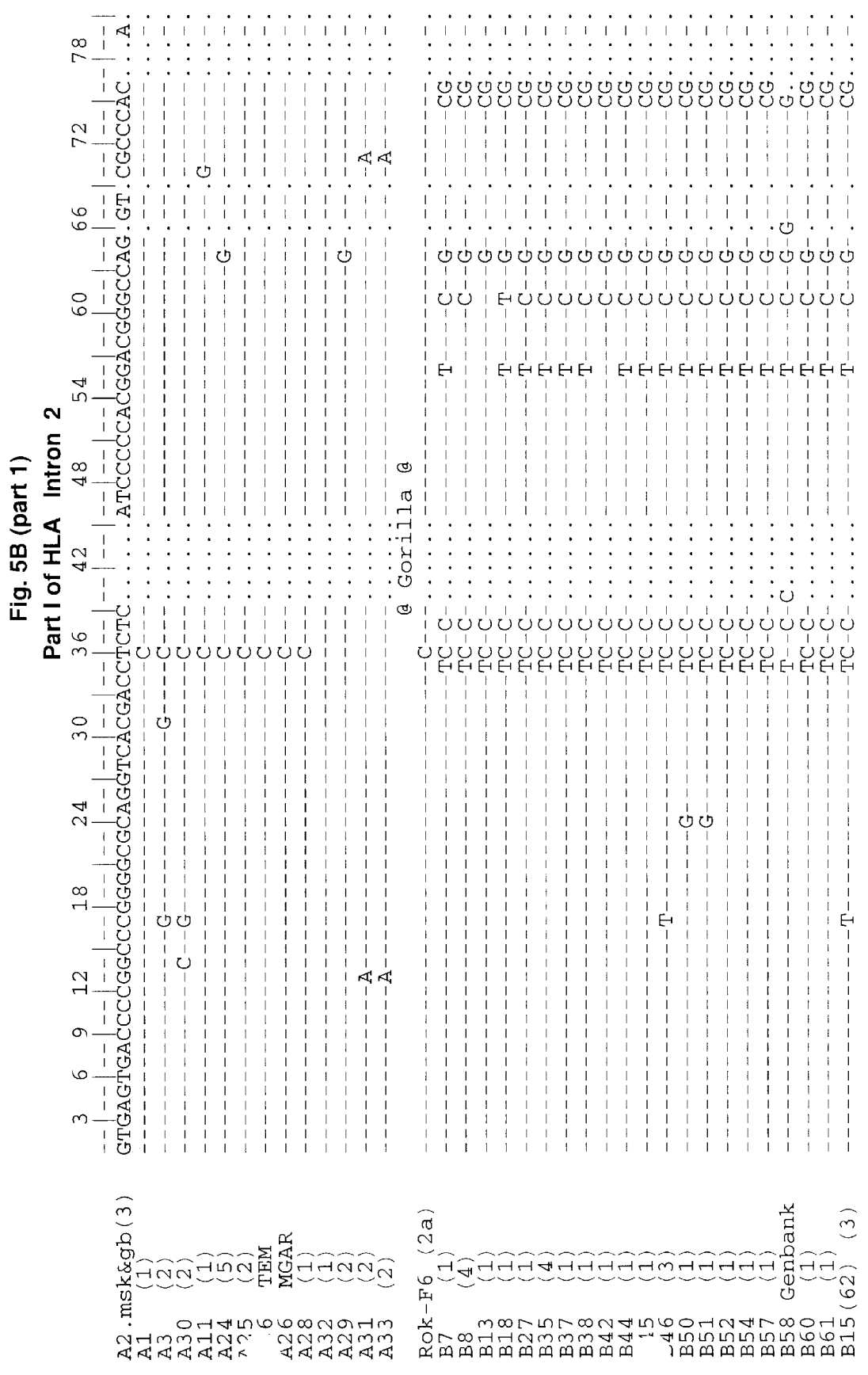
Figure 5B:
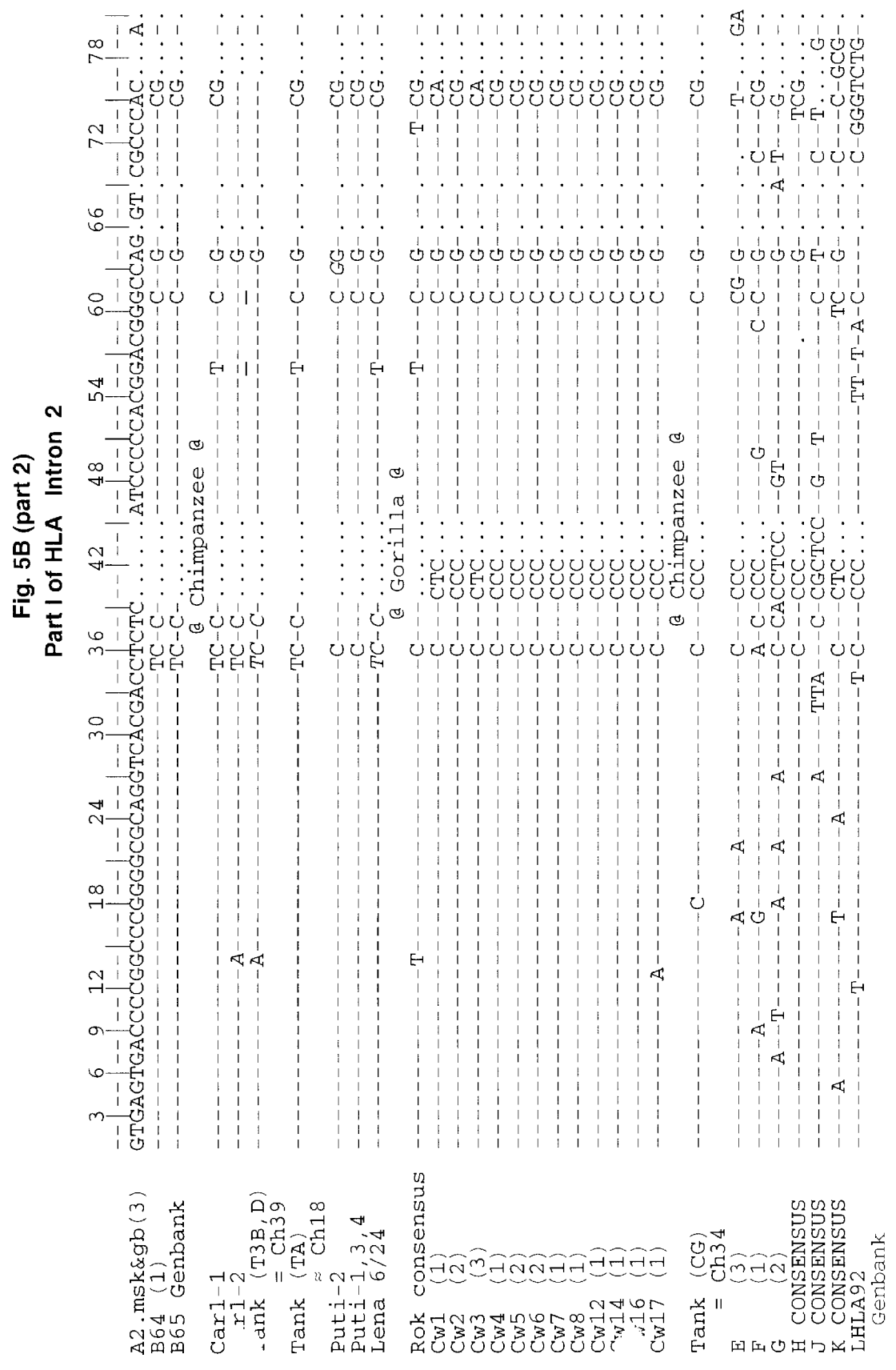
Figure 5B:
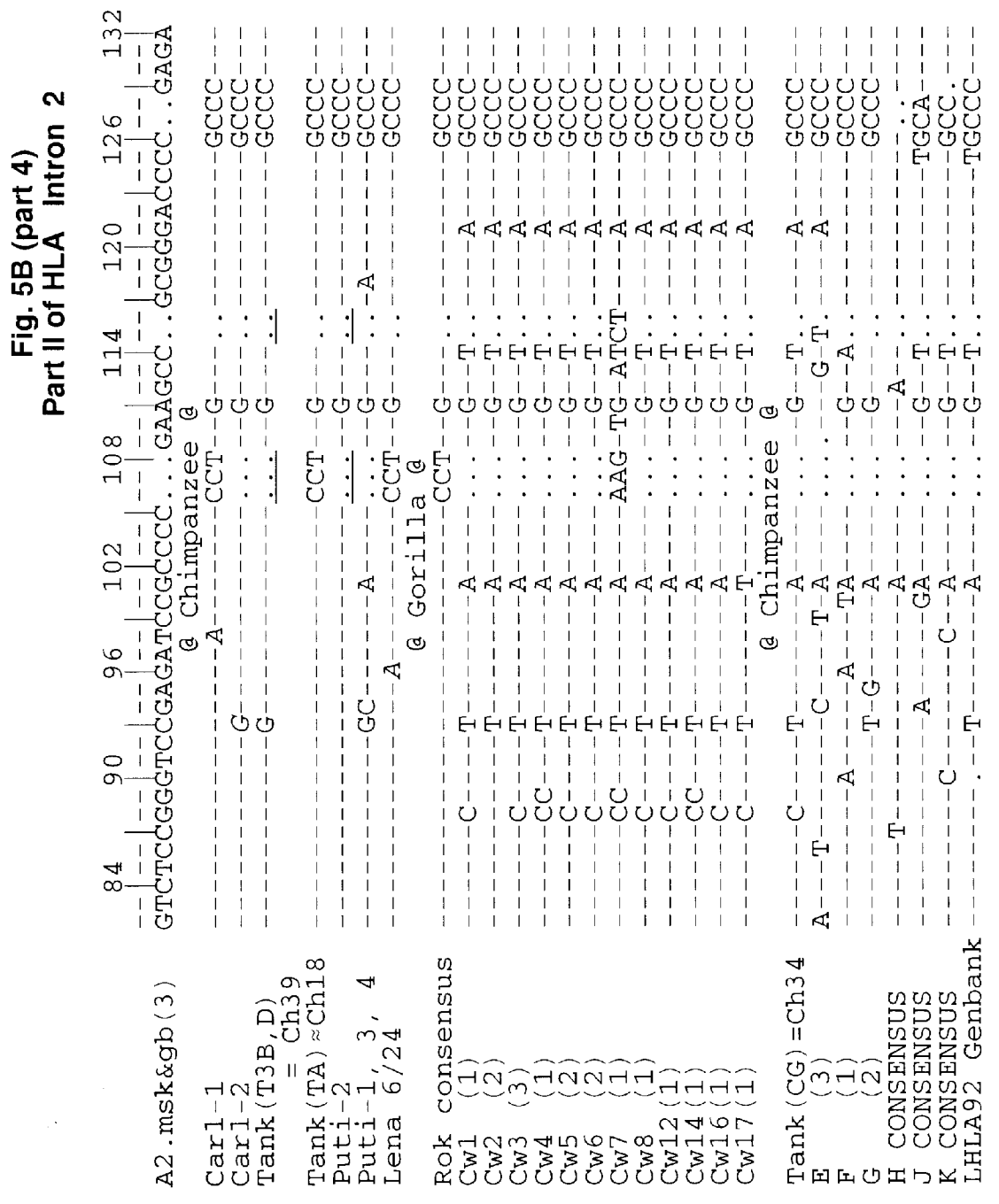
Figure 5C:
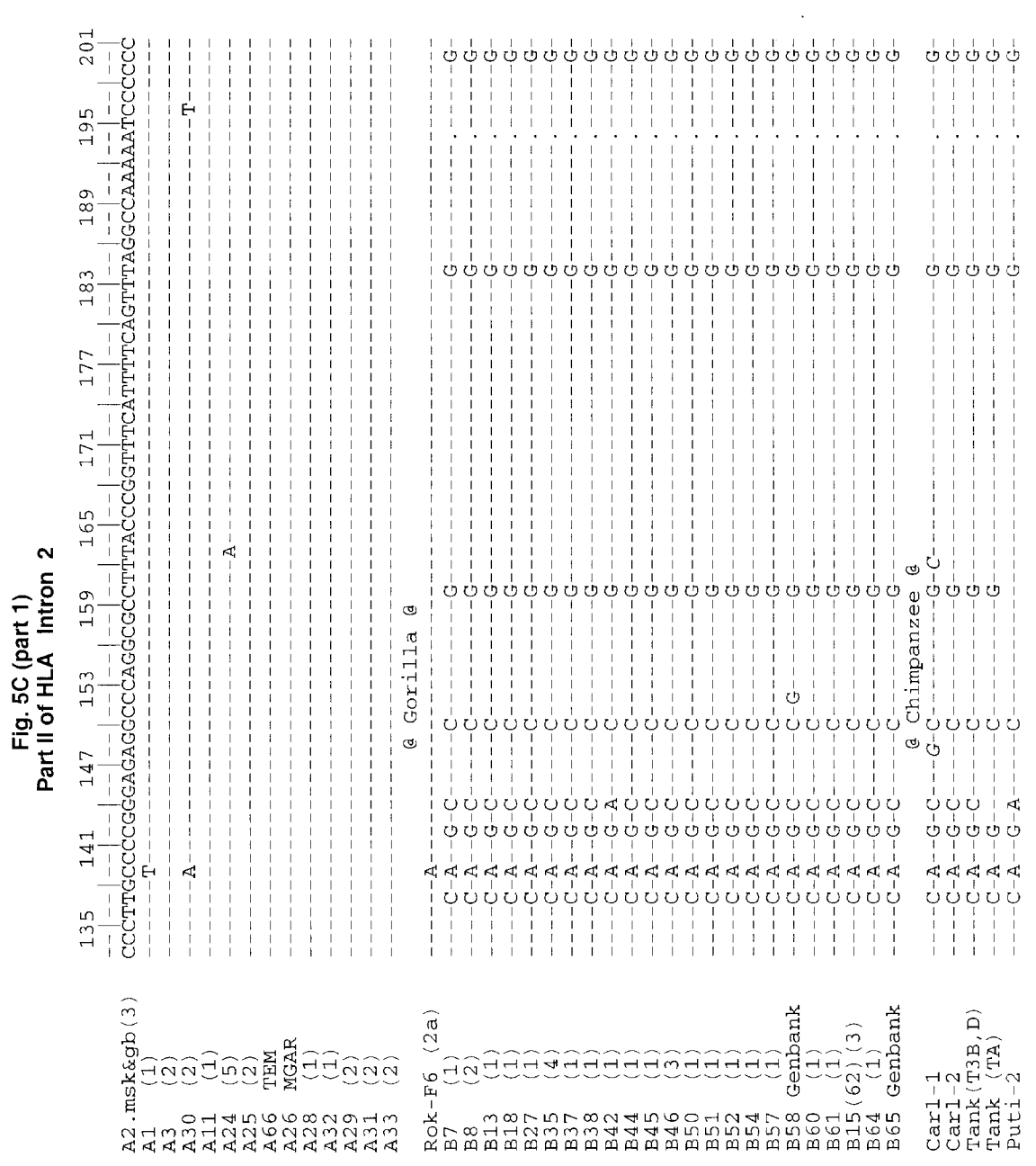
Figure 5D:
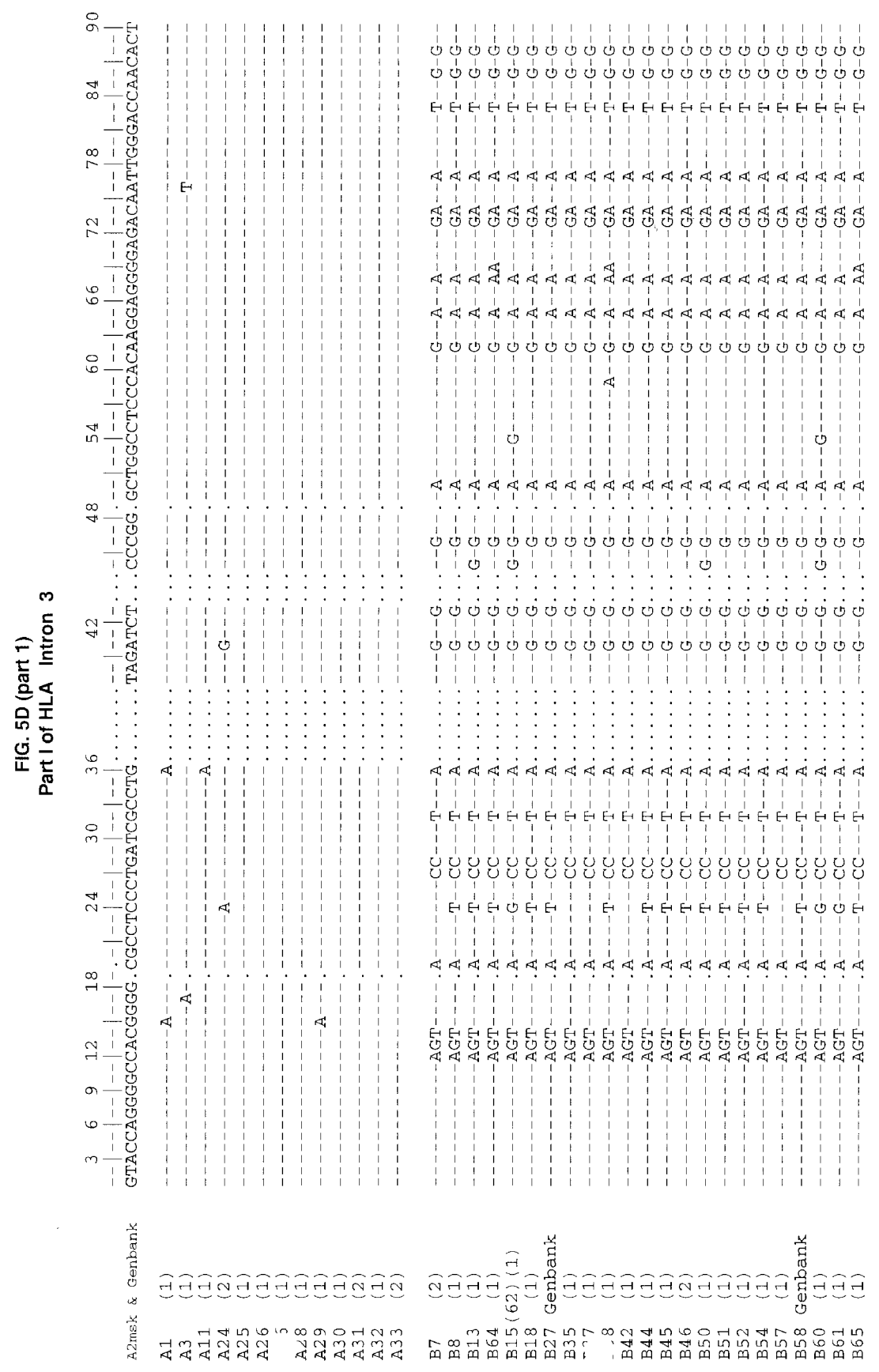
Figure 5D:
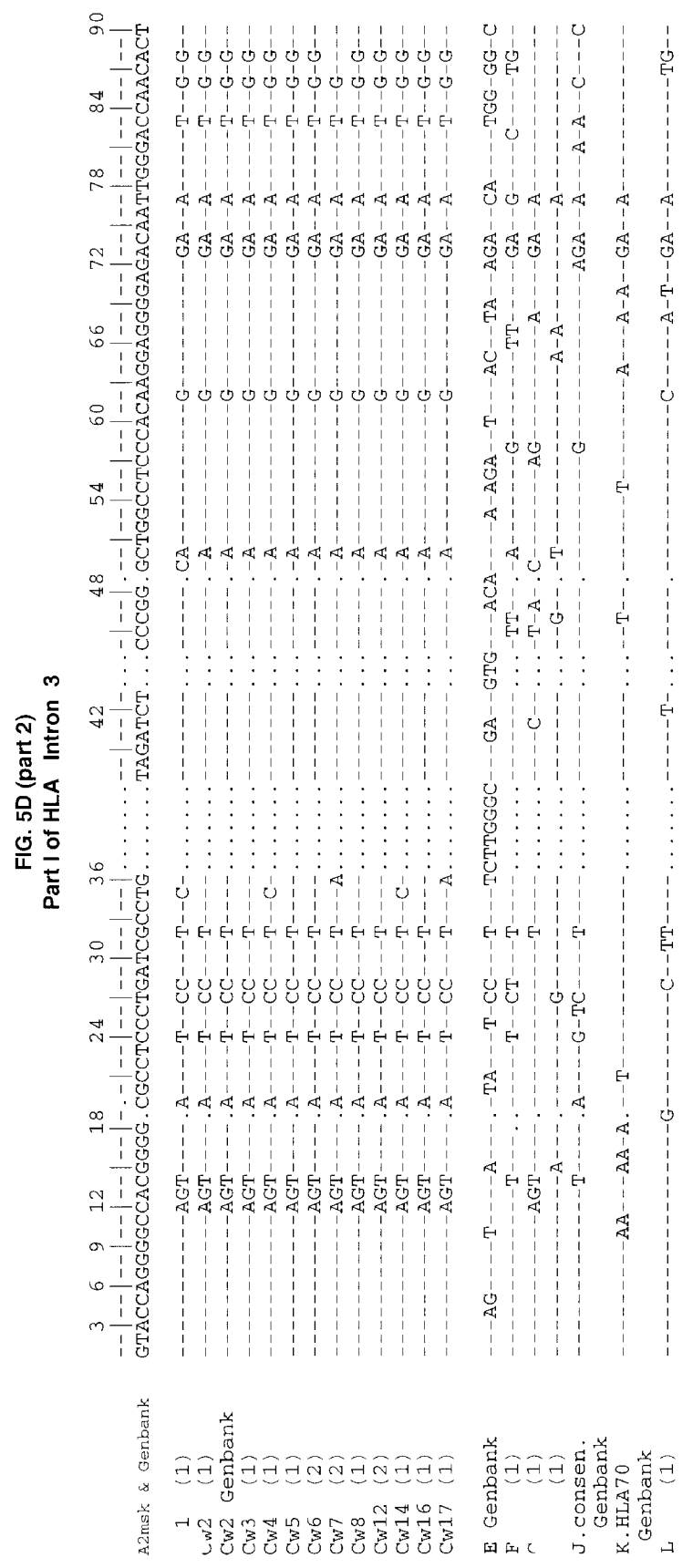
Figure 5E:
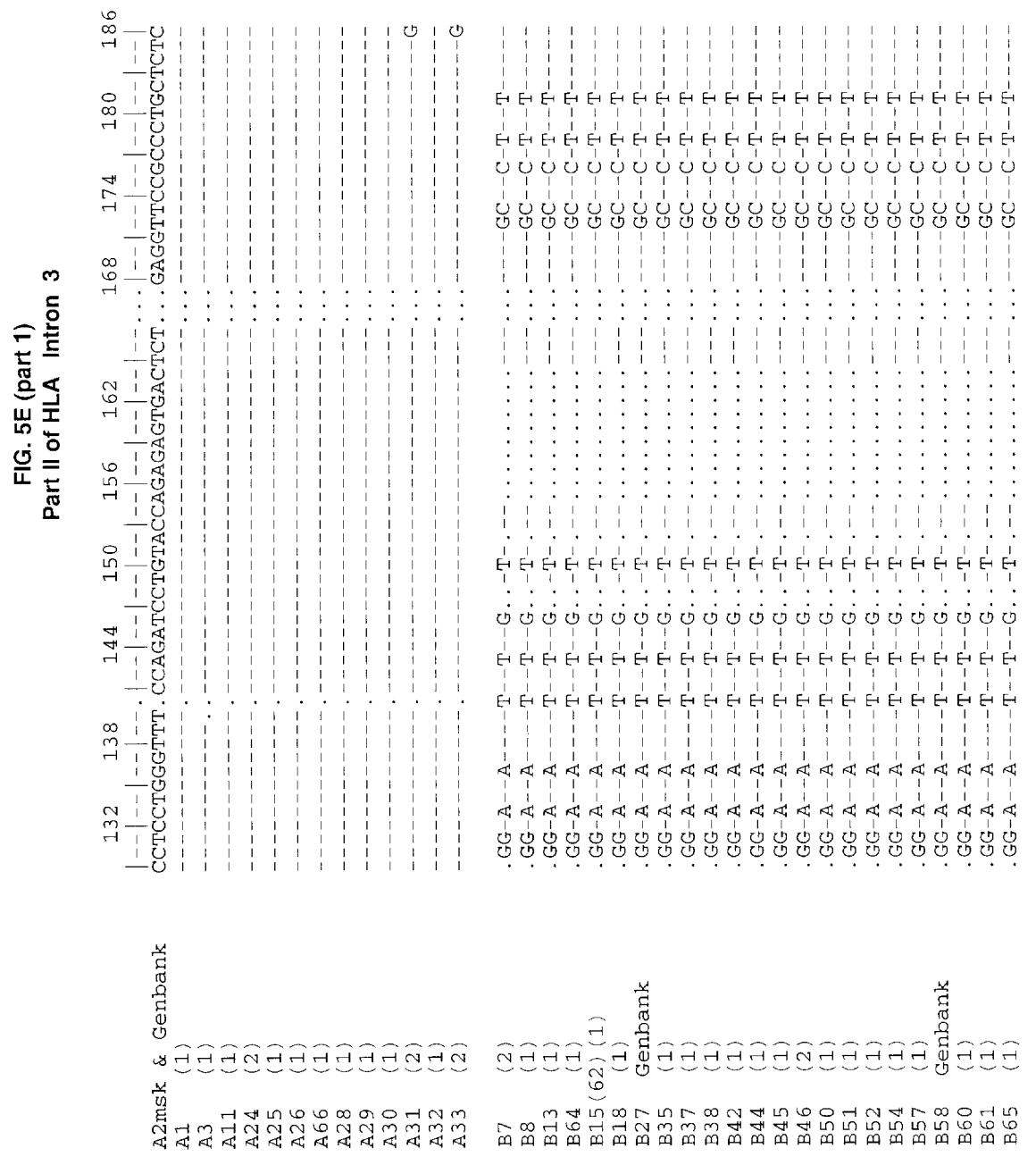

FIGS. 2, 3 and 4 shows combined sequences (Seq. ID Nos. : 1–9) for introns 1, 2 and 3 respectively, together with suitable locations for binding amplification primers. These sequences are consensus sequences derived from the individual aligned sequences determined for each intron as shown in FIGS. 5A–5H. In these sequences, bases which are the same for the locus across the various strains tested are indicated as a single base (A, C, G or T), while bases which were variable in the strains tested are indicated by a code for alternative bases. In general, it will be advantageous to select primers to avoid the variable bases, although in some of the primers discussed below, intra-locus variation is taken into account.

The method of the invention can be performed on whole blood, tumor cells, sperm, hair follicles or any other nucleated tissue sample.

Once the sample is obtained, the next step is to treat the tissue sample to obtain nucleic acids for amplification. Genomic DNA preparation suitable for amplification can be obtained by proteinase K digestion, as previously described in Levine et al., *Tissue Antigens* 44: 174–183 (1994). Briefly, this method involves removal of red cells in the case of blood samples after lysing by a hypotonic solution and then the remaining white cells are treated with Proteinase K in a detergent-containing solution to release DNA from nuclei and digest proteins in the cell lysate. After inactivation of the proteinase K, the remaining DNA in the solution is used as an amplification template. Other methods for preparing genomic DNA which may also be used in accordance with the invention include salting-out extraction procedures (Miller S, Dykes D, and Polesky H., "A simple salting out procedure for extracting DNA from human nucleated cells" Nucleic Acids Res. 16: 1215, 1988) and the standard phenol-chloroform DNA extraction procedure (Current Protocols in Molecular Biology, Series ed. K. Jansson, Wiley Interscience).

Once the sample has been treated, it is combined with two amplification primers and amplified, for example using Polymerase Chain Reaction (PCR) amplification. The basic process of PCR amplification is known, for example from U.S. Pats. Nos. 4,683,202 and 4,683,195, which are incorporated herein by reference. In PCR amplification, two amplification primers are used, each of which hybridizes to a different one of the two strands of a DNA duplex. Multiple cycles of primer extension, and denaturation are used to produce additional copies of DNA extending from the position of one primer to the position of the other. In this way, the number of copies of the genetic material positioned between the two primer binding sites is increased.

In the present invention, amplification of exons 2 and 3 is preferably performed using at least one locus-specific primer which specifically hybridizes to a portion of intron 1 or intron 3. As used in the specification and claims hereof, the primers which "specifically hybridize" to the introns are primers which permit locus-specific amplification by having a sequence which is exactly complementary to the expected sequence of a portion of the intron so that binding and amplification can occur, but which is not complementary to a region on any of the other HLA Class I genes. It will be understood that locus-specific primers within the scope of this invention need not be complementary to a totally unique sequence within the human genome, provided that both members of the primer pair used in amplification do not bind to the same gene outside the gene of interest.

The second amplification primer is preferably one which hybridizes with the other flanking intron (i.e., intron 3 when the first primer hybridizes to intron 1 and vice versa), since this will result in the simultaneous amplification of both exons 2 and 3. It will be appreciated, however, that exons 2 and 3 could be amplified individually by selecting a second amplification primer for exon 2 and a first primer for exon 3 which hybridize with intron 2 (Seq. ID Nos.: 2, 5 and 8), and such amplifications are within the scope of the invention.

Amplification primers useful in the present invention are generally from 10 to 40 bases in length, more preferably from 21 to 35 bases in length. Within this size range, we have identified suitable locus-specific, group specific and allele-specific primers for each of the classical HLA Class I genes.

For locus-specific amplification of the HLA-A gene, suitable locus-specific primers have the sequence

```
GGCCTCTGYG GGGAGAAGCA A          SEQ ID NO.: 10
or
GAAACSGCCT CTGYGGGGAG AAGCC      SEQ ID NO.: 11
```

Degenerate bases can be introduced in the primer sequences where alternative bases occur among alleles. These primers are complementary to the region of the non-coding strand spanning nucleotides 26–46 and 21–45, respectively of the intron 1 sequence shown in FIG. 2 (Seq. ID No.: 1). It will be appreciated that this primer could be made longer by adding additional complementary bases to the 5'-end. The primer might also be made somewhat shorter, for example spanning nucleotides 26–44, since nucleotides 23, 24 and 25 are identical across the various HLA-locuses in sequences of which the inventors are aware. In addition to primers binding to the non-coding strand, it will be appreciated that complementary primers which bind to the corresponding portions of the coding strand could be used with a compatible second primer. The use of longer or shorter locus-specific primers, and of complementary locus-specific primers are within the scope of the present invention.

Locations of these and additional primers within each of introns 1, 2, and 3 are shown in FIGS. 2, 3 and 4.

An amplification primer which binds to the non-coding strand of the HLA-A gene is used in combination with a second amplification primer which binds to the coding strand to achieve locus specific amplification. Preferably, both primers will be locus-specific in their hybridization to the HLA gene, although to achieve locus specific amplification only one of the two primers used to amplify DNA from the sample is required to be a locus-specific primer. Examples of locus-specific amplification primers which bind to the coding strand of the HLA-A gene include

```
CGGGAGATCT AYAGGCGATC AGG        SEQ ID No.: 12,
TGTTGGTCCC AATTGTCTCC CCTC       SEQ ID No.: 13, and
AGGATTCCTC TCCCTCAGGA CCAG       SEQ ID No.: 14.
```

These primers bind to the region of the coding strand of intron 3 of the HLA-A gene (SEQ ID No.: 3) spanning nucleotides 25–47, 65–88 and 108–131, respectively, as shown in FIG. 4. As in the case of the first amplification primer, amplification primers which are a made a few bases longer by virtue of adding additional complementary bases, amplification primers which are a few bases shorter, and complementary amplification primers may be used in the method of the present invention. Other potential sites for HLA-A locus specific primers are highlighted in FIG. 4.

The amplification primers and the genomic DNA are combined in an amplification mixture, for example containing 10 to 100 ng of genomic DNA in a 100 $\mu$l volume containing 0.2 mM dNTPs, the two primers at a concentration of 0.2 $\mu$M each, 2.5 units of Taq polymerase, 50 mM Tris-HCl (pH 8.8), 50 $\mu$M EDTA, 1.5 iM MgCl$_2$, 0.01% (w/v) gelatin, 10 mM β-mercaptoethanol and 10% (w/v) DMSO. The mixture is denatured at a temperature of 96° C. of 5 minutes. Multiple cycles, for example thirty cycles, of amplification are then performed. For HLA-A, -B and -C a suitable cycle program is

| denaturation | 94° C. | 22 seconds |
|---|---|---|
| annealing | 65° C. | 50 seconds |
| extensions | 72° C. | 30 seconds. |

Different cycling conditions may be used to obtain good PCR yields from longer or shorter primers.

While PCR amplification is the preferred approach to amplification of the treated sample, other techniques which use oligonucleotide primers to define a region of DNA to be amplified can be used as well. Such techniques include ligase chain reaction amplification (Wiedmann et al., PCR Primer, Laboratory Manual, Cold Spring Harbor (1991)).

The amplification procedure results in the production of an amplified product, in which the region of the HLA-A gene between the two primers is significantly increased in concentration relative to other genetic material in the treated sample. The amplified product is then evaluated to determine the allelic type of the HLA gene. This evaluation step can utilize any procedure which results in identification of allelic type.

For example, the amplification product can be evaluated by hybridization with locus-specific, group-specific or allele-specific oligonucleotide probes. Probes of this type which bind to the HLA-A gene are known in the art, for example from Oh et al., *Tissue Antigens* 41 : 135–142 (1993) and Bugawan et al., *Tissue Antigens* 44 : 137–147 (1994).

Oligonucleotide probes can be used in any of a number of test formats. For example, a dot blot analysis can be performed as described in Examples 1–3 below. Briefly, in this analysis the amplified product is affixed to a solid support in an array of dots. Labeled probes of different types are then applied to the dots. After washing to remove unhybridized probes, each dot is evaluated for the presence of hybridized (bound) probe using the label.

Other hybridization test formats may also be used. For example, the amplification primers used may be labeled with a detectable label, e.g., a radiolabel, a colored or chromogenic label, or a fluorescent or fluorogenic label; or an immobilization moiety such a biotin. The probes are then labeled with a complementary type of label, i.e., immobilizing when the amplification primers have a detectable label, and a detectable label when the amplification primers are immobilizable. The probes and the amplification products are combined under hybridizing conditions before or after immobilization of the immobilizable component of the reaction on a solid support, and the capture of the labeled component onto the solid support is monitored. Suitable solid supports include chromatographic columns and magnetic beads. Specific examples of suitable probes are listed in Table 1.

reactions mixtures, one for each type of dideoxy nucleotide base, by gel electrophoresis, the sequence of the complementary strand can be deduced.

TABLE 1

| SEQ ID No. | Probe * = noncoding | Sequence | First Codon Pos. | Specificity |
|---|---|---|---|---|
| 62 | 131R | CGCTCTTGGA CCGCG | 131 | A, L |
| 63 | HBB034 | GTTCGTGAGG TTCGACAGC | 32 | B |
| 64 | HYB035 | CGCCGTGGGT GGAGCAGGA | 49 | B*5401, C, G, L |
| 65 | EE2-210 | GCACAGACAC GGAACACC | 71 | E |
| 66 | FE2-200* | GTCTGTGCGT TGGCCTTG | 67 | F |
| 67 | GE2-183 | GAGGAGACAC GGAACACC | 62 | G, L |
| 68 | HE3-479* | TCCACGAACT CGCCCTCC | 158 | H |
| 69 | JE3-274* | TTCCCTGGAG GATGTGAT | 92 | J, K |
| 70 | HLB032 | CAGCGACTCC GTGAGTCCG | 37 | L |
| 71 | 142IK | CAGATCACCA AGCGC | 141 | A1, A3, A11, A24, A36, H |
| 72 | 114EH | TATGAACAGC ACGCC | 113 | A30, H |
| 73 | HXC008 | CTGCGGATCG CGCTCCGCT | 78 | A23, A24, A25, A32, B*2702, B38, B49, B51, B52, B53, B17, H |
| 74 | HBB055 | CCGCGAGTCC GAGGATGGC | 40 | B15, B46, B57, |
| 75 | HBC009 | CTGCGGACCC TGCTCCGCT | 78 | B27, B37, B47, J, K, L |
| 76 | HYE024 | GGACCTGCGC TCCTGGACC | 128 | B7, B8, B*2707, B40, B41, B42, B*4801, all Cw's except Cw3, Cw4, and Cw14, E, F, G, H, J, K, L |
| 77 | HBD080 | CGGGTACCAC CAGGACGCC | 111 | B27, B47 |
| 78 | HBD083 | CGGGTATGAC CAGGACGCC | 111 | B44 |
| 79 | HBD086 | CGGGTATAAC CAGTTAGCC | 111 | B45, B49, B50 |
| 80 | HBF094 | GACAAGCTGG AGCGCGCTG | 177 | B7, B*4001, B*4802 |
| 81 | HBC065 | GAAGTACAAG CGCCAGGCA | 65 | B46 |
| 82 | HBC066 | GAACATGAAG GCCTCCGCG | 65 | B57, B58 |
| 83 | 156R | GCGGAGCAGC GGAGAGCC | 153 | B7, B*3508, B*5702, Cw1, Cw*0401, Cw*0802, Cw14 |

The amplification product may also be evaluated using direct sequencing as described in Santamaria et al., *Hum. Immunology* 37 : 39–50 (1993). The amplified product can be sequenced using the well-known dideoxy chain termination method. Briefly, in this method a sequencing primer complementary to one strand of the amplified product is combined with the amplified product, a template-dependent polymerase enzyme, a mixture of the four standard nucleotide bases (A, G, T, and C) and one type of dideoxy nucleotide base. The bases are added to the end of the amplification primer to form a new oligonucleotide complementary to the amplification product. When a dideoxy base is added, however, no additional bases can be added. This results in the formations of a family of oligonucleotides whose lengths reflect the positions of the nucleotide base provided in dideoxy form within the complementary oligonucleotide. By evaluating the fragments formed in four reactions mixtures, one for each type of dideoxy nucleotide base, by gel electrophoresis, the sequence of the complementary strand can be deduced.

Basic procedures for performing nucleic acid sequencing in this manner are well known in the art, and commercial instruments are available for this purpose. Thus, sequencing is a routine procedure provided that amplified DNA and suitable primers are available. In this case, the same primers used to amplify the DNA can be used as sequencing primers.

Nested intron primers can also be used as sequencing primers. These primers are complementary to the sequences of the amplified products located in intron 1, intron 2 or intron 3 (SEQ ID Nos.: 1–9). It is particularly advantageous to have "universal" sequencing primers which could be used in the sequencing of any of the major transplantation antigen genes after locus-specific amplification, and such primers are an aspect of the present invention.

Examples of universal primers for sequencing the non-coding strand of the exon 2 which are complementary to the non-coding strand of intron 1 include:

GGGTCKGKYR GRTYTCAGC          SEQ ID No.: 15

CGCSCMKGGA SGWGGGTC           SEQ ID No.: 16.

These primers are complementary to the portion of intron 1 spanning nucleotides 95–113 and 82–99, respectively.

An example of a universal primer for sequencing the non-coding strand of the exon 2 which is complementary to the non-coding strand of the exon 2 is TCYCACTCCA TGAGGTATTT C          SEQ ID No.: 17.

This primer is complementary to the portion of exon 2 spanning nucleotides 3–23.

Examples of universal primers for sequencing of the coding strand of the exon 2 which are complementary to the coding strand of intron 2 include:

GGCYGGGGTC ACTCACCG              SEQ ID No.: 18 and

GTCSTGACCT SCGCCCC AGG           SEQ ID No.: 19.

These primers are complementary to the portion of intron 2 spanning nucleotides −2 to 15 and 19–35, respectively.

Examples of universal primers for sequencing of the non-coding strand of the exon 3 which are complementary to the non-coding strand of the intron 2 include:

GCGGGRCGGG GCTCGGGG              SEQ ID No.: 20 and

ATYCCCSCRG KTTGGTC               SEQ ID No: 21.

These primers are complementary to the portion of intron 2 spanning nucleotides 214–236 and 194–210, respectively.

An example of a universal primer for sequencing of the coding strand of the exon 3 which is complementary to the coding strand of the intron 3 is CCCYRYKGCC CCTGGTAC              SEQ ID No: 22.

This primer is complementary to the portion of intron 3 spanning nucleotides 1 to 18.

Other potential sequencing primer sites are highlighted in FIGS. 2, 3 and 4. In addition, the primers disclosed in U.S. Pat. No. 5,424,184 for sequencing of the HLA-A locus may also be used.

The amplified DNA products may also be evaluated by agarose gel electrophoresis for typing HLA alleles, for example using the techniques described in Browning et al., *Hum. Immunology* 39: 143 (1994); Krausa et al., *Lancet* 341: 121–122 (1993). Briefly, in this method each group of alleles or individual allele is amplified by a group-specific or an allele-specific primer pair exactly matched to that group or allele. By keeping the PCR conditions stringent, the primer pairs will not non-specifically amplify other related alleles. The amplification primers are designed with the specificity-dependent nucleotide(s) on the terminal 3'-prime end. Identification of the alleles is based on the absence or presence of amplified products observed after agarose gel electrophoresis.

The same procedures described above can be used in accordance with the invention to determine the type of HLA-B and HLA-C genes in a sample. For typing the HLA-B gene, an exemplary locus-specific first amplification primer has the sequence GGGAGGAGCG AGGGGACCSC AG         SEQ ID No.: 23

This amplification primer is complementary to the region of the non-coding strand spanning nucleotides 36–57 of the intron 1 sequence (Seq ID No.: 4) of the HLA-B gene shown in FIG. 2. Primers might also be derived from the di-allelic site spanning nucleotides 57–76, for example CGGGGGCGCA GGACCCGG              SEQ ID No.: 24 or

GGCGGGGCG CAGGACCTGA             SEQ ID No.: 25 which span nucleotides 59–76 and 57–76, respectively.

As in the case of the locus-specific primers for HLA-A, it will be appreciated that this primer could be made longer by adding additional complementary bases to either or both ends. The amplification primer might also be made somewhat shorter, for example spanning nucleotides 39–57 in the case of Seq ID No.: 23, since nucleotides 38, 39 are identical across the HLA-genes of which the inventors are aware, although this may result in the loss of some discrimination between HLA-B and HLA-C genes if nucleotide 37 (which is different in HLA-C genes from HLA-A and HLA-B) is not spanned by the probe. In addition, complementary amplification primers which bind to the corresponding portions of the coding strand could be used with a compatible second primer. The use of such longer or shorter primers and of complementary primers is within the scope of the present invention.

Exemplary locus-specific second amplification primers which can be used in typing the HLA-B gene using the method of the invention have the sequence:

GGAGGCCATC CCCGGCGACC T          SEQ ID No.: 26, and

GGAGGCCATC CCCGGCGACC TAT        SEQ ID No.: 27,

These primers bind to the region of the coding strand of intron 3 of the HLA-B gene (SEQ ID No.: 6) spanning nucleotides 38–58, 36–58, respectively, as shown in FIG. 4. As in the case of the first amplification primer, amplification primers which are a made a few bases longer by virtue of adding additional complementary bases, amplification primers which are a few bases shorter, particularly those which span nucleotides 40–50, and complementary amplification primers may be used in the method of the present invention.

The primers

SEQ ID No.: 28;
CTCAGGAAAA CTCATSCCAT TCTCCATTC AAC and

SEQ ID No.: 29
GGAGATGGGG AAGGCTCCCC ACT which bind to the region of the coding strand of intron 3 of the HLA-B gene (SEQ ID No.: 6) spanning nucleotides 106–137 and 12–34, respectively, can also be used for amplification of the HLA gene, although this primer also amplifies HLA-C.

Other locus-specific, group-specific or allele specific oligonucleotides which are complementary to the non-coding strand of introns 1 and 2 of the HLA-B gene and which can be used in the method of the invention are indicated in FIGS. 2 and 3. Similarly, other locus-specific, group-specific or allele specific oligonucleotides which are complementary to the coding strand of introns 2 and 3 of the HLA-B gene and which can be used in the method of the invention are indicated in FIGS. 3 and 4. Any of these oligonucleotides can be used in combination the locus-specific primers for locus-specific amplification, although the use of two-locus specific amplification primers is preferred. These oligonucleotides can also be used as sequencing primers for typing of the HLA-B gene, although the universal primers described above (SEQ ID Nos.: 15–22) are preferred.

Suitable probes for use in hybridization assays of the type of the amplified product made using these primers are Ragupathi et al., *Tissue Antigens* 46 : 24–31 (1995), Fernandez-Vina et al., *Tissue Antigens* 45: 153–168 (1995); and in Fleischhauer et al., *Tissue Antigens* 46: 281–292 (1995) and are listed in Table 1.

For typing the HLA-C gene, the suitable locus-specific first amplification primers have the sequences:

```
AGCGAGGXGC CCGCCCGGCG A        SEQ ID No.: 30,

GAGGGAAACG GCCTCTGCGG A        SEQ ID No.: 31,

GAGGGGCCCG CCCGGCGA            SEQ ID No.: 32, or

GACCCGGGGA GCCGCGGCA           SEQ ID No.: 33.
```

These locus-specific amplification primers are complementary to the region of the non-coding strand spanning nucleotides 42 to 62 (SEQ ID No.: 30), 17–37 (SEQ ID No.: 31), 45–62 (SEQ ID No.: 32) and 71–88 (SEQ ID No.: 33)of intron 1 of the HLA-C gene sequence (SEQ ID No.: 7) as shown in FIG. 2. It will be appreciated that these amplification primers could be made longer by adding additional complementary bases to either or both ends. The amplification primer might also be made somewhat shorter. The nucleotides complemen- tary to nucleotides 34 and 37 for SEQ ID NO.: 31, 56 and 61 for SEQ ID NO.: 32, and 78 and 87 for SEQ ID NO.: 33 should be retained in the amplification primer, since these bases are distinct in the HLA-C intron from both HLA-A and HLA-B. In addition, complementary amplification primers which bind to the corresponding portions of the coding strand could be used with a compatible second amplification primer. The use of such longer or shorter amplification primers and of complementary amplification primers is within the scope of the present invention.

Suitable locus specific second amplification primers which are compatible to the coding strand include:

```
CGCTGATCCC ATTTTCCTCC CCTC         SEQ ID NO.: 34,

GGAGATGGGG AAGGCTCCCC ACT          SEQ ID NO.: 29,

SEQ ID NO.: 35,
CTCAGGAAAA TCATGSCCAT TCTCCATTCA AG

ACCACAGCTG CTGCAGTGGT CAAAGTG      SEQ ID NO.: 36,
```

-continued

```
GAGGAAAGGT CAGCAGCCTG ACCACA       SEQ ID NO.: 37, or

GACTCAGAAA AGCTGGAATC AAACCTT      SEQ IDSEQ ID
                                   NO.: 37,
```

These locus-specific amplification primers bind to the region of the coding strand of intron 3 of the HLA-C gene (SEQ ID No.: 9) spanning nucleotides 65–88 (SEQ ID NO.: 34), 12–34 (SEQ ID No.: 29), 106–137 (SEQ ID No.: 35), 267–291 (SEQ ID NO.: 36), 283–304 (SEQ ID NO.: 37), 342–368 (SEQ ID NO.: 38), respectively, as shown in FIG. 4. As in the case of the first amplification primers, amplification primers which are a made a few bases longer by virtue of adding additional complementary bases, amplification primers which are a few bases shorter, and complementary amplification primers may be used in the method of the present invention. The primers SEQ ID Nos.: 28, and 29 39 are specific for both B and C loci, therefore this primers can be used for HLA-C amplification when it is paired with an HLA-C-locus-specific 5' primer such as SEQ ID NO.: 31, SEQ ID NO.: 32, or SEQ ID NO.: 33.

Suitable probes for use in hybridization assays of the type of the amplified product made using these amplification primers are described in Levine et al. *Tissue Antigens* 44: 174–183 (1994) and in Table 1.

A further aspect of the present invention is determination of the allelic type of the non-classical Class I genes, i.e., HLA-E, -F, -G, -H, -J, -K and -L. In this case, the primers which we have identified as providing the most unique locus specific amplification for this purpose are located with exon 2 and exon 3 of the respective HLA gene. These locus specific amplification primers are used in the same general manner as the amplification primers discussed above for HLA-A, with specific differences being noted below.

For typing the HLA-E gene, the first amplification primer has the sequence

```
CACTCCTTGA AGTATTTCCA CACT         SEQ ID NO.: 41 or

TGGAAACGGC CTCTACCGGG AGTAGAG      SEQ ID NO.: 42.
```

SEQ ID No.: 41 is complementary to the region of the non-coding strand spanning nucleotides 6–29 of exon 2 (SEQ ID No.: 39) of the HLA-E gene sequence shown in FIG. 6. SEQ ID No.: 42 is complementary to the region of the non-coding strand spanning nucleotides 19-45 of intron 1 of the HLA-E gene sequence (SEQ ID No.: 43).

It will be appreciated that these amplification primers could be made longer by adding additional complementary bases to either or both ends. The amplification primer might also be made somewhat shorter, for example spanning at least nucleotides 6–12 for SEQ ID No.: 41. Nucleotides complementary to nucleotides 24 and 29 for SEQ ID No.: 41 and 38–44 for SEQ ID NO.: 42 are also advantageously retained in a locus-specific primer since these bases are distinct in the HLA-E gene sequence from the rest of the genes. In addition, complementary amplification primers which bind to the corresponding portions of the coding strand could be used with a compatible second amplification primer. The use of such longer or shorter amplification primers and of complementary amplification primers is within the scope of the present invention.

Exemplary second amplification primers used in typing the HLA-E gene using the method of the invention have the sequence

TCTCCTTCCC CTTCTCCAGG TATT        SEQ ID NO.: 44 or

CACAGTCCTA GCCCAAGAAG GAGATGGGAG AGTA        SEQ ID NO.: 45.

SEQ ID No.: 44 primer binds to the region of the coding strand of exon 3 of the HLA-E gene (SEQ ID No.: 40) spanning nucleotides 238–261 as shown in FIG. 7. SEQ ID No.: 45 primer binds to the region of the coding strand of intron 3 of the HLA-E gene (SEQ ID No.: 46) spanning nucleotides 19–53. As in the case of the first amplification primer, amplification primers which are a made a few bases longer by virtue of adding additional complementary bases, amplification primers which are a few bases shorter (retaining the 3'-end), and complementary amplification primers may be used in the method of the present invention.

Amplification of the HLA-E gene is performed using the same general methodology described for amplification of HLA-A, -B and -C genes. The cycle program in this case, however, is preferably

| denaturation | 94° C. | 22 seconds |
| annealing | 62° C. | 50 seconds |
| extensions | 72° C. | 30 seconds. |

Suitable probes for use in hybridization assays of the type of the amplified product made using these amplification primers are listed in Table 1.

For typing the HLA-F gene, the first amplification primer has the sequence

AGGTATTTCA GCACCGCTGT GTCG        SEQ ID NO.: 47 or

GTGAGTGCGG GGTCCAGAGA        SEQ ID NO.: 48.

SEQ ID No.: 47 amplification primer is complementary to the region of the non-coding strand spanning nucleotides 15–38 of exon 2 of the HLA-F gene sequence (SEQ ID No.: 39). SEQ ID No.: 48 amplification primer is complementary to the region of the non-coding strand spanning nucleotides 1–20 of intron 1 of the HLA-F gene sequence (SEQ ID No.: 49) shown in FIG. 2. It will be appreciated that these amplification primer could be made longer by adding additional complementary bases to either or both ends. The amplification primer might also be made somewhat shorter, for example spanning at least nucleotides 15–20 for SEQ ID No.: 47. The nucleotides complementary to nucleotides 24, 25, 30, 32 and 38 for SEQ ID No.: 47 and 15, 16, 19, and 20 for SEQ ID No.: 48 are also advantageously retained in a locus-specific amplification primer, since these bases are distinct in the HLA-F sequence from the rest of the genes. In addition, complementary amplification primers which bind to the corresponding portions of the coding strand could be used with a compatible second amplification primer. The use of such longer or shorter amplification primers and of complementary amplification primers is within the scope of the present invention.

Examples of the second amplification primer used in typing the HLA-F gene using the method of the invention have the sequence

GCGTCTCCTT CCCATTCTCC AA        SEQ ID NO.: 50 or

CAACCTTGTG CGAGGCCATC CCA        SEQ ID No.: 51.

SEQ ID No.: 50 amplification primer binds to the region of the coding strand of exon 3 of the HLA-F gene (SEQ ID No.: 40) spanning nucleotides 243–264. SEQ ID No.: 51 amplification primer binds to the region of the coding strand of intron 3 of the HLA-F gene (SEQ ID No.: 52) spanning nucleotides 46–68. As in the case of the first amplification primer, amplification primers which are a made a few bases longer by virtue of adding additional complementary bases, amplification primers which are a few bases shorter (retaining the 3'-end), and complementary amplification primers may be used in the method of the present invention.

Amplification of the HLA-F gene is performed using the same methodology described for amplification of HLA-A, -B and -C genes, and the same cycle program described for amplification of the HLA-E gene.

Suitable probes for use in hybridization assays of the type of the amplified product made using these amplification primers are listed in Table 1.

For typing the HLA-G gene, the first amplification primer has, for example, the sequence

GGTTCGACAG CGACTCGGCG T        SEQ ID NO.: 53 or

CGGCGGGGGC GCAGGACTCG GCA        SEQ ID NO.: 54.

SEQ ID NO.: 53 amplification primer is complementary to the region of the non-coding strand spanning nucleotides 103–123 of exon 2 of the HLA-G gene sequence (SEQ ID No.: 39). SEQ ID NO.: 54 amplification primer is complementary to the region of the non-coding strand spanning nucleotides 56–78 of intron 1 of the HLA-G gene sequence (SEQ ID No.: 55). It will be appreciated that this amplification primer could be made longer by adding additional complementary bases to either or both ends. The amplification primer might also be made somewhat shorter. The nucleotides complementary to nucleotides 119, 120 and 123 for SEQ ID NO.: 53 and 79 and 80 for SEQ ID No.: 54 are advantageously retained in a locus-specific amplification primer, since these bases are distinct in the HLA-G sequence from the rest of the genes. In addition, complementary amplification primers which bind to the corresponding portions of the coding strand could be used with a compatible second amplification primer. The use of such longer or shorter amplification primers and of complementary amplification primers is within the scope of the present invention.

Suitable oligonucleotides for use as the second amplification primer used in typing the HLA-G gene using the method of the invention have the sequence

```
TCTCCTTCCC GTTCTCCAGG T                SEQ ID NO.: 56
``` or

```
TCCTCCTCTC CTTGTGCTAG GCCAGGCTG        SEQ ID NO.: 57.
```

SEQ ID NO.: 56 amplification primer binds to the region of the coding strand of exon 3 of the HLA-G gene (SEQ ID No.: 40) spanning nucleotides 241–261. This region is the same in HLA-G, -H, -J, -K, and -L genes, and the same primer can be used as a second primer in each of the amplifications. SEQ ID NO.: 36 amplification primer binds to the region of the coding strand of exon 3 of the HLA-G gene (SEQ ID No.: 40) spanning nucleotides 46–74. Slightly longer, shorter, and complementary primers can also be used.

Amplification of the HLA-G gene is performed using the same general methodology described for amplification of HLA-A, -B and -C genes. In this case, however the amplification is performed in a glycerol buffer, rather than a DMSO buffer. Thus, each reaction mixture contains 10 to 100 ng of genomic DNA in a 100 μl volume containing 0.2 mM dNTPs, the two amplification primers at a concentration of 0.2 μM each, 2.5 units of Taq polymerase, 10 mM Tris-HCl (pH 8.8), 1.5 mM $MgCl_2$, 0.001% (w/v) gelatin, 50 mM KCl and 7.5% (w/v) glycerol. The cycle program for amplification in this case is preferably

| denaturation | 94° C. | 22 seconds |
|---|---|---|
| annealing | 60° C. | 50 seconds |
| extensions | 72° C. | 30 seconds. |

Suitable probes for use in hybridization assays of the type of the amplified product made using these amplification primers are listed in Table 1.

For typing the HLA-H gene, a suitable first amplification primer has the sequence

```
GAGCCCCGCT TCATCTCCGT C                SEQ ID NO.: 58.
```

This amplification primer is complementary to the region of the non-coding strand spanning nucleotides 54–74 of exon 2 of the HLA-G gene sequence (SEQ ID No.: 39). It will be appreciated that this amplification primer could be made longer by adding additional complementary bases to either or both ends. The amplification primer might also be made somewhat shorter. The nucleotides complementary to nucleotides 69, 71 and 74 for SEQ ID No.: 58 are advantageously retained in a locus-specific amplification primer, since these bases are distinct in the HLA-H sequence from the rest of the genes. In addition, complementary amplification primers which bind to the corresponding portions of the coding strand could be used with a compatible second amplification primer. The use of such longer or shorter amplification primers and of complementary amplification primers is within the scope of the present invention.

The second amplification primer used in typing the HLA-H gene is the same as that used for HLA-G (SEQ ID NO.: 56). Alternative second amplification primers can be made from nucleotides which include nucleotides 485 (G), 486 (A) and 490 (T) in exon 3 or nucleotides 28(G) and 33(G) in intron 3.

Amplification of the HLA-H gene is performed using the same general methodology described for amplification of HLA-A, -B and -C genes in DMSO buffer. The cycle program for amplification in this case is preferably

| denaturation | 94° C. | 22 seconds |
|---|---|---|
| annealing | 58° C. | 50 seconds |
| extensions | 72° C. | 30 seconds. |

Suitable probes for use in hybridization assays of the type of the amplified product made using these amplification primers are listed in Table 1.

For typing the HLA-J gene, the first amplification primer has the sequence

```
AGCACCGCCG TTTCCTGGCC G                SEQ ID NO.: 59
```

This amplification primer is complementary to the region of the non-coding strand spanning nucleotides 24–44 of exon 2 of the HLA-C gene sequence (SEQ ID No.: 39). It will be appreciated that this amplification primer could be made longer by adding additional complementary bases to either or both ends. The amplification primer might also be made somewhat shorter. The nucleotides complementary to nucleotides 30, 35, 39, and 44 for SEQ ID NO. 59 are advantageously retained in a locus specific amplification primer, since these bases are distinct in the HLA-J sequence from the rest of the genes. In addition, complementary amplification primers which bind to the corresponding portions of the coding strand could be used with a compatible second amplification primer. The use of such longer or shorter amplification primers and of complementary amplification primers is within the scope of the present invention.

The second amplification primer used in typing the HLA-J gene is the same as that used for HLA-G (SEQ ID NO.: 56).

Amplification of the HLA-J gene is performed using the same methodology described for amplification of the HLA-G gene.

Suitable probes for use in hybridization assays of the type of the amplified product made using these amplification primers are listed in Table 1.

For typing the HLA-K gene, the first amplification primer has the sequence

```
ACTCCATAAG GTAGTTCAGC ACCGCC          SEQ ID NO.: 60
```

This amplification primer is complementary to the region of the non-coding strand spanning nucleotides 7–32 of exon 2 of the HLA-K gene sequence (SEQ ID No.: 39). It will be appreciated that this amplification primer could be made longer by adding additional complementary bases to either or both ends. The amplification primer might also be made somewhat shorter, for example spanning at least nucleotides 7–15. In addition, complementary amplification primers which bind to the corresponding portions of the coding strand could be used with a compatible second amplification primer. The use of such longer or shorter amplification primers and of complementary amplification primers is within the scope of the present invention.

The second amplification primer used in typing the HLA-K gene is the same as that used for HLA-G (SEQ ID NO.: 56).

Amplification of the HLA-K gene is performed using the same methodology described for amplification of the HLA-G gene.

Suitable probes for use in hybridization assays of the type of the amplified product made using these amplification primers are listed in Table 1.

For typing the HLA-L gene, the first amplification primer has the sequence

GTGCGGTTCG ACAGCGACTC CGT        SEQ ID NO.: 61

This amplification primer is complementary to the region of the non-coding strand spanning nucleotides 99–121 of exon 2 of the HLA-L gene sequence (SEQ ID No.: 39). It will be appreciated that this amplification primer could be made longer by adding additional complementary bases to either or both ends. The amplification primer might also be made somewhat shorter. The nucleotides complementary to nucleotides 117 and 121 for SEQ ID No.: 61 are advantageously retained in the locus-specific amplification primer, since these bases are distinct in the HLA-L sequence from the rest of the genes. In addition, complementary amplification primers which bind to the corresponding portions of the coding strand could be used with a compatible second amplification primer. The use of such longer or shorter amplification primers and of complementary amplification primers is within the scope of the present invention.

The second amplification primer used in typing the HLA-L gene is the same as that used for HLA-C (SEQ ID NO.: 56).

Amplification of the HLA-L gene is performed using the same methodology described for amplification of the HLA-G gene.

Suitable probes for use in hybridization assays of the type of the amplified product made using these amplification primers are listed in Table 1.

The primers used in the determination of HLA type in accordance with the invention can be made by any of the methods known in the art, and indeed companies now exist which will make a desired oligonucleotide to order. Examples of suitable synthetic approaches for primers include the phosphoramidite method.

The amplification primers which are themselves an aspect of the invention may be modified using methods known in the art to include a detectable label or a capture moiety such as biotin. For example, a fluorophore can be added to the 5'-terminus of a primer by synthesizing the oligonucleotide with a 5'-aliphatic amino group and then coupling the amino group to an activated dye precursor. The 3'-terminus of an last oligonucleotide can be labeled using Terminal deoxynucleotidyl transferase to add a single extra fluorescently-labeled nucleotide from a fluorescent dideoxy(NTP) precursor. All necessary reagents for this 3'- labeling procedure are available commercially. (ABI, Boehringer, Clontech). Such labeled primers may be useful as sequencing primers for determining the sequence of the amplified portion of the gene.

Amplification primers in accordance with the invention may be advantageously packaged in kits for the typing of tissue samples. Such kits may contain, for example, at least one pair of amplification primers, including at least one locus-specific amplification primer, effective to amplify at least one HLA Class I gene. In addition the kits may include some or all of the following:

(1) one or more reagents for the amplification of the HLA gene using the primers, e.g., a polymerase enzyme, a buffer, and individual nucleotide bases;

(2) one or more sequencing primers suitable for sequencing exons 2 and 3 of the gene(s) amplified by the primer pair(s), together with optional sequencing reagents such as polymerase;

(3) one or more sequence-specific oligonucleotide probes useful for determining the HLA type of the gene(s) amplified by the primer pair(s); and (4) reagents for sample preparation. Such kits may also include instructions for carrying out the tissue preparation and typing, containers, dot blot membranes or other solid supports for hybridization assays.

EXAMPLE 1

Genomic DNA was prepared from samples of each of 106 cell lines of the cell panel of the 10th International Histocompatibility Workshop using proteinase K digestion as described by Levine et al., *Tissue Antigens* 44 : 174–183 (1994). The name and HLA-A, HLA-B and HLA-C types of each of these cell lines is listed in FIG. 8.

A portion of each prepared sample was amplified using one of the probe combinations described above, i.e, for HLA-A Seq ID Nos.: 11 and 13;

for HLA-B Seq ID Nos.: 23 and 26; and for HLA-C Seq ID Nos.: 30 and 29;

for HLA-E Seq ID Nos.: 41 and 44 for HLA-F Seq ID Nos.: 47 and 50 for HLA-G Seq ID Nos.: 53 and 56 for HLA-H Seq ID Nos.: 58 and 56 for HLA-J Seq ID Nos.: 59 and 56 for HLA-K Seq ID Nos.: 60 and 56 for HLA-L Seq ID Nos.: 61 and 56 under the conditions described above. The amplified products were then applied to a positively charged nylon membrane (Boehringer Mannheim, Germany) using an eight channel syringe. After air-drying for one hour, DNA dotted on the membrane was denatured in 0.4 M NaOH. After neutralization, DNA was UV cross-linked to the membrane by exposing it for 5 minutes in a Stratalinker 2400 (Stratagene).

Oligonucleotide probes as shown in Table 1s were 3'-end labeled with digoxigenin-ddUTP (Boehringer Mannheim) in accordance with the manufacturers instructions. The membranes were then hybridized with digoxigenin-ddUTP labeled oligonucleotide probes (1 pmol/ml hybridization solution) of the types for one hour. The hybridization was conducted at 46° C. for 15-mer probes and 54° C. for 18-mer probes. The membranes were then washed in TMAC at 54° C. and 58° C., respectively, for 20 minutes. Washed membranes were treated with anti-digoxigenin Fab antibody conjugated to alkaline phosphatase (Boehringer Mannheim) after treatment with blocking agent in accordance with the manufacturers protocol. The washed and treated membranes were then treated with Lumiphos 480 (Life Codes, Stamford CT) according to the manufacturers instructions and imaged using Kodak X-Omat X-Ray film for 1 to 60 minutes.

A first set of membranes was used to test the locus specificity of the amplification primers of the invention using locus-specific probes. In this set of tests, each membrane had amplifications products for each locus on it as shown in Table 2.

TABLE 2

PROTOCOL FOR LOCUS SPECIFICITY TEST

| GENE | CELL LINES TESTED |
|---|---|
| HLA-A | 1, 2, 5, 6, 7, 8, 9, 10, 13, 14, 16, 19, 22, 29, 35, 50, 53, 58, 64, 66, 71, 106, 107, NEGATIVE CONTROL |
| HLA-B | SAME AS HLA-A |
| HLA-C | SAME AS HLA-A |
| HLA-E | 24, 25, 26, 28, 30, 41, 48, 55 |
| HLA-F | 13, 14, 16, 19, 22, 29, 35, 50 |
| HLA-G | SAME AS HLA-F |
| HLA-H | 63, 64, 65, 66, 67, 68, 69, 70 |
| HLA-J | SAME AS HLA-F |
| HLA-K | 7, 13, 16, 19, 22, 29, 35, 50 |
| HLA-L | SAME AS HLA-F |

These membranes were hybridized with probes 131R (and HLA-A and HLA-A specific probe); HBB034 (an HLA-B specific probe) HYB035 (HLA-C, G, L and B54 specific); EE2-210 (HLA-E specific); FE2-200 (HLA-F specific) GE3-183 (HLA-G specific) HE3-479 (HLA-H specific); JE3-274 (HLA-J and -K specific); and HLB032 (HLA-L specific).

Probe 131 R showed positive hybridization with all cell lines amplified with the HLA-A specific probes and all cell lines except cell line 35 and 50 amplified with the HLA-L specific probes; and no positive hybridization results with any other amplification products.

Probe HBB034 showed positive hybridization with all cell lines amplified with the HLA-B specific probes; and no positive hybridization results with any other amplification products.

Probe HYB035 showed positive hybridization with all cell lines except cell lines 35 and 107 amplified with the HLA-C specific probes and all cell lines except cell line 35 amplified with the HLA-G or K specific probes. One false positive hybridization result was noted for cell line 107 amplified with the HLA-B specific probes. This is consistent with published sequence data which shows that the cell line carries the HLA-Cw consensus sequence in the site from which HBB034 was derived.

Probe EE2-210 showed positive hybridization with all cell lines amplified with the HLA-E specific probes; and no positive hybridization results with any other amplification products.

Probe FE2-200 showed positive hybridization with all cell lines amplified with the HLA-F specific probes; and no positive hybridization results with any other amplification products.

Probe CE3-183 showed positive hybridization with all cell lines amplified with the HLA-B specific probes. False positive hybridization results were also obtained for all cell lines amplified with the HLA-L specific probes.

Probe HE3-479 showed positive hybridization with all cell lines amplified with the HLA-H specific probes; and no positive hybridization results with any other amplification products.

Probe JE3-274 showed positive hybridization with all cell lines amplified with the HLA-J and K specific probes; and no positive hybridization results with any other amplification products.

Probe HLB032 showed positive hybridization with all cell lines amplified with the HLA-L specific probes; and no positive hybridization results with any other amplification products. This probe can therefore be used to confirm a positive result obtained using GE3-183.

EXAMPLE 2

A second experiment was performed using membranes prepared in accordance with Example 1, except that the membranes were dotted with the amplification products from all 106 cell lines shown in FIG. 7. The membranes also contained a panel of amplification products from the non-classical genes, as follows:

| Gene | Cell Lines |
|---|---|
| HLA-E | 4, 5, 6, |
| HLA-F | 19, 20, 21 |
| HLA-G | 33, 34 |
| HLA-H | 49, 50, 51 |
| HLA-J | 64, 65, 66 |
| HLA-K | 79, 80, 81 |
| HLA-L | 94, 95, 96 |

In this experiment, HLA-A specific probes 114 EH and 142 IK were hybridized with membranes dotted with amplification products formed using the HLA-A specific primers plus the non-classical panel; and HLA-B specific probes HYE024, HXC008, HBC009 and HBB055 were hybridized with membranes dotted with amplification products formed using the HLA-B specific primers plus the non-classical panel.

On all of the membranes, a positive hybridization result was obtained for every cell lines which met the known specificity of the probe, as set forth in Table 2. No positive results were detected for cell lines with different allelic types. Thus, locus-specific amplification is achieved using the primer combinations of the invention.

EXAMPLE 3

Three additional membranes were prepared in accordance with the protocols in Example 1. The first membrane was dotted with samples for all 106 cell lines amplified with generic (not locus-specific) HLA amplification primers having the sequence

| | |
|---|---|
| GGCYGGGGTC ACTCACCG | SEQ ID NO.: 18 |
| and | |
| TGCAGCGTCT CCTTCCCGTT | SEQ ID No.: 84 |

The second was dotted with samples for all 106 cell lines amplified with the HLA-B specific amplification primers Seq ID Nos.: 3 and 4 of the invention. The third was dotted with samples for all 106 cell lines amplified with the HLA-C specific amplification primers Seq ID Nos.: 5 and 6 of the invention. These membranes were then hybridized with probe 156R which binds to several HLA-B and HLA-C allelic types.

The membrane dotted with generic amplification products revealed no specificity, with all cell lines producing a positive hybridization result. In contrast, with HLA-B amplified fragments, the probe reacted only with amplified products from cell lines 1, 13, 17, 33, 34, 42, 65, 81, 82 and 83, the cell lines which have allelic types recognized by the 156R probe. On the membrane dotted with HLA-C amplified fragments, the probe showed a positive hybridization reaction with all samples carrying Cw1, Cw4, Cw5, Cw8 and Cwl4 but not with those with other HLA-C allelic types. This test further demonstrates the locus specificity of the amplification procedure of the invention.

We claim:

1. A method for testing a tissue sample to determine the allelic type of an HLA Class I gene in the sample, said HLA Class I gene being selected from among HLA-A, HLA-B and HLA-C genes comprising the steps of
   (a) treating the tissue sample to obtain nucleic acid polymers suitable for amplification;
   (b) combining the nucleic acid polymers with a first primer which hybridizes with a portion of intron 1 or intron 3 of the HLA Class I gene, and a second primer which hybridizes with a different portion of the HLA Class I gene conditions suitable for amplification to obtain an amplified product, wherein the first primer and the second primer flank a region including at least one site of allelic variation in at least one of exons 2 or 3 of the HLA Class I gene and wherein the first primer is a locus specific primer which hybridizes with intron 1 or intron 3 of only one of the HLA Class I genes; and
   (c) evaluating the amplified product to determine the allelic type of the HLA-Class I gene.

2. The method of claim 1, wherein the first primer hybridizes with intron 1 and the second primer hybridizes with intron 3 of the selected HLA Class I gene.

3. The method of claim 2, wherein at least one of the first primer and the second primer specifically hybridizes with the selected HLA Class I gene to provide locus-specific amplification.

4. The method of claim 2, wherein the HLA Class I gene is an HLA-A gene, and the first primer is an oligonucleotide which is complementary to or has the same sequence as a portion of SEQ ID No.: 1.

5. The method of claim 2, wherein the HLA Class I gene is an HLA-A gene, and the first primer is an oligonucleotide which is complementary to or has the same sequence as a portion of SEQ ID No.: 3.

6. The method of claim 2, wherein the HLA Class I gene is an HLA-B gene, and the first primer is an oligonucleotide which is complementary to or has the same sequence as a portion of SEQ ID No.: 4.

7. The method of claim 2, wherein the HLA Class I gene is an HLA-B gene, and the first primer is an oligonucleotide which is complementary to or has the same sequence as a portion of SEQ ID No.: 6.

8. The method of claim 2, wherein the HLA Class I gene is an HLA-C gene, and the first primer is an oligonucleotide which is complementary to or has the same sequence as a portion of SEQ ID No.: 7.

9. The method of claim 2, wherein the HLA Class I gene is an HLA-C gene, and the first primer is an oligonucleotide which is complementary to or has the same sequence as a portion of SEQ ID No.: 9.

10. The method of claim 1, wherein the amplified product is evaluated using sequence specific oligonucleotide probes which hybridize selectively to known alleles of the HLA gene.

11. The method of claim 1, wherein the amplified product is evaluated by direct sequencing.

12. The method of claim 11, wherein the amplified product is sequenced using a sequencing primer which hybridizes to all of the classical HLA Class I genes.

13. The method of claim 1, wherein the first amplification primer is any of the primers identified by SEQ ID Nos.: 10–14 and 23–38.

14. The method of claim 1, further comprising the step of testing a portion of the nucleic acid polymers from the sample to determine the type of at least one non-classical HLA Class I genes.

15. The method of claim 12, wherein the step of testing the portion of the nucleic acid polymers includes the steps of
   combining the portion of the nucleic acid polymers with a first non-classical primer which specifically hybridizes with a portion of the non-classical HLA Class I gene, and a second non-classical primer which hybridizes with a different portion of the non-classical HLA Class I gene under conditions suitable for amplification to obtain an amplified non-classical product; and
   (c) evaluating the amplified non-classical product to determine the allelic type of the non-classical HLA-Class I gene.

16. The method of claim 15, wherein the first or second non-classical primer is any of the primers identified by SEQ ID Nos.: 41, 42, 45, 47, 48, 50, 51, 53, 54, and 56 to 61.

17. A method for preparing an amplification primer pair for locus-specific amplification of exons 2 and 3 of a selected classical HLA Class I gene comprising the steps of:
   (a) evaluating the aligned sequences of intron 1 of the classical HLA Class I gene to select an intron 1 sequence of from 10 to 40 bases which differs in the selected gene from unselected classical HLA Class I genes;
   (b) scanning the known sequences of the selected and unselected classical HLA Class I genes to determine if the selected intron 1 sequence is repeated elsewhere within the genes and selecting a new intron 1 sequence if repetition is found;
   (c) evaluating the aligned sequences of intron 3 of the classical HLA Class I gene to select an intron 3 sequence of from 10 to 40 bases which differs in the selected gene from unselected classical HLA Class I genes;
   (d) scanning the known sequences of the selected and unselected classical HLA Class I genes to determine if the selected intron 3 sequence is repeated elsewhere within these genes and selecting a new intron 3 sequence if repetition is found; and
   (e) synthesizing a pair of primers having the sequences of the selected intron 1 and intron 3 sequences.

18. The method of claim 17, further comprising the step of performing a test amplification using the synthesized primers and testing the amplification products with sequence specific probes to confirm locus specificity.

19. A kit for testing a tissue sample to determine the allelic type of an HLA Class I gene in the sample comprising, in packaged combination, at least one pair of amplification primers, said pair of amplification primers including a first primer which hybridizes with a portion of intron 1 or intron 3 of the HLA Class I gene and a second primer which hybridizes with a different portion of the HLA Class I gene under conditions suitable for amplification to obtain an amplified product, wherein the first primer and the second primer flank a region including at least one site of allelic variation in at least one of exons 2 or 3 of the HLA Class I gene and wherein the first primer is a locus specific primer which hybridizes with intron 1 or intron 3 of only one of the HLA Class I genes.

20. The kit of claim 19, wherein the first primer is a locus-specific primer which specifically hybridizes with one and only one of the HLA Class I genes.

21. The kit of claim 20, wherein the HLA Class I gene is an HLA-A gene, and the first primer specifically hybridizes with or is the same as a continuous portion of SEQ ID NO.: 1, 2 or 3.

22. The kit of claim 20, wherein the HLA Class I gene is an HLA-B gene, and the first primer specifically hybridizes with or is the same as a continuous portion of SEQ ID NO.: 4, 5 or 6.

23. The kit of claim 20, wherein the HLA Class I gene is an HLA-C gene, and the first primer specifically hybridizes with or is the same as a continuous portion of SEQ ID NO.: 7, 8 or 9.

24. The kit of claim 20, further comprising at least one separate container containing a sequence-specific oligonucleotide probe which hybridizes selectively to a known allele of the HLA gene.

25. A method for testing a tissue sample to determine the allelic type of an HLA Class I gene in the sample, said HLA Class I gene being selected from among the non-classical HLA genes comprising the steps of (a) treating the tissue sample to obtain nucleic acid polymers suitable for amplification;

(b) combining the nucleic acid polymers with a locus-specific first primer which specifically hybridizes with a portion of the non-classical HLA Class I gene, and a second primer which hybridizes with a different portion of the non-classical HLA Class I gene under conditions suitable for amplification to obtain an amplified non-classical product; and (c) evaluating the amplified non-classical product to determine the allelic type of the non-classical HLA Class I gene.

26. The method of claim 25, wherein the locus-specific first primer is any of the primers identified by SEQ ID Nos.: 41, 42, 45, 47, 48, 50, 51, 53, 54, and 57 to 61.

27. The method of claim 25, wherein the second primer has the sequence given by SEQ ID No.: 56.

* * * * *

SEQUENCE LISTING (1) GENERAL INFORMATION:

(iii) NUMBER OF SEQUENCES: 84

(2) INFORMATION FOR SEQ ID NO: 1:

(i) SEQUENCE CHARACTERISTICS:
       (A) LENGTH: 130
       (B) TYPE: nucleic acid
       (C) STRANDEDNESS: double
       (D) TOPOLOGY: linear (ii) MOLECULE TYPE: Genomic DNA (iii) HYPOTHETICAL:no (iv) ANTI-SENSE: no (v) FRAGMENT TYPE: internal (vi) ORIGINAL SOURCE:
       (A) ORGANISM: human (ix) FEATURE:
       (D) OTHER INFORMATION: consensus sequence of intron 1 of the
           HLA-A gene (xi) SEQUENCE DESCRIPTION: SEQ ID NO:1:

GTGAGTGCGG GGTCGKGAGG GAAACSGCCT CTGYGGGGAG AAGCAASGGG                50

CCCKCCYGGC GGGGRCGCAR GACCSGGGDA GCCGCGCCKG GASGAGGGTC               100

GGKYRGRTCT CAGCCWCTSC TCGYCCCCAG                                     130

(2) INFORMATION FOR SEQ ID NO: 2:

(i) SEQUENCE CHARACTERISTICS:
       (A) LENGTH: 242
       (B) TYPE: nucleic acid
       (C) STRANDEDNESS: double
       (D) TOPOLOGY: linear (ii) MOLECULE TYPE: Genomic DNA (iii) HYPOTHETICAL:no (iv) ANTI-SENSE: no (v) FRAGMENT TYPE: internal (vi) ORIGINAL SOURCE:
       (A) ORGANISM: human (ix) FEATURE:
       (D) OTHER INFORMATION: consensus sequence of intron 2 of the
           HLA-A gene (xi) SEQUENCE DESCRIPTION: SEQ ID NO:2:

GTGAGTGACC CCRGCCSGGG GCGCAGGTCA SGACCYCTCA TCCCCCACGG                50

ACGGGCCRGG TSCRCCCACA GTCTCCGGGT CCGAGATCCR CCCCGAAGCC               100

GCGGGACYCC GAGACCCTTG HCCCGGGAGA GGCCCAGGCG CCTTWACCCG               150

GTTTCATTTT CAGTTTAGGC CAAAAATYCC CCCRGGTTGG TCGGGGCBGG               200

RCRGGGCTYG GGGGACYGGG CTGACCKYGG GGTCSGGGCC AG                       242

(2) INFORMATION FOR SEQ ID NO: 3:

(i) SEQUENCE CHARACTERISTICS:

(A) LENGTH: 600
        (B) TYPE: nucleic acid
        (C) STRANDEDNESS: double
        (D) TOPOLOGY: linear (ii) MOLECULE TYPE: Genomic DNA (iii) HYPOTHETICAL:no (iv) ANTI-SENSE: no (v) FRAGMENT TYPE: internal (vi) ORIGINAL SOURCE:
        (A) ORGANISM: human (ix) FEATURE:
        (D) OTHER INFORMATION: consensus sequence of intron 3 of the
            HLA-A gene (xi) SEQUENCE DESCRIPTION: SEQ ID NO:3:

```
GTACCAGGGG CCACRGRGCG CCTMCCTGAT CGCCTRTAGR TCTCCCGGGC           50

TGGCCTCCCA CAAGGAGGGG AGACAWTTGG GACCAACACT AGAATATCRC          100

CCTCCCTCTG GTCCTGAGGG AGAGGAMTCC TCCTGGGTTT CCAGATCCTG          150

TACCAGAGAG TGACTCTGAG GTTCCGCCCT GCTCTSTGAC WCAATTAAGG          200

GATAAAATCT CTGAMGGART GACGGDAAGA CGATCCCTCG AATACTGATG          250

ASTGGTTCCC TTTGACACAC ACMGGCAGSA GCCTTGGGMC CGTGACTTTT          300

CCTCTCAGGC CTTGTTCTCT GCTTCACACT CAATGTGTGT GGGGGTCTGA          350

GTCCAGCACT TCTGAGTCYY TCAGCCTCCA CTCAGGTCAG GACCAGAAGT          400

CGCTGTTCCC TYYTCAGGGA MTAGAATTTT CCACGGAATA GGAGATTATC          450

CCAGGTGCCT GTGTCCAGGC TGGTGTCTGG GTTCTGTGCT CYCTTCCCCA          500

TCCCRGGTGT SCTGTCCATT CTCAAGATRG SCACATGYRT GCTGGWGGAG          550

TGTCCCATKA CAGATRCMMA ATGCCTGMAT KWTCTGACTC TTCCYGWCAG          600
```

(2) INFORMATION FOR SEQ ID NO: 4:

(i) SEQUENCE CHARACTERISTICS:
        (A) LENGTH: 129
        (B) TYPE: nucleic acid
        (C) STRANDEDNESS: double
        (D) TOPOLOGY: linear (ii) MOLECULE TYPE: Genomic DNA (iii) HYPOTHETICAL:no (iv) ANTI-SENSE: no (v) FRAGMENT TYPE: internal (vi) ORIGINAL SOURCE:
        (A) ORGANISM: human (ix) FEATURE:
        (D) OTHER INFORMATION: consensus sequence of intron 1 of the
            HLA-B gene (xi) SEQUENCE DESCRIPTION: SEQ ID NO:4:

```
GTGAGTGCGG GRTCGGSAGG GAAATGGCCT CTGYVGGGAG GAGMGAGGGG           50

ACCTCAGGCG GGGGCGCAGG ACCYGRGGAG CCGCGCCGGG AGGAGGGTCK          100

GGCGGGTYTC AGCYCCTCCT BRCCCCCAG                                 129
```

(2) INFORMATION FOR SEQ ID NO: 5:

(i) SEQUENCE CHARACTERISTICS:
  (A) LENGTH: 252
  (B) TYPE: nucleic acid
  (C) STRANDEDNESS: double
  (D) TOPOLOGY: linear (ii) MOLECULE TYPE: Genomic DNA (iii) HYPOTHETICAL:no (iv) ANTI-SENSE: no (v) FRAGMENT TYPE: internal (vi) ORIGINAL SOURCE:
  (A) ORGANISM: human (ix) FEATURE:
  (D) OTHER INFORMATION: consensus sequence of intron 2 of the
   HLA-B gene (xi) SEQUENCE DESCRIPTION: SEQ ID NO:5:

```
GTGAGTGACC CCGGCCYGGG GCGSAGGTCA CGACTCCCCA TCCCCCACGK        50

ACGGBCCGGG TCGCCCCGAG TCTCCGGGTC CGAGATCCRM CYCCCTGAGG       100

CYGSGGGAMC CGCCCAKACC CTCGACCGGM GAGAGCCSCA GGCGCGTTTA       150

CCCGGTTTCA TTTTCAGTTG AGGCCAAAAA TCCCCGCGGG TTGGKCRGGG       200

CGGGGCGGGG CGGGGCTCGG GGGGACKGKG CTGWCCGCGG GGBSKGGKCC       250

AG                                                          252
```

(2) INFORMATION FOR SEQ ID NO: 6:

(i) SEQUENCE CHARACTERISTICS:
  (A) LENGTH: 575
  (B) TYPE: nucleic acid
  (C) STRANDEDNESS: double
  (D) TOPOLOGY: linear (ii) MOLECULE TYPE: Genomic DNA (iii) HYPOTHETICAL:no (iv) ANTI-SENSE: no (v) FRAGMENT TYPE: internal (vi) ORIGINAL SOURCE:
  (A) ORGANISM: human (ix) FEATURE:
  (D) OTHER INFORMATION: consensus sequence of intron 3 of the
   HLA-B gene (xi) SEQUENCE DESCRIPTION: SEQ ID NO:6:

```
GTACCAGGGG CAGTGGGGAG CCTBCCCCAT CTCCTATAGG TCGSCGGGGA        50

TGGSCTCCMA CGAGAAGARG AGGAAAATGG GATCAGCGCT AGAATGTCGC       100

CCTCCCTTGA ATGGAGAATG GCATGAGTTT TCCTGAGTTT CCTCTGAGGG       150

CCCCCTCTTC TCTCTAGGAC AATTARGGRA TGACGTCTCT GAGGAAATGG       200

AGGGGAAGWC AGYCCCTAGR ATASTGATCA GGGGTCCYCT TTGACCCCTG       250

CAGCAGCCTT GGGAACCRTG ACTTTTCYTC TCAGRCCTTG TTCTCTGCCT       300

CACACTCAGT GTGTTTGGGG CTCTGATTCC AGYACTTCTG AGTCACTTTA       350

CCTCCACTCA GATCRGGAGC AGAAGTCYCT GTTCCCCGCT CAGAGACTCG       400
```

```
AACTTTCCAA TGAATAGGAG ATTATCCCAG GTGCCTGCRT CCAGGCTGGT        450

GTCTGGGTTC TGTGYCCCTT CCCCACMCCA GGTGTCCTGY CCATTCTCAG        500

KCTGGTCACA TGGGTGGTCC TAGGGTGTSC CATGARAGAT GCMAAGCGCC        550

TGWAWTTTCT GACTCTTCCC ATCAG                                  575
```

(2) INFORMATION FOR SEQ ID NO: 7:

(i) SEQUENCE CHARACTERISTICS:
        (A) LENGTH: 130
        (B) TYPE: nucleic acid
        (C) STRANDEDNESS: double
        (D) TOPOLOGY: linear (ii) MOLECULE TYPE: Genomic DNA (iii) HYPOTHETICAL:no (iv) ANTI-SENSE: no (v) FRAGMENT TYPE: internal (vi) ORIGINAL SOURCE:
        (A) ORGANISM: human (ix) FEATURE:
        (D) OTHER INFORMATION: consensus sequence of intron 1 of the
            HLA-C gene (xi) SEQUENCE DESCRIPTION: SEQ ID NO:7:

```
GTGAGTGCGR GGTTRGGAGG GAADCGGCCT CTGSGGAGAG GARCGAGGKG        50

CCCKCCCGGC GAGGGCGCAG GACCCGGGGA GCCGCGCAGG GAGGWGGGTC        100

GGGCGGGTCT CAGCCMCTCC TCKYCCCCAG                             130
```

(2) INFORMATION FOR SEQ ID NO: 8:

(i) SEQUENCE CHARACTERISTICS:
        (A) LENGTH: 252
        (B) TYPE: nucleic acid
        (C) STRANDEDNESS: double
        (D) TOPOLOGY: linear (ii) MOLECULE TYPE: Genomic DNA (iii) HYPOTHETICAL:no (iv) ANTI-SENSE: no (v) FRAGMENT TYPE: internal (vi) ORIGINAL SOURCE:
        (A) ORGANISM: human (ix) FEATURE:
        (D) OTHER INFORMATION: consensus sequence of intron 2 of the
            HLA-C gene (xi) SEQUENCE DESCRIPTION: SEQ ID NO:8:

```
GTGAGTGACC CCRGCCCGGG GCGCAGGTCA CGACCCCCCC YCATCCCCCA        50

CGGACGGCCC GGGTCGCCCC RAGTCTCCSS GTCTGAGATC CACCCCAAGG        100

TGGATCTGCG GAACCCGCCC AGACCCTCGA CCGGAGAGAG CCCYAGTCRC        150

CTTTACCCGG TTTCATTTTC RGTTTAGGCC AAAAATCCCC GCSGKTTGGT        200

CGGGRCKGGG GCGGGGCTCG SGGGACKGKG YTGACCRCGG GGGCGGSGCC        250

AG                                                           252
```

(2) INFORMATION FOR SEQ ID NO: 9:

(i) SEQUENCE CHARACTERISTICS:
        (A) LENGTH: 587
        (B) TYPE: nucleic acid
        (C) STRANDEDNESS: double
        (D) TOPOLOGY: linear (ii) MOLECULE TYPE:Genomic DNA (iii) HYPOTHETICAL:no (iv) ANTI-SENSE: no (v) FRAGMENT TYPE: internal (vi) ORIGINAL SOURCE:
        (A) ORGANISM: human (ix) FEATURE:
        (D) OTHER INFORMATION: consensus sequence of intron 3 of the
            HLA-C gene (xi) SEQUENCE DESCRIPTION: SEQ ID NO:9:

```
GTACCAGGGG CAGTGGGGAG CCTTCCCCAT CTCCYRTAGA TCTCCCGGSA           50

TGGCCTCCCA CGAGGAGGGG AGGAAAATGG GATCAGCGCT RGAATATCGC          100

CCTCCCTTGA ATGGAGAATG GSATGAGTTT TCCYGAGTTT CYTCTGARGG          150

CCCCSTCTGC TCTCTAGGAC AATTAAGGGA TGAAGTCYYT GAGGAAATGG          200

AGGGGAAGAC AGTCCCTRGA ATACTGATCA GGGGTCYCCT TTGACCACTT          250

TGACCACTGC RGCAGCTGTG GTCAGGCTGC TGACCTTTCT CTCAGGCCTT          300

GTTCTCTGCC TCAYRYTCAA TGTGTYTRAA GGTTTGATTC CAGCTTTTCT          350

GAGTYCTKCR GCCTCCACTC AGGTCAGGAC CAGAAGTCGC TGTTCCTCCC          400

TCAGAGACTA GAACTTTCCA AWGAATAGGA GATTATCCCA GGTSCCTGTG          450

TCCAGGCTGG CGTCTGGGTT CTGTGCCSCC TTCCCYACCC CAGGTGTCCT          500

GTCCRTTCTC AGGATRGTCA CATGGSCRCT GYTGGAGTGT CSCAAGAGAG          550

AWRCAAAGTG TCTGAATTTT CTGACTCTTC CCGTCAG                        587
```

(2) INFORMATION FOR SEQ ID NO: 10:

(i) SEQUENCE CHARACTERISTICS:
        (A) LENGTH: 21
        (B) TYPE: nucleic acid
        (C) STRANDEDNESS: double
        (D) TOPOLOGY: linear (ii) MOLECULE TYPE: other nucleic acid (iii) HYPOTHETICAL:no (iv) ANTI-SENSE: no (v) FRAGMENT TYPE: internal (vi) ORIGINAL SOURCE:
        (A) ORGANISM: human (ix) FEATURE:
        (D) OTHER INFORMATION: intron 1 primer for locus specific
            amplification of exons 2 and 3 of HLA-A gene (xi) SEQUENCE DESCRIPTION: SEQ ID NO:10:

```
GGCCTCTGYG GGGAGAAGCA A                                          21
```

(2) INFORMATION FOR SEQ ID NO: 11:

(i) SEQUENCE CHARACTERISTICS:
            (A) LENGTH: 25
            (B) TYPE: nucleic acid
            (C) STRANDEDNESS: double
            (D) TOPOLOGY: linear (ii) MOLECULE TYPE: other nucleic acid (iii) HYPOTHETICAL:no (iv) ANTI-SENSE: no (v) FRAGMENT TYPE: internal (vi) ORIGINAL SOURCE:
            (A) ORGANISM: human (ix) FEATURE:
            (D) OTHER INFORMATION: intron 1 primer for locus specific
                amplification of exons 2 and 3 of HLA-A gene (xi) SEQUENCE DESCRIPTION: SEQ ID NO:11:

GAAACSGCCT CTGYGGGGAG AAGCC                                             25

(2) INFORMATION FOR SEQ ID NO: 12:

(i) SEQUENCE CHARACTERISTICS:
            (A) LENGTH: 23
            (B) TYPE: nucleic acid
            (C) STRANDEDNESS: double
            (D) TOPOLOGY: linear (ii) MOLECULE TYPE: other nucleic acid (iii) HYPOTHETICAL:no (iv) ANTI-SENSE: yes (v) FRAGMENT TYPE: internal (vi) ORIGINAL SOURCE:
            (A) ORGANISM: human (ix) FEATURE:
            (D) OTHER INFORMATION: intron 3 primer for locus specific
                amplification of exons 2 and 3 of HLA-A gene (xi) SEQUENCE DESCRIPTION: SEQ ID NO:12:

CGGGAGATCT AYAGGCGATC AGG                                               23

(2) INFORMATION FOR SEQ ID NO: 13:

(i) SEQUENCE CHARACTERISTICS:
            (A) LENGTH: 24
            (B) TYPE: nucleic acid
            (C) STRANDEDNESS: double
            (D) TOPOLOGY: linear (ii) MOLECULE TYPE: other nucleic acid (iii) HYPOTHETICAL:no (iv) ANTI-SENSE: yes (v) FRAGMENT TYPE: internal (vi) ORIGINAL SOURCE:
            (A) ORGANISM: human (ix) FEATURE:
            (D) OTHER INFORMATION: intron 3 primer for locus specific
                amplification of exons 2 and 3 of HLA-A gene (xi) SEQUENCE DESCRIPTION: SEQ ID NO:13:

```
TGTTGGTCCC AATTGTCTCC CCTC                                              24
```

(2) INFORMATION FOR SEQ ID NO: 14:

(i) SEQUENCE CHARACTERISTICS:
        (A) LENGTH: 24
        (B) TYPE: nucleic acid
        (C) STRANDEDNESS: double
        (D) TOPOLOGY: linear (ii) MOLECULE TYPE: other nucleic acid (iii) HYPOTHETICAL:no (iv) ANTI-SENSE: yes (v) FRAGMENT TYPE: internal (vi) ORIGINAL SOURCE:
        (A) ORGANISM: human (ix) FEATURE:
        (D) OTHER INFORMATION: intron 3 primer for locus specific
            amplification of exons 2 and 3 of HLA-A gene (xi) SEQUENCE DESCRIPTION: SEQ ID NO:14:

```
AGGATTCCTC TCCCTCAGGA CCAG                                              24
```

(2) INFORMATION FOR SEQ ID NO: 15:

(i) SEQUENCE CHARACTERISTICS:
        (A) LENGTH: 19
        (B) TYPE: nucleic acid
        (C) STRANDEDNESS: double
        (D) TOPOLOGY: linear (ii) MOLECULE TYPE: other nucleic acid (iii) HYPOTHETICAL:no (iv) ANTI-SENSE: no (v) FRAGMENT TYPE: internal (vi) ORIGINAL SOURCE:
        (A) ORGANISM: human (ix) FEATURE:
        (D) OTHER INFORMATION: sequencing primer for exon 2 of HLA-A,
            -B or -C genes (xi) SEQUENCE DESCRIPTION: SEQ ID NO:15:

```
GGGTCKGKYR GRTYTCAGC                                                    19
```

(2) INFORMATION FOR SEQ ID NO: 16:

(i) SEQUENCE CHARACTERISTICS:
        (A) LENGTH: 18
        (B) TYPE: nucleic acid
        (C) STRANDEDNESS: double
        (D) TOPOLOGY: linear (ii) MOLECULE TYPE: other nucleic acid (iii) HYPOTHETICAL:no (iv) ANTI-SENSE: no (v) FRAGMENT TYPE: internal (vi) ORIGINAL SOURCE:
        (A) ORGANISM: human (ix) FEATURE:
              (D) OTHER INFORMATION: sequencing primer for exon 2 of HLA-A,
                  -B or -C genes (xi) SEQUENCE DESCRIPTION: SEQ ID NO:16:

CGCSCMKGGA SGWGGGTC                                                        18

(2) INFORMATION FOR SEQ ID NO: 17:

(i) SEQUENCE CHARACTERISTICS:
              (A) LENGTH: 21
              (B) TYPE: nucleic acid
              (C) STRANDEDNESS: double
              (D) TOPOLOGY: linear (ii) MOLECULE TYPE: other nucleic acid (iii) HYPOTHETICAL:no (iv) ANTI-SENSE: no (v) FRAGMENT TYPE: internal (vi) ORIGINAL SOURCE:
              (A) ORGANISM: human (ix) FEATURE:
              (D) OTHER INFORMATION: sequencing primer for exon 2 of HLA-A,
                  -B or -C genes (xi) SEQUENCE DESCRIPTION: SEQ ID NO:17:

TCYCACTCCA TGAGGTATTT C                                                    21

(2) INFORMATION FOR SEQ ID NO: 18:

(i) SEQUENCE CHARACTERISTICS:
              (A) LENGTH: 18
              (B) TYPE: nucleic acid
              (C) STRANDEDNESS: double
              (D) TOPOLOGY: linear (ii) MOLECULE TYPE: other nucleic acid (iii) HYPOTHETICAL:no (iv) ANTI-SENSE: yes (v) FRAGMENT TYPE: internal (vi) ORIGINAL SOURCE:
              (A) ORGANISM: human (ix) FEATURE:
              (D) OTHER INFORMATION: sequencing primer for exon 2 of HLA-A,
                  -B or -C genes (xi) SEQUENCE DESCRIPTION: SEQ ID NO:18:

GGCYGGGGTC ACTCACCG                                                        18

(2) INFORMATION FOR SEQ ID NO: 19:

(i) SEQUENCE CHARACTERISTICS:
              (A) LENGTH: 17
              (B) TYPE: nucleic acid
              (C) STRANDEDNESS: double
              (D) TOPOLOGY: linear (ii) MOLECULE TYPE: other nucleic acid (iii) HYPOTHETICAL:no (iv) ANTI-SENSE: yes (v) FRAGMENT TYPE: internal (vi) ORIGINAL SOURCE:
            (A) ORGANISM: human (ix) FEATURE:
            (D) OTHER INFORMATION: sequencing primer for exon 2 of HLA-A,
                -B or -C genes (xi) SEQUENCE DESCRIPTION: SEQ ID NO:19:

GTCSTGACCT SCGCCCC                                                          17

(2) INFORMATION FOR SEQ ID NO: 20:

(i) SEQUENCE CHARACTERISTICS:
            (A) LENGTH: 19
            (B) TYPE: nucleic acid
            (C) STRANDEDNESS: double
            (D) TOPOLOGY: linear (ii) MOLECULE TYPE: other nucleic acid (iii) HYPOTHETICAL:no (iv) ANTI-SENSE: no (v) FRAGMENT TYPE: internal (vi) ORIGINAL SOURCE:
            (A) ORGANISM: human (ix) FEATURE:
            (D) OTHER INFORMATION: sequencing primer for exon 3 of HLA-A,
                -B or -C genes (xi) SEQUENCE DESCRIPTION: SEQ ID NO:20:

GCGGGRCGGG GCTCGGGGG                                                        19

(2) INFORMATION FOR SEQ ID NO: 21:

(i) SEQUENCE CHARACTERISTICS:
            (A) LENGTH: 17
            (B) TYPE: nucleic acid
            (C) STRANDEDNESS: double
            (D) TOPOLOGY: linear (ii) MOLECULE TYPE: other nucleic acid (iii) HYPOTHETICAL:no (iv) ANTI-SENSE: no (v) FRAGMENT TYPE: internal (vi) ORIGINAL SOURCE:
            (A) ORGANISM: human (ix) FEATURE:
            (D) OTHER INFORMATION: sequencing primer for exon 3 of HLA-A,
                -B or -C genes (xi) SEQUENCE DESCRIPTION: SEQ ID NO:21:

ATYCCCSCRG KTTGGTC                                                          17

(2) INFORMATION FOR SEQ ID NO: 22:

(i) SEQUENCE CHARACTERISTICS:
            (A) LENGTH: 18
            (B) TYPE: nucleic acid
            (C) STRANDEDNESS: double
            (D) TOPOLOGY: linear (ii) MOLECULE TYPE: other nucleic acid

```
        (iii) HYPOTHETICAL:no (iv) ANTI-SENSE: yes (v) FRAGMENT TYPE: internal (vi) ORIGINAL SOURCE:
              (A) ORGANISM: human (ix) FEATURE:
              (D) OTHER INFORMATION: sequencing primer for exon 3 of HLA-A,
                  -B or -C genes (xi) SEQUENCE DESCRIPTION: SEQ ID NO:22:

CCCYRYKGCC CCTGGTAC                                                     18

(2) INFORMATION FOR SEQ ID NO: 23:

(i) SEQUENCE CHARACTERISTICS:
              (A) LENGTH: 22
              (B) TYPE: nucleic acid
              (C) STRANDEDNESS: double
              (D) TOPOLOGY: linear (ii) MOLECULE TYPE: other nucleic acid (iii) HYPOTHETICAL:no (iv) ANTI-SENSE: no (v) FRAGMENT TYPE: internal (vi) ORIGINAL SOURCE:
              (A) ORGANISM: human (ix) FEATURE:
              (D) OTHER INFORMATION: locus specific amplification primer for
                  HLA-B gene (xi) SEQUENCE DESCRIPTION: SEQ ID NO:23:

GGGAGGAGCG  AGGGGACCSC  AG                                              22

(2) INFORMATION FOR SEQ ID NO: 24:

(i) SEQUENCE CHARACTERISTICS:
              (A) LENGTH: 18
              (B) TYPE: nucleic acid
              (C) STRANDEDNESS: double
              (D) TOPOLOGY: linear (ii) MOLECULE TYPE: other nucleic acid (iii) HYPOTHETICAL:no (iv) ANTI-SENSE: no (v) FRAGMENT TYPE: internal (vi) ORIGINAL SOURCE:
              (A) ORGANISM: human (ix) FEATURE:
              (D) OTHER INFORMATION: locus specific amplification primer for
                  HLA-B gene (xi) SEQUENCE DESCRIPTION: SEQ ID NO:24:

CGGGGGCGCA GGACCCGG                                                     18

(2) INFORMATION FOR SEQ ID NO: 25:

(i) SEQUENCE CHARACTERISTICS:
              (A) LENGTH: 20
```

```
        (B) TYPE: nucleic acid
        (C) STRANDEDNESS: double
        (D) TOPOLOGY: linear (ii) MOLECULE TYPE: other nucleic acid (iii) HYPOTHETICAL:no (iv) ANTI-SENSE: no (v) FRAGMENT TYPE: internal (vi) ORIGINAL SOURCE:
        (A) ORGANISM: human (ix) FEATURE:
        (D) OTHER INFORMATION: locus specific amplification primer for
            HLA-B gene (xi) SEQUENCE DESCRIPTION: SEQ ID NO:25:

GGCGGGGCG CAGGACCTGA                                                       20

(2) INFORMATION FOR SEQ ID NO: 26:

(i) SEQUENCE CHARACTERISTICS:
        (A) LENGTH: 21
        (B) TYPE: nucleic acid
        (C) STRANDEDNESS: double
        (D) TOPOLOGY: linear (ii) MOLECULE TYPE: other nucleic acid (iii) HYPOTHETICAL:no (iv) ANTI-SENSE: yes (v) FRAGMENT TYPE: internal (vi) ORIGINAL SOURCE:
        (A) ORGANISM: human (ix) FEATURE:
        (D) OTHER INFORMATION: locus specific amplification primer for
            HLA-B gene (xi) SEQUENCE DESCRIPTION: SEQ ID NO:26:

GGAGGCCATC CCCGGCGACC T                                                    21

(2) INFORMATION FOR SEQ ID NO: 27:

(i) SEQUENCE CHARACTERISTICS:
        (A) LENGTH: 23
        (B) TYPE: nucleic acid
        (C) STRANDEDNESS: double
        (D) TOPOLOGY: linear (ii) MOLECULE TYPE: other nucleic acid (iii) HYPOTHETICAL:no (iv) ANTI-SENSE: yes (v) FRAGMENT TYPE: internal (vi) ORIGINAL SOURCE:
        (A) ORGANISM: human (ix) FEATURE:
        (D) OTHER INFORMATION: locus specific amplification primer for
            HLA-B gene (xi) SEQUENCE DESCRIPTION: SEQ ID NO:27:

GGAGGCCATC CCCGGCGACC TAT                                                  23
```

(2) INFORMATION FOR SEQ ID NO: 28:

(i) SEQUENCE CHARACTERISTICS:
        (A) LENGTH: 32
        (B) TYPE: nucleic acid
        (C) STRANDEDNESS: double
        (D) TOPOLOGY: linear (ii) MOLECULE TYPE: other nucleic acid (iii) HYPOTHETICAL:no (iv) ANTI-SENSE: yes (v) FRAGMENT TYPE: internal (vi) ORIGINAL SOURCE:
        (A) ORGANISM: human (ix) FEATURE:
        (D) OTHER INFORMATION: locus specific amplification primer for
            HLA-B gene (xi) SEQUENCE DESCRIPTION: SEQ ID NO:28:

CTCAGGAAAA CTCATSCCAT TCTCCATTCA AG                    32

(2) INFORMATION FOR SEQ ID NO: 29:

(i) SEQUENCE CHARACTERISTICS:
        (A) LENGTH: 23
        (B) TYPE: nucleic acid
        (C) STRANDEDNESS: double
        (D) TOPOLOGY: linear (ii) MOLECULE TYPE: other nucleic acid (iii) HYPOTHETICAL:no (iv) ANTI-SENSE: yes (v) FRAGMENT TYPE: internal (vi) ORIGINAL SOURCE:
        (A) ORGANISM: human (ix) FEATURE:
        (D) OTHER INFORMATION: amplification primer for HLA-B or HLA-C
            gene (xi) SEQUENCE DESCRIPTION: SEQ ID NO:29:

GGAGATGGGG AAGGCTCCCC ACT                           23

(2) INFORMATION FOR SEQ ID NO: 30:

(i) SEQUENCE CHARACTERISTICS:
        (A) LENGTH: 21
        (B) TYPE: nucleic acid
        (C) STRANDEDNESS: double
        (D) TOPOLOGY: linear (ii) MOLECULE TYPE: other nucleic acid (iii) HYPOTHETICAL:no (iv) ANTI-SENSE: no (v) FRAGMENT TYPE: internal (vi) ORIGINAL SOURCE:
        (A) ORGANISM: human (ix) FEATURE:
        (D) OTHER INFORMATION: locus specific amplification primer for
            HLA-C gene (xi) SEQUENCE DESCRIPTION: SEQ ID NO:30:

AGCGAGGKGC CCGCCCGGCG A                                              21

(2) INFORMATION FOR SEQ ID NO: 31:

(i) SEQUENCE CHARACTERISTICS:
        (A) LENGTH: 21
        (B) TYPE: nucleic acid
        (C) STRANDEDNESS: double
        (D) TOPOLOGY: linear (ii) MOLECULE TYPE: other nucleic acid (iii) HYPOTHETICAL:no (iv) ANTI-SENSE: no (v) FRAGMENT TYPE: internal (vi) ORIGINAL SOURCE:
        (A) ORGANISM: human (ix) FEATURE:
        (D) OTHER INFORMATION: locus specific amplification primer for
            HLA-C gene (xi) SEQUENCE DESCRIPTION: SEQ ID NO:31:

GAGGGAAACG GCCTCTGCGG A                                              21

(2) INFORMATION FOR SEQ ID NO: 32:

(i) SEQUENCE CHARACTERISTICS:
        (A) LENGTH: 18
        (B) TYPE: nucleic acid
        (C) STRANDEDNESS: double
        (D) TOPOLOGY: linear (ii) MOLECULE TYPE: other nucleic acid (iii) HYPOTHETICAL:no (iv) ANTI-SENSE: no (v) FRAGMENT TYPE: internal (vi) ORIGINAL SOURCE:
        (A) ORGANISM: human (ix) FEATURE:
        (D) OTHER INFORMATION: locus specific amplification primer for
            HLA-C gene (xi) SEQUENCE DESCRIPTION: SEQ ID NO:32:

GAGGGGCCCG CCCGGCGA                                                  18

(2) INFORMATION FOR SEQ ID NO: 33:

(i) SEQUENCE CHARACTERISTICS:
        (A) LENGTH: 18
        (B) TYPE: nucleic acid
        (C) STRANDEDNESS: double
        (D) TOPOLOGY: linear (ii) MOLECULE TYPE: other nucleic acid (iii) HYPOTHETICAL:no (iv) ANTI-SENSE: no (v) FRAGMENT TYPE: internal (vi) ORIGINAL SOURCE:

(A) ORGANISM: human (ix) FEATURE:
        (D) OTHER INFORMATION: locus specific amplification primer for
            HLA-C gene (xi) SEQUENCE DESCRIPTION: SEQ ID NO:33:

GACCCGGGGA GCCGCGCA                                                  18

(2) INFORMATION FOR SEQ ID NO: 34:

(i) SEQUENCE CHARACTERISTICS:
        (A) LENGTH: 24
        (B) TYPE: nucleic acid
        (C) STRANDEDNESS: double
        (D) TOPOLOGY: linear (ii) MOLECULE TYPE: other nucleic acid (iii) HYPOTHETICAL:no (iv) ANTI-SENSE: yes (v) FRAGMENT TYPE: internal (vi) ORIGINAL SOURCE:
        (A) ORGANISM: human (ix) FEATURE:
        (D) OTHER INFORMATION: locus specific amplification primer for
            HLA-C gene (xi) SEQUENCE DESCRIPTION: SEQ ID NO:34:

CGCTGATCCC ATTTTCCTCC CCTC                                           24

(2) INFORMATION FOR SEQ ID NO: 35:

(i) SEQUENCE CHARACTERISTICS:
        (A) LENGTH: 32
        (B) TYPE: nucleic acid
        (C) STRANDEDNESS: double
        (D) TOPOLOGY: linear (ii) MOLECULE TYPE: other nucleic acid (iii) HYPOTHETICAL:no (iv) ANTI-SENSE: yes (v) FRAGMENT TYPE: internal (vi) ORIGINAL SOURCE:
        (A) ORGANISM: human (ix) FEATURE:
        (D) OTHER INFORMATION: locus specific amplification primer for
            HLA-C gene (xi) SEQUENCE DESCRIPTION: SEQ ID NO:35:

CTCAGGAAAA CTCATSCCAT TCTCCATTCA AG                                  32

(2) INFORMATION FOR SEQ ID NO: 36:

(i) SEQUENCE CHARACTERISTICS:
        (A) LENGTH: 27
        (B) TYPE: nucleic acid
        (C) STRANDEDNESS: double
        (D) TOPOLOGY: linear (ii) MOLECULE TYPE: other nucleic acid (iii) HYPOTHETICAL:no -continued (iv) ANTI-SENSE: yes (v) FRAGMENT TYPE: internal (vi) ORIGINAL SOURCE:
            (A) ORGANISM: human (ix) FEATURE:
            (D) OTHER INFORMATION: locus specific amplification primer for
                HLA-C gene (xi) SEQUENCE DESCRIPTION: SEQ ID NO:36:

ACCACAGCTG CTGCAGTGGT CAAAGTG                                            27

(2) INFORMATION FOR SEQ ID NO: 37:

(i) SEQUENCE CHARACTERISTICS:
            (A) LENGTH: 26
            (B) TYPE: nucleic acid
            (C) STRANDEDNESS: double
            (D) TOPOLOGY: linear (ii) MOLECULE TYPE: other nucleic acid (iii) HYPOTHETICAL:no (iv) ANTI-SENSE: yes (v) FRAGMENT TYPE: internal (vi) ORIGINAL SOURCE:
            (A) ORGANISM: human (ix) FEATURE:
            (D) OTHER INFORMATION: locus specific amplification primer for
                HLA-C gene (xi) SEQUENCE DESCRIPTION: SEQ ID NO:37:

GAGGAAAGGT CAGCAGCCTG ACCACA                                             26

(2) INFORMATION FOR SEQ ID NO: 38:

(i) SEQUENCE CHARACTERISTICS:
            (A) LENGTH: 27
            (B) TYPE: nucleic acid
            (C) STRANDEDNESS: double
            (D) TOPOLOGY: linear (ii) MOLECULE TYPE: other nucleic acid (iii) HYPOTHETICAL:no (iv) ANTI-SENSE: yes (v) FRAGMENT TYPE: internal (vi) ORIGINAL SOURCE:
            (A) ORGANISM: human (ix) FEATURE:
            (D) OTHER INFORMATION: locus specific amplification primer for
                HLA-C gene (xi) SEQUENCE DESCRIPTION: SEQ ID NO:38:

GACTCAGAAA AGCTGGAATC AAACCTT                                            27

(2) INFORMATION FOR SEQ ID NO: 39:

(i) SEQUENCE CHARACTERISTICS:
            (A) LENGTH: 270
            (B) TYPE: nucleic acid
            (C) STRANDEDNESS: double
            (D) TOPOLOGY: linear

```
        (ii) MOLECULE TYPE: other nucleic acid (iii) HYPOTHETICAL:no (iv) ANTI-SENSE: no (v) FRAGMENT TYPE: internal (vi) ORIGINAL SOURCE:
             (A) ORGANISM: human (ix) FEATURE:
             (D) OTHER INFORMATION: consensus sequence of exon 2 of the
                 nonclassical genes (xi) SEQUENCE DESCRIPTION: SEQ ID NO:39:

GCTCCCACTC CATGAGGTAT TTCTACACCT CCGTGTCCCG GCCCGGCCGC              50

GGGGAGCCCC GCTTCATCGC AGTGGGCTAC GTGGACGACA CGCAGTTCGT             100

GCGGTTCGAC AGCGACGCCG CGAGTCCGAG GATGGAGCCG CGGGCGCCGT             150

GGATAGAGCA GGAGGGGCCG GAGTATTGGG ACCGGGAGAC ACAGAACTTC             200

AAGGCCCACA CACAGACTGA CCGAGAGAAC CTGCGGAACC TGCGCGGCTA             250

CTACAACCAG AGCGAGGCCG                                              270

(2) INFORMATION FOR SEQ ID NO: 40:

(i) SEQUENCE CHARACTERISTICS:
             (A) LENGTH: 276
             (B) TYPE: nucleic acid
             (C) STRANDEDNESS: double
             (D) TOPOLOGY: linear (ii) MOLECULE TYPE: other nucleic acid (iii) HYPOTHETICAL:no (iv) ANTI-SENSE: no (v) FRAGMENT TYPE: internal (vi) ORIGINAL SOURCE:
             (A) ORGANISM: human (ix) FEATURE:
             (D) OTHER INFORMATION: consensus sequence of exon 3 of the
                 nonclassical HLA genes (xi) SEQUENCE DESCRIPTION: SEQ ID NO:40:

GGTCTCACAC CCTCCAGAGG ATGTATGGCT GCGACGTGGG GCCGGACGGG              50

CGCCTCCTCC GCGGGTATAA CCAGTACGCC TACGACGGCA AGGATTACAT             100

CGCCCTGAAC GAGGACCTGC GCTCCTGGAC CGCGGCGGAC ACGGCGGCTC             150

AGATCACCCA GCGCAAGTGG GAGGCGGCCC GTGTGGCGGA GCAGCTGAGA             200

GCCTACCTGG AGGGCACGTG CGTGGAGTGG CTCCGCAGAT ACCTGGAGAA             250

CGGGAAGGAG ACGCTGCAGC GCGCGG                                       276

(2) INFORMATION FOR SEQ ID NO: 41:

(i) SEQUENCE CHARACTERISTICS:
             (A) LENGTH: 24
             (B) TYPE: nucleic acid
             (C) STRANDEDNESS: double
             (D) TOPOLOGY: linear (ii) MOLECULE TYPE: other nucleic acid
```

(iii) HYPOTHETICAL:no (iv) ANTI-SENSE: no (v) FRAGMENT TYPE: internal (vi) ORIGINAL SOURCE:
         (A) ORGANISM: human (ix) FEATURE:
         (D) OTHER INFORMATION: locus specific amplification primer for
             HLA-E gene (xi) SEQUENCE DESCRIPTION: SEQ ID NO:41:

CACTCCTTGA AGTATTTCCA CACT                                            24

(2) INFORMATION FOR SEQ ID NO: 42:

(i) SEQUENCE CHARACTERISTICS:
        (A) LENGTH: 27
        (B) TYPE: nucleic acid
        (C) STRANDEDNESS: double
        (D) TOPOLOGY: linear (ii) MOLECULE TYPE: other nucleic acid (iii) HYPOTHETICAL:no (iv) ANTI-SENSE: no (v) FRAGMENT TYPE: internal (vi) ORIGINAL SOURCE:
         (A) ORGANISM: human (ix) FEATURE:
         (D) OTHER INFORMATION: locus specific amplification primer for
             HLA-E gene (xi) SEQUENCE DESCRIPTION: SEQ ID NO:42:

TGGAAACGGC CTCTACCGGG AGTAGAG                                         27

(2) INFORMATION FOR SEQ ID NO: 43:

(i) SEQUENCE CHARACTERISTICS:
        (A) LENGTH:130
        (B) TYPE: nucleic acid
        (C) STRANDEDNESS: double
        (D) TOPOLOGY: linear (ii) MOLECULE TYPE: other nucleic acid (iii) HYPOTHETICAL:no (iv) ANTI-SENSE: no (v) FRAGMENT TYPE: internal (vi) ORIGINAL SOURCE:
         (A) ORGANISM: human (ix) FEATURE:
         (D) OTHER INFORMATION: consensus sequence of intron 1 of the
             HLA-E gene (xi) SEQUENCE DESCRIPTION: SEQ ID NO:43:

GTGAGTGCGG GGTCGGGATG GAAACGGCCT CTACCGGGAG TAGAGAGGGG               50

CCGGCCCGGC GGGGGCGAAG GACTCGGGGA GCCGCGCCGG GAGGAGGGTC              100

GGGCCGATCT CAGCCCCTCC TCGCCCCCAG                                    130

(2) INFORMATION FOR SEQ ID NO: 44:

(i) SEQUENCE CHARACTERISTICS:
            (A) LENGTH: 24
            (B) TYPE: nucleic acid
            (C) STRANDEDNESS: double
            (D) TOPOLOGY: linear (ii) MOLECULE TYPE: other nucleic acid (iii) HYPOTHETICAL:no (iv) ANTI-SENSE: yes (v) FRAGMENT TYPE: internal (vi) ORIGINAL SOURCE:
            (A) ORGANISM: human (ix) FEATURE:
            (D) OTHER INFORMATION: locus specific amplification primer for
                HLA-E gene (xi) SEQUENCE DESCRIPTION: SEQ ID NO:44:

TCTCCTTCCC CTTCTCCAGG TATT                                              24

(2) INFORMATION FOR SEQ ID NO: 45:

(i) SEQUENCE CHARACTERISTICS:
            (A) LENGTH: 34
            (B) TYPE: nucleic acid
            (C) STRANDEDNESS: double
            (D) TOPOLOGY: linear (ii) MOLECULE TYPE: other nucleic acid (iii) HYPOTHETICAL:no (iv) ANTI-SENSE: yes (v) FRAGMENT TYPE: internal (vi) ORIGINAL SOURCE:
            (A) ORGANISM: human (ix) FEATURE:
            (D) OTHER INFORMATION: locus specific amplification primer for
                HLA-E gene (xi) SEQUENCE DESCRIPTION: SEQ ID NO:45:

CACAGTCCTA GCCCAAGAAG GAGATGGGAG AGTA                                   34

(2) INFORMATION FOR SEQ ID NO: 46:

(i) SEQUENCE CHARACTERISTICS:
            (A) LENGTH: 621
            (B) TYPE: nucleic acid
            (C) STRANDEDNESS: double
            (D) TOPOLOGY: linear (ii) MOLECULE TYPE: other nucleic acid (iii) HYPOTHETICAL:no (iv) ANTI-SENSE: no (v) FRAGMENT TYPE: internal (vi) ORIGINAL SOURCE:
            (A) ORGANISM: human (ix) FEATURE:
            (D) OTHER INFORMATION: consensus sequence of intron 3 of the
                HLA-E gene (xi) SEQUENCE DESCRIPTION: SEQ ID NO:46:

```
GTAAGAGGGT CCACAGGGCT ACTCTCCCAT CTCCTTCTTG GGCTAGGACT                50

GTGCCCACAG CTGACAGACC TCAAACAGTA GAAGAAACAG GGATGGAGGC                100

CAGAATACCA CTCCTCCCTT GGATCAGGAG AGGGAGCTGT CACCTGAGGT                150

ACAGGAGATC CTATACCACA GAGTGACTCT CTTAAAGGGC CAGACCTCTC                200

TCAGGGGCAA TTAAGGAATC TAGTCTCGCT GGAGATTCCA TCCTTCAGAT                250

GAACTGATGA GCAGTTCTCT TTGACTCCCA GTATTAGGAA TCACGGGGGA                300

GTTTCTCTCG TGCCTGATTC TCAGCCCCAC ACCAAGAGTT TTTGGAGGTC                350

TGACTCCAGC TTTTCTCAGT CACTCAGCAT CCACACAGGC CAGGACCAGA                400

AATCCCTTTT CACCTTCTAC CCTGGGCTAG CTCATCCCGA TTCTAGAACT                450

TTCCAAGGAA TAAGAGGCTA TCCCAGATCC CTAAGTCCAG GCTGGTGTCA                500

AGGTTTTGTC CTCTTCTCCT ACTATAATTG TCCTCTTCCT TCTCAGGATG                550

GTCACATGGG TGCTGCTGGA GTGTCCCATG AGAGATACAA AGTGCCTGAA                600

TTTTCTGACT CTTCCCCTCA G                                               621
```

(2) INFORMATION FOR SEQ ID NO: 47:

(i) SEQUENCE CHARACTERISTICS:
        (A) LENGTH: 24
        (B) TYPE: nucleic acid
        (C) STRANDEDNESS: double
        (D) TOPOLOGY: linear (ii) MOLECULE TYPE: other nucleic acid (iii) HYPOTHETICAL:no (iv) ANTI-SENSE: no (v) FRAGMENT TYPE: internal (vi) ORIGINAL SOURCE:
        (A) ORGANISM: human (ix) FEATURE:
        (D) OTHER INFORMATION: locus specific amplification primer for
            HLA-F gene (xi) SEQUENCE DESCRIPTION: SEQ ID NO:47:

```
AGGTATTTCA GCACCGCTGT GTCG                                            24
```

(2) INFORMATION FOR SEQ ID NO: 48:

(i) SEQUENCE CHARACTERISTICS:
        (A) LENGTH: 20
        (B) TYPE: nucleic acid
        (C) STRANDEDNESS: double
        (D) TOPOLOGY: linear (ii) MOLECULE TYPE: other nucleic acid (iii) HYPOTHETICAL:no (iv) ANTI-SENSE: no (v) FRAGMENT TYPE: internal (vi) ORIGINAL SOURCE:
        (A) ORGANISM: human (ix) FEATURE:
        (D) OTHER INFORMATION: locus specific amplification primer for
            HLA-F gene (xi) SEQUENCE DESCRIPTION: SEQ ID NO:48:

GTGAGTGCGG GGTCCAGAGA                                                 20

(2) INFORMATION FOR SEQ ID NO: 49:

(i) SEQUENCE CHARACTERISTICS:
        (A) LENGTH:130
        (B) TYPE: nucleic acid
        (C) STRANDEDNESS: double
        (D) TOPOLOGY: linear (ii) MOLECULE TYPE: other nucleic acid (iii) HYPOTHETICAL:no (iv) ANTI-SENSE: no (v) FRAGMENT TYPE: internal (vi) ORIGINAL SOURCE:
        (A) ORGANISM: human (ix) FEATURE:
         (D) OTHER INFORMATION: consensus sequence of intron 1 of the
             HLA-F gene (xi) SEQUENCE DESCRIPTION: SEQ ID NO:49:

GTGAGTGCGG GGTCCAGAGA GAAACGGCCT CTGTGGGGAG GAGTGAGGGG               50

CCCGCCCGGT GGGGGCGCAG GACTCAGGGA GCCGCGCCCG GAGGAGGGTC              100

TGGCGGGTCT CAGCCCCTCC TCGCCCCCAG                                    130

(2) INFORMATION FOR SEQ ID NO: 50:

(i) SEQUENCE CHARACTERISTICS:
        (A) LENGTH: 22
        (B) TYPE: nucleic acid
        (C) STRANDEDNESS: double
        (D) TOPOLOGY: linear (ii) MOLECULE TYPE: other nucleic acid (iii) HYPOTHETICAL:no (iv) ANTI-SENSE: yes (v) FRAGMENT TYPE: internal (vi) ORIGINAL SOURCE:
        (A) ORGANISM: human (ix) FEATURE:
         (D) OTHER INFORMATION: locus specific amplification primer for
             HLA-F gene (xi) SEQUENCE DESCRIPTION: SEQ ID NO:50:

GCGTCTCCTT CCCATTCTCC AA                                             22

(2) INFORMATION FOR SEQ ID NO: 51:

(i) SEQUENCE CHARACTERISTICS:
        (A) LENGTH: 23
        (B) TYPE: nucleic acid
        (C) STRANDEDNESS: double
        (D) TOPOLOGY: linear (ii) MOLECULE TYPE: other nucleic acid (iii) HYPOTHETICAL:no (iv) ANTI-SENSE: yes (v) FRAGMENT TYPE: internal (vi) ORIGINAL SOURCE:
            (A) ORGANISM: human (ix) FEATURE:
            (D) OTHER INFORMATION: locus specific amplification primer for
                HLA-F gene (xi) SEQUENCE DESCRIPTION: SEQ ID NO:51:

CAACCTTGTG CGAGGCCATC CCA                                                 23

(2) INFORMATION FOR SEQ ID NO: 52:

(i) SEQUENCE CHARACTERISTICS:
            (A) LENGTH: 544
            (B) TYPE: nucleic acid
            (C) STRANDEDNESS: double
            (D) TOPOLOGY: linear (ii) MOLECULE TYPE: other nucleic acid (iii) HYPOTHETICAL:no (iv) ANTI-SENSE: no (v) FRAGMENT TYPE: internal (vi) ORIGINAL SOURCE:
            (A) ORGANISM: human (ix) FEATURE:
            (D) OTHER INFORMATION: consensus sequence of intron 3 of the
                HLA-F gene (xi) SEQUENCE DESCRIPTION: SEQ ID NO:52:

GTACCAGGGG CCATGGGCGC CTTCCCTATC TCCTGTAGAT CTCTTGGGAT                    50

GGCCTCGCAC AAGGTTGGGA GGAAAGTGGG CCCAATGCTA GGATATCGCC                   100

CTCCCTCTAG TCCTGAGTAG AAGAATCTT CCTGGCTTTT CGAGATCCGG                    150

TACCAGAGAG TGATTGTGAG AGTCCGCCCT GCTCTCTTGG ACAATTAAGG                   200

GATGAAATGG AGGAGGACAG TCCCTGGTCC CCTTTGAGCC TCCAACAGCT                   250

GCCGTGACTT TTCTCTCAGG TTTTGTCTCT GCCTCACACT CAATGTGTTT                   300

GGGGCTCTGA TTCCAGTCCC TCGCCCTCCA CTTAGTCAGG CCAGAAGTCC                   350

CTGCTCCCGC TCAGAGACTC GAACTTTCCA AGGAATAGGA GATTTTCCCA                   400

GGTGTCTGTG TCCAGCCTGG TGTCTGGGTT CTGTGCTCCC TTCCCCACCC                   450

CAGGTGTCCT GTCCAGTCTC AGGTTGGTCA CATGGGTGCT GCTGGGGTTT                   500

CCCATGAGGA GTGCAAAGTG CCTGAATTTT CTGACTCTTC TCAG                         544

(2) INFORMATION FOR SEQ ID NO: 53:

(i) SEQUENCE CHARACTERISTICS:
            (A) LENGTH: 21
            (B) TYPE: nucleic acid
            (C) STRANDEDNESS: double
            (D) TOPOLOGY: linear (ii) MOLECULE TYPE: other nucleic acid (iii) HYPOTHETICAL:no (iv) ANTI-SENSE: no (v) FRAGMENT TYPE: internal (vi) ORIGINAL SOURCE:

(A) ORGANISM: human (ix) FEATURE:
        (D) OTHER INFORMATION: locus specific amplification primer for
            HLA-G gene (xi) SEQUENCE DESCRIPTION: SEQ ID NO:53:

GGTTCGACAG CGACTCGGCG T                                                21

(2) INFORMATION FOR SEQ ID NO: 54:

(i) SEQUENCE CHARACTERISTICS:
        (A) LENGTH: 23
        (B) TYPE: nucleic acid
        (C) STRANDEDNESS: double
        (D) TOPOLOGY: linear (ii) MOLECULE TYPE: other nucleic acid (iii) HYPOTHETICAL:no (iv) ANTI-SENSE: no (v) FRAGMENT TYPE: internal (vi) ORIGINAL SOURCE:
        (A) ORGANISM: human (ix) FEATURE:
        (D) OTHER INFORMATION: locus specific amplification primer for
            HLA-G gene (xi) SEQUENCE DESCRIPTION: SEQ ID NO:54:

CGGCGGGGGC GCAGGACTCG GCA                                              23

(2) INFORMATION FOR SEQ ID NO: 55:

(i) SEQUENCE CHARACTERISTICS:
        (A) LENGTH: 129
        (B) TYPE: nucleic acid
        (C) STRANDEDNESS: double
        (D) TOPOLOGY: linear (ii) MOLECULE TYPE: other nucleic acid (iii) HYPOTHETICAL:no (iv) ANTI-SENSE: no (v) FRAGMENT TYPE: internal (vi) ORIGINAL SOURCE:
        (A) ORGANISM: human (ix) FEATURE:
        (D) OTHER INFORMATION: consensus sequence of intron 1 of the
            HLA-G gene (xi) SEQUENCE DESCRIPTION: SEQ ID NO:55:

GTGAGTGCGG GGTCAGGAGG GAAACGGCCC CTGCGCGGAG GAGGGAGGGG                  50

CCCCCCCGGC GGGGGCGCAG GACTCGGCAG CCGCGCCGGG AGGAGGGTCG                 100

GGCGGGTCTC AACCCCTCCT CGCCCCCAG                                        129

(2) INFORMATION FOR SEQ ID NO: 56:

(i) SEQUENCE CHARACTERISTICS:
        (A) LENGTH: 21
        (B) TYPE: nucleic acid
        (C) STRANDEDNESS: double
        (D) TOPOLOGY: linear (ii) MOLECULE TYPE: other nucleic acid (iii) HYPOTHETICAL:no (iv) ANTI-SENSE: yes (v) FRAGMENT TYPE: internal (vi) ORIGINAL SOURCE:
         (A) ORGANISM: human (ix) FEATURE:
         (D) OTHER INFORMATION: locus specific amplification primer for
             HLA-G gene (xi) SEQUENCE DESCRIPTION: SEQ ID NO:56:

TCTCCTTCCC GTTCTCCAGG T                                           21

(2) INFORMATION FOR SEQ ID NO: 57:

(i) SEQUENCE CHARACTERISTICS:
         (A) LENGTH: 29
         (B) TYPE: nucleic acid
         (C) STRANDEDNESS: double
         (D) TOPOLOGY: linear (ii) MOLECULE TYPE: other nucleic acid (iii) HYPOTHETICAL:no (iv) ANTI-SENSE: yes (v) FRAGMENT TYPE: internal (vi) ORIGINAL SOURCE:
         (A) ORGANISM: human (ix) FEATURE:
         (D) OTHER INFORMATION: locus specific amplification primer for
             HLA-G gene (xi) SEQUENCE DESCRIPTION: SEQ ID NO:57:

TCCTCCTCTC CTTGTGCTAG GCCAGGCTG                                   29

(2) INFORMATION FOR SEQ ID NO: 58:

(i) SEQUENCE CHARACTERISTICS:
         (A) LENGTH: 21
         (B) TYPE: nucleic acid
         (C) STRANDEDNESS: double
         (D) TOPOLOGY: linear (ii) MOLECULE TYPE: other nucleic acid (iii) HYPOTHETICAL:no (iv) ANTI-SENSE: no (v) FRAGMENT TYPE: internal (vi) ORIGINAL SOURCE:
         (A) ORGANISM: human (ix) FEATURE:
         (D) OTHER INFORMATION: locus specific amplification primer for
             HLA-H gene (xi) SEQUENCE DESCRIPTION: SEQ ID NO:58:

GAGCCCCGCT TCATCTCCGT C                                           21

(2) INFORMATION FOR SEQ ID NO: 59:

(i) SEQUENCE CHARACTERISTICS:

(A) LENGTH: 21
        (B) TYPE: nucleic acid
        (C) STRANDEDNESS: double
        (D) TOPOLOGY: linear (ii) MOLECULE TYPE: other nucleic acid (iii) HYPOTHETICAL:no (iv) ANTI-SENSE: no (v) FRAGMENT TYPE: internal (vi) ORIGINAL SOURCE:
         (A) ORGANISM: human (ix) FEATURE:
         (D) OTHER INFORMATION: locus specific amplification primer for
             HLA-J gene (xi) SEQUENCE DESCRIPTION: SEQ ID NO:59:

AGCACCGCCG TTTCCTGGCC G                                           21

(2) INFORMATION FOR SEQ ID NO: 60:

(i) SEQUENCE CHARACTERISTICS:
         (A) LENGTH: 26
         (B) TYPE: nucleic acid
         (C) STRANDEDNESS: double
         (D) TOPOLOGY: linear (ii) MOLECULE TYPE: other nucleic acid (iii) HYPOTHETICAL:no (iv) ANTI-SENSE: no (v) FRAGMENT TYPE: internal (vi) ORIGINAL SOURCE:
         (A) ORGANISM: human (ix) FEATURE:
         (D) OTHER INFORMATION: locus specific amplification primer for
             HLA-K gene (xi) SEQUENCE DESCRIPTION: SEQ ID NO:60:

ACTCCATAAG GTAGTTCAGC ACCGCC                                      26

(2) INFORMATION FOR SEQ ID NO: 61:

(i) SEQUENCE CHARACTERISTICS:
         (A) LENGTH: 23
         (B) TYPE: nucleic acid
         (C) STRANDEDNESS: double
         (D) TOPOLOGY: linear (ii) MOLECULE TYPE: other nucleic acid (iii) HYPOTHETICAL:no (iv) ANTI-SENSE: no (v) FRAGMENT TYPE: internal (vi) ORIGINAL SOURCE:
         (A) ORGANISM: human (ix) FEATURE:
         (D) OTHER INFORMATION: locus specific amplification primer for
             HLA-L gene (xi) SEQUENCE DESCRIPTION: SEQ ID NO:61:

GTGCGGTTCG ACAGCGACTC CGT                                         23

(2) INFORMATION FOR SEQ ID NO: 62:

(i) SEQUENCE CHARACTERISTICS:
        (A) LENGTH: 15
        (B) TYPE: nucleic acid
        (C) STRANDEDNESS: double
        (D) TOPOLOGY: linear (ii) MOLECULE TYPE: other nucleic acid (iii) HYPOTHETICAL:no (iv) ANTI-SENSE: yes (v) FRAGMENT TYPE: internal (vi) ORIGINAL SOURCE:
        (A) ORGANISM: human (ix) FEATURE:
        (D) OTHER INFORMATION: hybridization probe 131R for typing of
            HLA Class I genes (xi) SEQUENCE DESCRIPTION: SEQ ID NO:62:

CGCTCTTGGA CCGCG                                       15

(2) INFORMATION FOR SEQ ID NO: 63:

(i) SEQUENCE CHARACTERISTICS:
        (A) LENGTH: 19
        (B) TYPE: nucleic acid
        (C) STRANDEDNESS: double
        (D) TOPOLOGY: linear (ii) MOLECULE TYPE: other nucleic acid (iii) HYPOTHETICAL:no (iv) ANTI-SENSE: yes (v) FRAGMENT TYPE: internal (vi) ORIGINAL SOURCE:
        (A) ORGANISM: human (ix) FEATURE:
        (D) OTHER INFORMATION: hybridization probe HBB034 for typing
            of HLA Class I genes (xi) SEQUENCE DESCRIPTION: SEQ ID NO:63:

GTTCGTGAGG TTCGACAGC                                  19

(2) INFORMATION FOR SEQ ID NO: 64:

(i) SEQUENCE CHARACTERISTICS:
        (A) LENGTH: 19
        (B) TYPE: nucleic acid
        (C) STRANDEDNESS: double
        (D) TOPOLOGY: linear (ii) MOLECULE TYPE: other nucleic acid (iii) HYPOTHETICAL:no (iv) ANTI-SENSE: yes (v) FRAGMENT TYPE: internal (vi) ORIGINAL SOURCE:
        (A) ORGANISM: human (ix) FEATURE:
        (D) OTHER INFORMATION: hybridization probe HYB035 for typing of HLA Class I genes (xi) SEQUENCE DESCRIPTION: SEQ ID NO:64:

CGCCGTGGGT GGAGCAGGA                                                19

(2) INFORMATION FOR SEQ ID NO: 65:

(i) SEQUENCE CHARACTERISTICS:
        (A) LENGTH: 18
        (B) TYPE: nucleic acid
        (C) STRANDEDNESS: double
        (D) TOPOLOGY: linear (ii) MOLECULE TYPE: other nucleic acid (iii) HYPOTHETICAL:no (iv) ANTI-SENSE: yes (v) FRAGMENT TYPE: internal (vi) ORIGINAL SOURCE:
        (A) ORGANISM: human (ix) FEATURE:
        (D) OTHER INFORMATION: hybridization probe EE2-210 for typing
            of HLA Class I genes (xi) SEQUENCE DESCRIPTION: SEQ ID NO:65:

GCACAGACAC GGAACACC                                                 18

(2) INFORMATION FOR SEQ ID NO: 66:

(i) SEQUENCE CHARACTERISTICS:
        (A) LENGTH: 18
        (B) TYPE: nucleic acid
        (C) STRANDEDNESS: double
        (D) TOPOLOGY: linear (ii) MOLECULE TYPE: other nucleic acid (iii) HYPOTHETICAL:no (iv) ANTI-SENSE: no (v) FRAGMENT TYPE: internal (vi) ORIGINAL SOURCE:
        (A) ORGANISM: human (ix) FEATURE:
        (D) OTHER INFORMATION: hybridization probe FE2-200 for typing
            of HLA Class I genes (xi) SEQUENCE DESCRIPTION: SEQ ID NO:66:

GTCTGTGCGT TGGCCTTG                                                 18

(2) INFORMATION FOR SEQ ID NO: 67:

(i) SEQUENCE CHARACTERISTICS:
        (A) LENGTH: 18
        (B) TYPE: nucleic acid
        (C) STRANDEDNESS: double
        (D) TOPOLOGY: linear (ii) MOLECULE TYPE: other nucleic acid (iii) HYPOTHETICAL:no (iv) ANTI-SENSE: yes (v) FRAGMENT TYPE: internal (vi) ORIGINAL SOURCE:
              (A) ORGANISM: human (ix) FEATURE:
              (D) OTHER INFORMATION: hybridization probe GE2-183 for typing
                  of HLA Class I genes (xi) SEQUENCE DESCRIPTION: SEQ ID NO:67:

GAGGAGACAC GGAACACC                                                18

(2) INFORMATION FOR SEQ ID NO: 68:

(i) SEQUENCE CHARACTERISTICS:
              (A) LENGTH: 18
              (B) TYPE: nucleic acid
              (C) STRANDEDNESS: double
              (D) TOPOLOGY: linear (ii) MOLECULE TYPE: other nucleic acid (iii) HYPOTHETICAL:no (iv) ANTI-SENSE: no (v) FRAGMENT TYPE: internal (vi) ORIGINAL SOURCE:
              (A) ORGANISM: human (ix) FEATURE:
              (D) OTHER INFORMATION: hybridization probe HE3-479 for typing
                  of HLA Class I genes (xi) SEQUENCE DESCRIPTION: SEQ ID NO:68:

TCCACGAACT CGCCCTCC                                                18

(2) INFORMATION FOR SEQ ID NO: 69:

(i) SEQUENCE CHARACTERISTICS:
              (A) LENGTH: 18
              (B) TYPE: nucleic acid
              (C) STRANDEDNESS: double
              (D) TOPOLOGY: linear (ii) MOLECULE TYPE: other nucleic acid (iii) HYPOTHETICAL:no (iv) ANTI-SENSE: no (v) FRAGMENT TYPE: internal (vi) ORIGINAL SOURCE:
              (A) ORGANISM: human (ix) FEATURE:
              (D) OTHER INFORMATION: hybridization probe JE3-274 for typing
                  of HLA Class I genes (xi) SEQUENCE DESCRIPTION: SEQ ID NO:69:

TTCCCTGGAG GATGTGAT                                                18

(2) INFORMATION FOR SEQ ID NO: 70:

(i) SEQUENCE CHARACTERISTICS:
              (A) LENGTH: 19
              (B) TYPE: nucleic acid
              (C) STRANDEDNESS: double
              (D) TOPOLOGY: linear (ii) MOLECULE TYPE: other nucleic acid (iii) HYPOTHETICAL:no (iv) ANTI-SENSE: yes (v) FRAGMENT TYPE: internal (vi) ORIGINAL SOURCE:
            (A) ORGANISM: human (ix) FEATURE:
            (D) OTHER INFORMATION: hybridization probe HLB-032 for typing
                of HLA Class I genes (xi) SEQUENCE DESCRIPTION: SEQ ID NO:70:

CAGCGACTCC GTGAGTCCG                                                        19

(2) INFORMATION FOR SEQ ID NO: 71:

(i) SEQUENCE CHARACTERISTICS:
            (A) LENGTH: 15
            (B) TYPE: nucleic acid
            (C) STRANDEDNESS: double
            (D) TOPOLOGY: linear (ii) MOLECULE TYPE: other nucleic acid (iii) HYPOTHETICAL:no (iv) ANTI-SENSE: yes (v) FRAGMENT TYPE: internal (vi) ORIGINAL SOURCE:
            (A) ORGANISM: human (ix) FEATURE:
            (D) OTHER INFORMATION: hybridization probe 142IK for typing
                of HLA Class I genes (xi) SEQUENCE DESCRIPTION: SEQ ID NO:71:

CAGATCACCA AGCGC                                                            15

(2) INFORMATION FOR SEQ ID NO: 72:

(i) SEQUENCE CHARACTERISTICS:
            (A) LENGTH: 15
            (B) TYPE: nucleic acid
            (C) STRANDEDNESS: double
            (D) TOPOLOGY: linear (ii) MOLECULE TYPE: other nucleic acid (iii) HYPOTHETICAL:no (iv) ANTI-SENSE: yes (v) FRAGMENT TYPE: internal (vi) ORIGINAL SOURCE:
            (A) ORGANISM: human (ix) FEATURE:
            (D) OTHER INFORMATION: hybridization probe 114EH for typing
                of HLA Class I genes (xi) SEQUENCE DESCRIPTION: SEQ ID NO:72:

TATGAACAGC ACGCC                                                            15

(2) INFORMATION FOR SEQ ID NO: 73:

(i) SEQUENCE CHARACTERISTICS:
            (A) LENGTH: 19
            (B) TYPE: nucleic acid
            (C) STRANDEDNESS: double (D) TOPOLOGY: linear (ii) MOLECULE TYPE: other nucleic acid (iii) HYPOTHETICAL:no (iv) ANTI-SENSE: yes (v) FRAGMENT TYPE: internal (vi) ORIGINAL SOURCE:
        (A) ORGANISM: human (ix) FEATURE:
        (D) OTHER INFORMATION: hybridization probe HXC008 for typing
            of HLA Class I genes (xi) SEQUENCE DESCRIPTION: SEQ ID NO:73:

CTGCGGATCG CGCTCCGCT                                                19

(2) INFORMATION FOR SEQ ID NO: 74:

(i) SEQUENCE CHARACTERISTICS:
        (A) LENGTH: 19
        (B) TYPE: nucleic acid
        (C) STRANDEDNESS: double
        (D) TOPOLOGY: linear (ii) MOLECULE TYPE: other nucleic acid (iii) HYPOTHETICAL:no (iv) ANTI-SENSE: yes (v) FRAGMENT TYPE: internal (vi) ORIGINAL SOURCE:
        (A) ORGANISM: human (ix) FEATURE:
        (D) OTHER INFORMATION: hybridization probe HBB055 for typing
            of HLA Class I genes (xi) SEQUENCE DESCRIPTION: SEQ ID NO:74:

CCGCGAGTCC GAGGATGGC                                                19

(2) INFORMATION FOR SEQ ID NO: 75:

(i) SEQUENCE CHARACTERISTICS:
        (A) LENGTH: 19
        (B) TYPE: nucleic acid
        (C) STRANDEDNESS: double
        (D) TOPOLOGY: linear (ii) MOLECULE TYPE: other nucleic acid (iii) HYPOTHETICAL:no (iv) ANTI-SENSE: yes (v) FRAGMENT TYPE: internal (vi) ORIGINAL SOURCE:
        (A) ORGANISM: human (ix) FEATURE:
        (D) OTHER INFORMATION: hybridization probe HBC009 for typing
            of HLA Class I genes (xi) SEQUENCE DESCRIPTION: SEQ ID NO:75:

CTGCGGACCC TGCTCCGCT                                                19

(2) INFORMATION FOR SEQ ID NO: 76:

```
    (i) SEQUENCE CHARACTERISTICS:
        (A) LENGTH: 19
        (B) TYPE: nucleic acid
        (C) STRANDEDNESS: double
        (D) TOPOLOGY: linear (ii) MOLECULE TYPE: other nucleic acid (iii) HYPOTHETICAL:no (iv) ANTI-SENSE: yes (v) FRAGMENT TYPE: internal (vi) ORIGINAL SOURCE:
        (A) ORGANISM: human (ix) FEATURE:
        (D) OTHER INFORMATION: hybridization probe HYE024 for typing
            of HLA Class I genes (xi) SEQUENCE DESCRIPTION: SEQ ID NO:76:

GGACCTGCGC TCCTGGACC                                              19

(2) INFORMATION FOR SEQ ID NO: 77:

(i) SEQUENCE CHARACTERISTICS:
        (A) LENGTH: 19
        (B) TYPE: nucleic acid
        (C) STRANDEDNESS: double
        (D) TOPOLOGY: linear (ii) MOLECULE TYPE: other nucleic acid (iii) HYPOTHETICAL:no (iv) ANTI-SENSE: yes (v) FRAGMENT TYPE: internal (vi) ORIGINAL SOURCE:
        (A) ORGANISM: human (ix) FEATURE:
        (D) OTHER INFORMATION: hybridization probe HBD080 for typing
            of HLA Class I genes (xi) SEQUENCE DESCRIPTION: SEQ ID NO:77:

CGGGTACCAC CAGGACGCC                                              19

(2) INFORMATION FOR SEQ ID NO: 78:

(i) SEQUENCE CHARACTERISTICS:
        (A) LENGTH: 19
        (B) TYPE: nucleic acid
        (C) STRANDEDNESS: double
        (D) TOPOLOGY: linear (ii) MOLECULE TYPE: other nucleic acid (iii) HYPOTHETICAL:no (iv) ANTI-SENSE: yes (v) FRAGMENT TYPE: internal (vi) ORIGINAL SOURCE:
        (A) ORGANISM: human (ix) FEATURE:
        (D) OTHER INFORMATION: hybridization probe HBD083 for typing
            of HLA Class I genes (xi) SEQUENCE DESCRIPTION: SEQ ID NO:78:
```

```
CGGGTATGAC CAGGACGCC                                              19

(2) INFORMATION FOR SEQ ID NO: 79:

(i) SEQUENCE CHARACTERISTICS:
        (A) LENGTH: 19
        (B) TYPE: nucleic acid
        (C) STRANDEDNESS: double
        (D) TOPOLOGY: linear (ii) MOLECULE TYPE: other nucleic acid (iii) HYPOTHETICAL:no (iv) ANTI-SENSE: yes (v) FRAGMENT TYPE: internal (vi) ORIGINAL SOURCE:
        (A) ORGANISM: human (ix) FEATURE:
        (D) OTHER INFORMATION: hybridization probe HBD086 for typing
            of HLA Class I genes (xi) SEQUENCE DESCRIPTION: SEQ ID NO:79:

CGGGTATAAC CAGTTAGCC                                              19

(2) INFORMATION FOR SEQ ID NO: 80:

(i) SEQUENCE CHARACTERISTICS:
        (A) LENGTH: 19
        (B) TYPE: nucleic acid
        (C) STRANDEDNESS: double
        (D) TOPOLOGY: linear (ii) MOLECULE TYPE: other nucleic acid (iii) HYPOTHETICAL:no (iv) ANTI-SENSE: yes (v) FRAGMENT TYPE: internal (vi) ORIGINAL SOURCE:
        (A) ORGANISM: human (ix) FEATURE:
        (D) OTHER INFORMATION: hybridization probe HBF094 for typing
            of HLA Class I genes (xi) SEQUENCE DESCRIPTION: SEQ ID NO:80:

GACAAGCTGG AGCGCGCTG                                              19

(2) INFORMATION FOR SEQ ID NO: 81:

(i) SEQUENCE CHARACTERISTICS:
        (A) LENGTH: 19
        (B) TYPE: nucleic acid
        (C) STRANDEDNESS: double
        (D) TOPOLOGY: linear (ii) MOLECULE TYPE: other nucleic acid (iii) HYPOTHETICAL:no (iv) ANTI-SENSE: yes (v) FRAGMENT TYPE: internal (vi) ORIGINAL SOURCE:
        (A) ORGANISM: human
```

(ix) FEATURE:
             (D) OTHER INFORMATION: hybridization probe HBC065 for typing
                 of HLA Class I genes (xi) SEQUENCE DESCRIPTION: SEQ ID NO:81:

GAAGTACAAG CGCCAGGCA                                              19

(2) INFORMATION FOR SEQ ID NO: 82:

(i) SEQUENCE CHARACTERISTICS:
             (A) LENGTH: 19
             (B) TYPE: nucleic acid
             (C) STRANDEDNESS: double
             (D) TOPOLOGY: linear (ii) MOLECULE TYPE: other nucleic acid (iii) HYPOTHETICAL:no (iv) ANTI-SENSE: yes (v) FRAGMENT TYPE: internal (vi) ORIGINAL SOURCE:
             (A) ORGANISM: human (ix) FEATURE:
             (D) OTHER INFORMATION: hybridization probe HBC066 for typing
                 of HLA Class I genes (xi) SEQUENCE DESCRIPTION: SEQ ID NO:82:

GAACATGAAG GCCTCCGCG                                              19

(2) INFORMATION FOR SEQ ID NO: 83:

(i) SEQUENCE CHARACTERISTICS:
             (A) LENGTH: 18
             (B) TYPE: nucleic acid
             (C) STRANDEDNESS: double
             (D) TOPOLOGY: linear (ii) MOLECULE TYPE: other nucleic acid (iii) HYPOTHETICAL:no (iv) ANTI-SENSE: yes (v) FRAGMENT TYPE: internal (vi) ORIGINAL SOURCE:
             (A) ORGANISM: human (ix) FEATURE:
             (D) OTHER INFORMATION: hybridization probe 156R for typing
                 of HLA Class I genes (xi) SEQUENCE DESCRIPTION: SEQ ID NO:83:

GCGGAGCAGC GGAGAGCC                                               18

(2) INFORMATION FOR SEQ ID NO: 84:

(i) SEQUENCE CHARACTERISTICS:
             (A) LENGTH: 20
             (B) TYPE: nucleic acid
             (C) STRANDEDNESS: double
             (D) TOPOLOGY: linear (ii) MOLECULE TYPE: other nucleic acid (iii) HYPOTHETICAL:no (iv) ANTI-SENSE: no -continued

```
   (v) FRAGMENT TYPE: internal (vi) ORIGINAL SOURCE:
       (A) ORGANISM: human (ix) FEATURE:
       (D) OTHER INFORMATION: generic amplification primer for HLA (xi) SEQUENCE DESCRIPTION: SEQ ID NO:84:

TGCAGCGTCT CCTTCCCGTT                                                   20
```